US006395964B1

(12) United States Patent
Arntzen et al.

(10) Patent No.: US 6,395,964 B1
(45) Date of Patent: May 28, 2002

(54) ORAL IMMUNIZATION WITH TRANSGENIC PLANTS

(75) Inventors: Charles J. Arntzen; Hugh S. Mason, both of Ithaca, NY (US); Haq A. Tariq, San Antonio, TX (US); John D. Clements, New Orleans, LA (US)

(73) Assignees: The Texas A&M University System, College Station, TX (US); The Administrators of the Tulane Fund, New Orleans, LA (US)

( * ) Notice: Subject to any disclaimer, the term of this patent is extended or adjusted under 35 U.S.C. 154(b) by 0 days.

(21) Appl. No.: 08/817,906

(22) PCT Filed: Oct. 24, 1995

(86) PCT No.: PCT/US95/13376

§ 371 (c)(1),
(2), (4) Date: Aug. 4, 1997

(87) PCT Pub. No.: WO96/12801

PCT Pub. Date: May 2, 1996

(51) Int. Cl.[7] .......................... C12N 5/04; C12N 15/82; C12N 15/87; A01H 5/00
(52) U.S. Cl. ................. 800/288; 424/186.1; 424/257.1; 424/261.1; 435/69.3; 435/320.1; 435/419; 435/468; 800/287; 800/298
(58) Field of Search ................................ 800/278, 287, 800/288, 295, 298, FOR 101, FOR 102; 424/184.1, 185.1, 190.1, 192.1, 197.11, 236.1, 241.1, 257.1, 186.1, 261.1; 435/69.3, 410, 419, 320.1, 468; 536/23.1, 23.7

(56) References Cited

U.S. PATENT DOCUMENTS 5,612,487 A * 3/1997 Lam et al.
5,654,184 A * 8/1997 Curtiss, III et al.
5,679,880 A * 10/1997 Curtiss, III et al.
5,686,079 A * 11/1997 Curtiss, III et al.

FOREIGN PATENT DOCUMENTS

WO  WO90/02484  3/1990
WO  WO94/20135  9/1994

OTHER PUBLICATIONS

Ann De Clercq et al., Expression and Processing of an Arabidopsis 2S Albumin in Transgenic Tobacco, Plant Physiol. (1990) vol. 92, pp. 899–907.*
Aizpurua, H., *J. Exp. Med.*, 167:440–451 (1988).
Aldovini, A., *Technology Review*, 26–31 (1992).
An, *Meth. Enzymol.*, 153:292 (1987).
Arntzen, C., *Vaccines*, 339–344 (1994).
Beard, C.W., et al., "Preparation of Newcastle Disease Virus Hemagglutinin–Inhibition Test Antigen" Avian Diseases 19:692–699 (1975).
Bevan, *Ann. Rev. Genet.*, 16:357 (1982).
Bloom, B., *Nature*, 342 (1989).
Cardenas, *Infect. Immun*, 61:4629 (1993).
Carrington, *Plant Cell*, 3:353 (1991).
Cheville, et al., Vet. Path 9:38–52, 1972.
Clemens, *J. of Infec. Diseases*, 158:372–377 (1988).
Clemens, *Lancet*, 335:270 (1990).
Clements, *Infection and Immunity*, 24:760–769 (1979).
Clements, *Infect. Immunity*, 40:653 (1983).
Clements, *Infect. & Immunity*, 46:564–569 (1984).
Denecke, *EMBO J.*, 11:2345 (1992).
Dertzbaugh, *Infect. & Immunity*, 61:48–55 (1993).
Dertzbaugh, *Infect. & Immunity*, 61:384–390 (1993).
Dombrowski, *Plant Cell*, 5:587 (1993).
Elson, *Vaccine Research*, 1:227 (1992).
Faye, *Plant Physiol*, 89:845 (1989).
Gibbons, *Science*, 255:1351 (1992).
Golds, et al. in, *Methods in Molecular Biology*, Chapter 33, vol. 6, Plant Cell and Tissue Culture, J.W. Pollard and J.M. Walker, eds., pp. 341–371 (1990).
Haq, T.A. et al., *Science* 5211(268):714–716, 1995.
Hardy, *Proc. Natl. Acad. Sci.*, 85:7109 (1988).
Haugejorden, *J. Biol. Chem.*, 266:6015 (1991).
Herman, *Planta*, 182:305 (1991).
Hirst, *Proc. Natl. Acad. Sci.*, 84:7418 (1987).
Hofstra, *J. of Biol. Chem.*, 260:16037 (1985).
Holmgren, *Vaccine*, 11:1179 (1993).
Holwerda, *Plant Cell*, 4:307 (1992).
Horsch, *Plant Mol. Biology Manual*, A5, Kluwer Academic Pub. Dordecht (1988), p. 1–9.
Houghten, R.A. et al. Vaccines 86:21–25.
Jackson, "Oral Vaccine Models: Multiple Delivery Systems Employing Tetanus Toxoid," 19 in press Jefferson, *EMBO J.*, 6:3901 (1987).
Jiang, *J. Virol.* 66:6527 (1992).
Jobling, *Infec. & Immunity*, 60:4915 (1992).
Jones, *EMBO J.*, 4:2411 (1985).
Lebens, *Bio/Technology*, 11:1574 (1993).
McFerran, et al., Vet. Rec 82:589, 1968.
Mason, *Plant Mol. Biol.*, 11:845 (1988).
Mason, *Proc. Natl. Acad. Sci. USA*, 89:11745 (1992).
Mason, *Plant Cell*, 5:241 (1993).

(List continued on next page.)

Primary Examiner—Amy J. Nelson
Assistant Examiner—Ashwin Mehta
(74) Attorney, Agent, or Firm—Fulbright & Jaworski, L.L.P.

(57) ABSTRACT

The oral antigens and adjuvants of the present invention are produced in transgenic plants and then administered through the consumption of the transgenic plant. DNA sequences both natural and synthetic encoding for the expression of immunogenic agents which are capable of causing an immune response in animals when fed in edible plants, plant tissues, or derived plant materials are constructed, and plants transformed for stable or transient expression in plant cells. The present invention provides the first known functional method for immunizing animals via transgenic plants, where the plants express bacterial antigens that act as both immunogen and adjuvants when the transgenic plant material expressing the antigens is fed to animals.

15 Claims, 18 Drawing Sheets

OTHER PUBLICATIONS

Mason, *J. of NIH Research*, 5:49 (1993).
Mason, et al. J. of Cellular Biochemistry Supplement 18A, Abstract X1–211 "Expression of Candidate Oral Vaccine Antigens in Transgenic Plants", p. 98, Jan. 4–23, (1994).
Matsuoka, *Proc. Natl. Acad. Sci USA*, 88:834 (1991).
McGhee, *Infectious Agents & Diseases*, 2:55 (1993).
Merritt, *Molecular Microbiology*, 13:745 (1994).
Mestecky, *Microbiology & Immunology*, 146:3 (1989).
Munro, *Cell*, 48:988 (1987).
Nashar, *Vaccine*, 11:235 (1993).
Negrutiu, *Plant Mol. Biol.*, 8:363 (1987).
Ochatt, S. J. et al. in, *Methods in Molecular Biology*, Chapter 20, vol. 6, Plant Cell and Tissue Culture, J.W. Pollard and J.M. Walker, eds., pp. 193–207 (1990).
Peltola, *Lancet*, 338:1285 (1991).
Perl, *Plant Science*, 73:89 (1991).
Porta, *Virology*, 202:949 (1994).
Russell, P.H., Vet Immuno and Immunopathology 42:357–365, 1994.
Sack, *Infec. & Immunity*, 11:334 (1975).
Sanchez, *Lancet*, 344:1273 (1994).
Schodel, *Gene*, 99:225 (1991).
Schonberger, *Molecular Microbiology*, 5:2663 (1991).
Sixma, *Nature*, 351:371 (1991).
Sixma, *J. Mol. Biol.*, 230:890 (1993).
Sonnewald, *Plant J.*, 1:95 (1991).
Streatfield, *Proc. Natl. Acad. Sci.*, 89:12140 (1992).
Thanavala, *Proc. Natl. Acad. Sci.*, 92:3358 (1995).
Usha, *Virology*, 197:366 (1993).
VanEck and Goren, Avian Pathology 20:497–507, (1991).
Wandelt, *The Plant Journal*, 2:181 (1992).
Wenzler, *Plant Science*, 63:79 (1989).
Wenzler, *Plant Mol. Biol.*, 12:41 (1989).
Zhang, *J. Mol. Biol.*, 251(4):563–573 (1995).

* cited by examiner

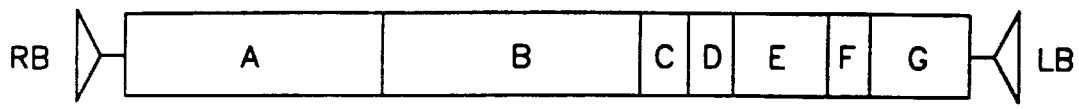

A) 5' NOS PROMOTER, nptII 3' NOS TERMINATOR

B) PROMOTER AND 5' REGULATORY ELEMENTS:
1. CaMV 35 S PROMOTER
2. PATATIN PROMOTER
3. vsp B PROMOTER

C) TRANSLATIONAL ENHANCER:
TOBACCO ETCH VIRUS 5'-UTR

D) SUBCELLULAR TARGETING DOMAINS:
1. SPORAMIN A-N TERMINAL SIGNAL SEQUENCE
2. VSP SIGNAL SEQUENCE

E) *E COLI* HEAT LABILE ENTEROTOXIN SUBUNIT B (LT-B) CODING SEQUENCE.

F) ENDOPLASMIC RETICULUM RETENTION SIGNAL (KDEL)

(G) vspB POLYADENYLATION SIGNAL

LEFT AND RIGHT BORDER SEQUENCES

FIG. 7

ORAL IMMUNIZATION WITH TRANSGENIC PLANTS

This application is the National Stage of International Application No. PCT/US95/13376 filed on Oct. 24, 1995 which was a continuation-in-part of U.S. application Ser. No. 08/382,716, filed Oct. 24, 1994.

FIELD OF THE INVENTION

A This invention relates generally to the production of oral vaccine adjuvants and oral vaccines in edible transgenic plants and, more particularly, to causing an immune response in animals which eat the transgenic plant material. The present invention relates more specifically to the production of transgenic plants using the genes encoding bacterial toxin subunits LT-A and LT-B or CT-A and CT-B and the use of the expressed protein for inducing immune responses in mammals, alone and with other associated antigenic agents.

Accordingly, this invention relates to the introduction into plants of genes encoding colonization or virulence antigens or antigenic portions thereof of pathogens which colonize on or invade through mucosal surfaces of mammals. More particularly, this invention relates to the introduction of genes encoding LT-B or CT-B containing proteins into plants so that the plants can produce the LT-B or CT-B containing protein.

This invention further represents a significant and unexpected improvement over the prior art in that it enables the actual immunization of animals against bacterial antigens by feeding animals transgenic plants in which sufficient levels of the bacterial antigen has been expressed in order to induce immunity. Further, this invention demonstrates the additional and unexpected improvement of an adjuvant effect caused when immunizing animals with transgenic plants containing bacterial toxin antigens.

BACKGROUND OF THE INVENTION

Infectious diseases have plagued life on earth probably from its inception. Such diseases affect not only man but animals. In economically advanced countries of the world, infectious diseases are 1) temporarily disabling; 2) permanently disabling or crippling; or 3) fatal. In the lesser developed countries, infectious diseases tend to fall into the latter two categories, permanently disabling or crippling and fatal, due to may factors, including a lack of preventive immunization and curative medicine.

It is generally acknowledged that the usefulness of antibiotics to effectively control bacterial pathogens is becoming increasingly difficult, because of the increased occurrence of antibiotic-resistant pathogens. Thus, prevention of infectious diseases is more cost effective than the ultimate treatment of the disease once it has occurred. As a result, increased attention is being focused on the development of vaccines.

Vaccines are administered to humans and animals to induce their immune systems to produce antibodies against viruses, bacteria, and other types of pathogenic organisms. In the economically advanced countries of the world, vaccines have brought many diseases under control. In particular, many viral diseases are now prevented due to the development of immunization programs. The virtual elimination of smallpox is an example of the effectiveness of a vaccine worldwide. But many vaccines for such diseases as poliomyelitis, measles, mumps, rabies, foot and mouth, and hepatitis B are still too expensive for the lesser developed countries to provide to their large human and animal populations. Lack of these preventative measures for animal populations can worsen the human condition by creating food shortages.

Because of simplicity of delivery of vaccines by oral delivery, there is great current interest in discovering new oral vaccine technology. Appropriately delivered oral immunogens can stimulate both humoral and cellular immunity and have the potential to provide cost-effective, safe vaccines for use in developing countries or inner cities where large-scale parenteral immunization is not practical or extremely difficult to implement. Such vaccines may be based upon bacterial or viral vector systems expressing protective epitopes from diverse pathogens (multivalent vaccines) or may be based upon purified antigens delivered singularly or in combination with relevant antigens or other pathogens.

A. Microbial Pathogenesis and Oral Vaccination

Microbial pathogens can infect a host by one of several mechanisms. They may enter through a break in the integument induced by trauma, they may be introduced by vector transmission, or they may interact with a mucosal surface. The majority of human pathogens initiate disease by the last mechanism, i.e., following interaction with mucosal surfaces. Bacterial and viral pathogens that act through this mechanism first make contact with the mucocal surface where they may attach and then colonize, or be taken up by specialized absorptive cells (M cells) in the epithelium that overly Peyer's patches and other lymphoid follicles. Organisms that enter the lymphoid tissues may be readily killed within the lymphoid follicles, thereby provoking a potentially protective immunological response as antigens are delivered to immune cells within the follicles (e.g., *Vibrio cholerae*). Alternatively, pathogenic organisms capable of surviving local defense mechanisms may spread from the follicles and subsequently cause local or systemic disease (e.g., Salmonella spp., poliovirus in immunocompromised hosts).

Secretory IgA (sIgA) antibodies directed against specific virulence determinants of infecting organism play an important role in overall mucosal immunity. In many cases, it is possible to prevent the initial infection of mucosal surfaces by stimulating production of mucosal sIgA levels directed against relevant virulence determinants of an infecting organism. Secretory IgA may prevent the initial interaction of the pathogen with the mucosal surface by blocking attachment and/or colonization, neutralizing surface acting toxins, or preventing invasion of the host cells.

Parenterally administered inactivated whole-cell and whole-virus preparations are effective at eliciting protective serum IgG and delayed type hypersensitivity reactions against organisms that have a significant serum phase in their pathogenesis (e.g., *Salmonella typhi*, Hepatitis B). However, parenteral vaccines are not effective at eliciting mucosal sIgA responses and are ineffective against bacteria that interact with mucosal surfaces and do not invade (e.g., *Vibrio cholerae*).

Oral immunization can be effective for induction of specific sIgA responses if the antigens are presented to the T and B lymphocytes and accessory cells contained within the Peyer's patches where preferential IgA B-cell development is initiated. The Peyer's patches contain helper T cells (TH) that mediate B-cell isotype switching directly from IgM cells to IgA B cells then migrate to the mesentric lymph nodes and undergo differentiation, enter the thoracic duct, then the general circulation, and subsequently seed all of the secretory tissues of the body, including the lamina propria of the gut and respiratory tract. IgA is then produced by the mature plasma cells, complexed with membrane-bound Secretory Component, and transported onto the mucosal surface where it is available to interact with invading pathogens. The existence of this common mucosal immune system explains in part the potential of live oral vaccines and oral immunization for protection against pathogenic organisms that initiate infection by first interacting with mucosal surfaces.

A number of strategies have been developed for oral immunization, including the use of attenuated mutants of bacteria (e.g., Salmonella spp.) as carriers of heterologous antigens, encapsulation of antigens into microspheres composed of poly-DL-lactide-glycolide (PGL), protein-like polymers-proteinoids, gelatin capsules, different formulations of liposomes, adsorption onto nanoparticles, use of lipophilic immune stimulating complexes, and addition of bacterial products with known adjuvant properties.

Underlying the development of most current vaccines is the ability to grow the disease causing agent in large quantities. At present, vaccines are usually produced from killed or live attenuated pathogens. If the pathogen is a virus, large amounts of the virus must be grown in an animal host or cultured animal cells. If a live attenuated virus is utilized, it must be clearly proven to lack virulence while retaining the ability to establish infection and induce humoral and cellular immunity. If a killed virus is utilized, the vaccine must demonstrate the lack of capacity of surviving antigens to induce immunization. Additionally, surface antigens, the major viral particles which induce immunity, may be isolated and administered to induce immunity in lieu of utilizing live attenuated or killed viruses.

Enteric bacterial diseases such as cholera, dysentery, *Escherichia coil* (*E. coli*) related diarrheas, and typhoid fever are major causes of morbidity and mortality worldwide, especially in developing countries where sanitation conditions are often less than adequate. Several types of vaccines against these enteropathies have been developed and tested over the years, among them killed whole cells, subunits of toxins, and live attenuated bacteria administered parenterally or orally. The majority of the morbidity and mortality due to bacterial diarrheal disease results from infections with V. cholerae and the cholera-related enterotoxic enteropathies (viz., *E. coli* that produce cholera-like enterotoxin).

*E. coli* cause diarrheal disease by a variety of mechanisms, including production of one or more 4 enterotoxins. One of these toxins, referred to as the heat-labile enterotoxin (LT), is immunologically and physicochemically related to the cholera enterotoxin. LT has been purified to homogeneity and has been extensively characterized. LT-B, a 56,000 dalton pentameric protein that consists of 5 identical monomeric subunits, functions as the binding component of the heat-labile enterotoxin. If administered parenterally, LT-B induces a serum response to itself and to haptens covalently linked to the molecule even in the absence of an adjuvant. Likewise, LT-B administered orally has been shown in both animal models and in human volunteers, to induce a serum IgG and mucosal IgA response to itself and to appropriately linked haptens.

The structure of LT has been well characterized by X-ray crystallography and consists of a multimeric protein. The holotoxin includes one 'A' subunit (LT-A) of molecular weight 27,000 Daltons which is cleaved into LT-A1 and LT-A2 by the proteases in the small bowel. The holotoxin also contains five 'B' subunits (LT-B), of molecular weight 11,600 Daltons each, that are noncovalently linked into a very stable doughnutlike pentamer structure.

The LT-B pentamer structure binds to intestinal epithelial cells via specific interactions with the GM-I ganglioside (galactosyl-N-acetylgalactosaminyl-(sialyl)-galactosylglucosyl ceramide) present on the cell surface. This facilitates the entry of toxic LT-A1 into cells, which contains the ADP ribosyl transferase activity. The LT toxin of enterotoxigenic *E. coli* (ETEC) is similar both structurally and functionally to CT, the cholera toxin of *Vibrio cholera*. Immunization against one has been seen to lead to cross protection against the other. J. D. Clemens, et al., *Lancet* 335, 270 (1990). The B subunit of cholera is an integral part of the candidate oral vaccine tested in Bangladesh. J. D. Clemens, et al., *Lancet* 335, 270 (1990).

Vaccine manufacturing often employs complex technologies entailing high costs for both the development and production of the vaccine. Concentration and rification of the vaccine is required, whether it is made from cell cultures, whole bacteria, viruses, other pathogenic organisms or subunits thereof. The high cost of purifying a vaccine in accordance with Food and Drug Administration (FDA) regulations makes most oral vaccines prohibitively expensive to produce because they require ten to fifty times more than the regular quality of vaccine per dose than a vaccine which is parenterally administered.

According to FDA guidelines, efficacy of vaccines for humans must be demonstrated in animals by antibody development and by resistance to infection and disease upon challenge with the pathogen. When the safety and immunogenicity level are satisfactory, FDA clinical studies are then conducted in humans. A small carefully controlled group of volunteers are enlisted from the general population to begin human trials. This long and expensive process of testing takes years before it can be determined whether the vaccine can be given to the general population. If the trials are successful, the vaccine may then be mass produced and sold to the public.

Even after these precautions, problems can and do arise. With killed bacterial cells, viruses or other pathogenic organisms, there is always a chance that live pathogens survive and vaccination may lead to isolated cases of the disease. Moreover, the vaccines may sometimes be contaminated with cellular material from the culture material from which it was derived. These contaminates can cause adverse reactions in the vaccine recipient and sometimes even death. Legal liability of the vaccine manufacturer for those who are harmed by an adverse reaction to vaccines requires the manufacturer to have and maintain expensive liability insurance which further adds to the ultimate cost of the vaccine.

Most pathogens enter on or through a mucosal surface, with exception of insect-borne pathogens or pathogens entering the body through wounds. Pathogens that enter, through mucosal surfaces include, without limitation, Actinomyces, Aeromonas, Bacillus, Bacteroides, Bordetella, Brucella, Compylobacter, Capnocylophaga, Clamydia, Clostridium, Corynebacterium, Eikenella, Erysipelothrix, Escherichia, Fusobacterium, Hemophilus, Klebsiella, Legionella, Leptospira, Listeria, Mycobacterium, Mycoplasma, Neisseria, Nocardia, Pasteurella, Proteus, Pseudomonas, Rickettsia, Salmonella, Selenomonas, Shigelia, Staphylococcus, Streptococcus, Treponema, Vibro, and Yersinia, pathogenic viral strains from the groups Adeiiovirus, Coronavirus, Herpesvirus, Orthomyxovirus, Picornovirus, Poxvirus, Reovirus, Retrovirus, and Rotavirus, pathogenic fungi from the genera Aspercillus, Blastomyces, Candida, Coccoidiodes, Cryptococcus Histoplasma and Phycomyces, and pathogenic parasites in the genera Eimeria, Entamoeba, and Trichomonas.

Mammalian hosts infected by a pathogen mount an immune response in an attempt to overcome the pathogen. The immune system consists of three branches: mucosal, humoral, and cellular. Mucosal immunity results from the production of secretory (sIgA) antibodies in secretions that bathe all mucosal surfaces including the respiratory tract, gastrointestinal tract, and the genitourinary tract and in secretions from all secretory glands. Secretory IgA antibodies prevent colonization of pathogens on the mucosal surfaces and are a first line of defense against colonization and invasion of a pathogen through the mucosal surfaces. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT).

Membranous microfold cells, otherwise known as M cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to T lymphocytes (in the case of T-dependent antigens), which process the antigen for presentation to committed B cells. B cells are then stimulated to proliferate, migrate, and ultimately transformed into antibody-secreting plasma cells producing IgA against the presented antigen.

When the antigen is taken up by M cells overlying the GALT and BALT, a generalized mucosal immunity results with sIgA against the antigen being produced by all secretory tissues in the body. Because most pathogens enter through mucosal surfaces and such surfaces make up the first line of defense to infection and facilitate the body's immune response, vaccines that can be orally administered represent a most important route to stimulating a generalized mucosal immune response leading to local stimulation of a secretory immune response in the oral cavity and in the gastrointestinal tract.

Secretory IgA antibodies directly inhibit the adherence of microorganisms to mucosal epithelial cells and to the teeth of the host. This inhibition may be the result of agglutination of microorganisms, reduction of hydrophobicity or negative charge, and blockage of microbial adhesions. These anti-adherence effects are amplified by other factors such as secretory glycoproteins, continuous desquamation of surface epithelium and floral competition.

Clinical experience with human peroral poliovirus vaccine and several peroral or intranasal virus vaccines applied in veterinary medicine shows that sIgA plays a decisive role in the protective effect by the mucosal immune system against respiratory and enteric viral infections. The effect of sIgA appears to be that of inhibiting the entry of viruses into host cells rather than prevention of attachment.

B. Plant Genetic Engineering

Various methods are known in the art to accomplish the genetic transformation of plants and plant tissues so that foreign DNA is introduced into the plant's genetic material in a stable manner, i.e., a manner that will allow the foreign DNA to be passed on the plant's progeny. Two such transforming procedures are Agrobacterium-mediated transformation and direct gene transfer.

Agrobacterium-mediated transformation utilizes *A. tumefaciens*, the etiologic agent of crown gall, a disease of a wide range of dicotyledons and gymnosperms that results in the formation of tumors or galls in plant tissue at the site of infection. Agrobacterium, which normally infects the plant at wound sites, carries a large extrachromosomal element called Ti (tumor-inducing) plasmid.

Ti plasmids contain two regions required for tumor induction. One region is the T-DNA (transferred-DNA) which is the DNA sequence that is ultimately found stably transferred to plant genomic DNA. The other region is the vir (virulence) region which has been implicated in the transfer mechanism. Although the vir region is absolutely required for stable transformation, the vir DNA is not actually transferred to the infected plant. Transformation of plant cells mediated by infection with *A. tumefaciens* and subsequent transfer of the T-DNA alone have been well documented. See, e.g., Bevan, M. W. et al., *Int. Rev. Genet*, 16, 357 (1982).

After several years of intense research in many laboratories, the Agrobacterium system has been developed to permit routine transformation of a variety of plant tissues. Representative tissues transformed by this technique include, but are not limited to, tobacco, tomato, sunflower, cotton, rapeseed, potato, poplar, and soybean.

*A. rhizogenes* has also been used as a vector for plant transformation. That bacterium, which incites root hair formation in many dicotyledonous plant species, carries a large extrachromosomal element called a Ri (root-inducing) plasmid which functions in a manner analogous to the Ti plasmid of *A. tumefaciens*. Transformation using *A. rhizogenes* has developed analogously to that of *A. tumefaciens* and has been successfully utilized to transform plants which include but are not limited to alfalfa and poplar.

In the case of direct gene transfer, foreign genetic material is transformed into plant tissue without the use of the agrobacterium plasmids. Direct transformation involves the uptake of exogenous genetic material into plant cells or protoplagtg. Such uptake may be enhanced by use of chemical agents or electric fields. The exogenous material may then be integrated into the nuclear genome. The early work with direct transfer was conducted in the dicot Nicotiana tobacum (tobacco) where it was shown that the foreign DNA was incorporated and transmitted to progeny plants. Several monocot protoplasts have also been transformed by this procedure including maize and rice.

Liposome fusion has also been shown to be a method for transforming plant cells. Protoplasts are brought together with liposomes carrying the desired gene. As membranes merge, the foreign gene is transferred to the protoplact.

In addition, direct gene transfer can be accomplished by polyethylene glycol (PEG) mediated transformation. PEG mediated transformation has been successfully used to transform dicots such as tobacco and monocots such as lolium multiflorum. This method relies on chemicals to mediate the DNA uptake by protoplasts and is based on synergistic interactions between $Mg^{+2}$, PEG, and possibly $Ca^{+2}$. See, e.g., Negrutiu, R. et al., *Plant Mol. Biol.*, 8, 363 (1987).

Alternatively, exogenous DNA can be introduced into cells or protoplasts by microinjection. In this technique, a solution of the plasmid DNA or DNA fragment is injected directly into the cell with a finely pulled glass needle. This technique has been used to transform alfalfa.

A more recently developed procedure for direct gene transfer involves bombardment of cells by micro-projectiles carrying DNA. In this procedure, commonly called particle bombardment, tungsten or gold particles coated with the exogenous DNA are accelerated toward the target cells. The particles penetrate the cells carrying with them the coated DNA. Microparticle acceleration has been successfully demonstrated to lead to both transient expression and stable expression in cells suspended in cultures, protoplasts, immature embryos of plants including but not limited to onion, maize, soybean, and tobacco.

Once plant cells have been transformed, there are a variety of methods for regenerating plants. The particular method of regeneration will depend on the starting plant tissue and the particular plant species to be regenerated. In recent years, it has become possible to regenerate many species of plants from callus tissue derived from plant explants. The plants which can be regenerated from callus include monocots, such as but not limited to corn, rice, barley, wheat, and rye, and dicots, such as but not limited as to sunflower, soybean, cotton, rapeseed and tobacco.

Regeneration of plants from tissue transformed with *A. tumefaciens* has been demonstrated for several species of plants. These include but is not limited to sunflower, tomato, white clover, rapeseed, cotton, tobacco, potato, maize, rice, and numerous vegetable crops.

Plant regeneration from protoplasts is occasionally a useful technique. When a plant species can be regenerated from protoplasts, then direct gene transfer procedures can be utilized, and transformation is not dependent on the use of *A. tumefaciens*. Regeneration of plants from protoplasts has been demonstrated for plants including but not limited to tobacco, potato, poplar, corn, and soybean.

The technology developed for the creation of transgenic plants has led many investigators to study the expression of genes derived from dissimilar plant species or from non-plant genomes. In many cases, it has been desirable to characterize the expression of recombinant proteins encoded by genes derived from viruses or bacteria. The construction of chimeric genes for expression of foreign coding sequences in plants involves ligation of non-coding regulatory elements which function in plants 5' to the DNA sequence encoding the desired protein, and ligation of a polyadenylation signal which is active in plant cells 3' to the DNA sequence encoding the desired protein.

The 5' regulatory sequences which are often used in creation of chimeric genes for plant transformation may cause either nominally constitutive expression in all cells of the transgenic plant, or regulated gene expression where only specific cells or tissues show expression of the introduced genes. The CaMV 35-S promoter, which was derived from the Cauliflower Mosaic Virus which causes a plant disease, has frequently been used to drive nominally constitutive expression of foreign genes in plants. A eregulatory DNA element which was found to control the tuber-specific expression of the patatin protein is an example of developmentally specific gene expression; this patatin promoter element is known to cause the tuber-specific expression of at least some foreign genes. see, e.g., H. C. Wenzler, G. A. Mignery, L. M. Fisher, W. D. Park, *Plant Mol. Biol.*, 12:41–50 (1989).

Chimeric gene constructions may also include modifications of the amino acid coding sequence of the structural gene being introduced into transgenic plants. For example, it may be desirable to add or delete amino acids in the protein to be expressed to influence the cellular localization of foreign gene product in the cells of transgenic plants.

It has been shown that the inclusion of KDEL and HDEL amino acid sequences at the carboxy terminus of at least one protein enhanced the recognition for that protein by the plant endoplasmic reticulum retention machinery. S. Munro and H. R. B. Pelham, *Cell* 48, 988–997 (1987); J. Denecke, R. DeRycke, J. Botterman, EMBO-J. 11, 2345 (1992); E. M. Herman, B. W. Tague, L. M. Hoffman, S. E. Kjemtrip, M. J. Chrispeels, *Planta* 182, 305 (1991); C. Wandelt, et al., The *Plant Journal* 2, 181 (1992). However, such modifications are problematic at best because other factors such as protein conformation or protein folding in the transformed cells may interfere with the availability of this carboxy terminus signal by the plant endoplasmic reticulum retention machinery. S. M. Haugejorden, M. Srinivasan, M. Green, *J-Biol-Chem.* 266, 6015 (1991).

C. Oral Vaccine Methodologies using Transgenic Plants

There are four well-known genetic expression transformation systems that can be used for producing transgenic plants capable of being administered as one of the active agents in oral vaccines against a desired antigen. The present invention takes advantage of all four of these expression systems for the construction of edible vaccines. It should be recognized that this list is not meant to exhaust other possible approaches. The list is simply included to provide a proper context for the scope and teaching of the present invention.

First, in trdnsgenic plants, expression vectors including the CaMV 35S promoter and antigen coding sequences can be used to constitutively transform the plants where expression in the leaves allows for rapid analysis of gene expression and biochemical characterization of gene products.

In such plants such as but not limited to *Brassica napus* (canola), expression vectors including the 2S albumin promoter and antigen coding sequences can be used to cause seed-specific gene expression to create the production of recombinant protein in seed tissues, routinely used as animal feed, providing for the production of attractive oral immunogenicity analyses.

In plants such as but not limited to *Solanum tuberosum* (potato), expression vectors including the patatin promoter or soybean vspB promoter and antigen coding sequences can be used to cause tuber-specific gene expression to create tuber-specific production of recombinant protein in tuber tissues routinely used as food. Thin provides for the production of attractive oral immunogenicity analyses.

Finally, in plants such as but not limited to *Musa acuminata* (banana), expression vectors including fruit ripening-specific promoters and antigen coding sequences can be used to transform plants that produce the recombinant protein in ripened fruit where production of recombinant protein is produced directly as candidate vaccines for ingestion studies in animals and humans.

The retention of biological properties in the recombinant proteins produced in plants, specifically ligand binding and the presentation of antigenic epitopes, is of considerable importance to the successful production of edible vaccines in transgenic plants. The ultimate test of the value of proteins of pharmacological importance is their biological activity. Vaccines are of particular interest for studies of protein expression since their effects can be accurately quantified in animal models, In addition, relatively low amounts are required, since their effects are amplified by the immune system.

The high cost of production and purification of synthetic peptides manufactured by chemical or fermentation based processes may prevent their broad scale use as oral vaccines.

The production of immunogenic proteins in transgenic plants and the adjuvant effect of such proteins in transgenic plants offers an economical alternative.

While oral vaccines may be an effective and inexpensive procedure for inducing secretory immune responses in animals including humans, there is a need for proven techniques that yield tranzgenic plants or plant tissues that can, upon direct ingestion, cause a desired immune response to a given antigen without significant side effects.

Attempts to produce transgenic plants expressing bacterial antigens of *E. Coli* and of Streptococcus mutans have been made. Curtiss and Ihnen, WO 90/0248, published Mar. 22, 1990. Transgenic plants which express the Hepatitis B surface antigen (HBsAg) have also been made. H. S. Mason, D. M-K. Lam, C. J. Arntzen, *Proc. Natl. Acad. Sci. USA*, 89:11745–749 (1992).

However, those studies have not yielded orally immunogenic plant material nor have they demonstrated that it is, in fact, possible to orally immunize animals with antigens produced in transgenic plants. In fact, it took the significant and unexpected improvements disclosed herein, to successfully demonstrate that it is indeed possible to actually immunize animals against antigens by feeding animals transgenic plants in which sufficient levels of the antigen have been expressed in order to induce immunity. In addition, it took the significant and unexpected improvements of the instant invention to also demonstrate the adjuvant effect toward other immunogens caused by immunizing animals with transgenic plants containing bacterial toxin antigens.

The present discovery described in the following sections discloses how to overcome the previous limitations by the significant and unexpected improvements of causing the production of increased levels of the antigenic protein and by compartmentalization in microsomal vesicles of transgenic plants of an orally active LT-B protein which is highly immunogenic, and by the increased expression of such transgenic bacterial antigens in plants through i) alterations in the plant promoters to increase the level of expression of transgenic proteins in plants, ii) alteration of 3' messages and polyadenylation signals to increase the production of trantgetic proteins in plants and iii) production of synthetic genes encoding bacterial antigens where the codon usage has been changed to increase the usage by plants thus increasing the level of transgenic proteins produced in plants. Further, the present discovery discloses that the compartmentalized foreign protein expression in edible transgenic plant tissues allows expression and delivery of additional, desired antigens of value as oral vaccines, since the microsome-encapsulated LT-B serves as an oral adjuvant.

SUMMARY OF THE INVENTION

In order to provide a clear and consistent understanding of the present invention, the following list of terms and their definitions are provided.

An animal is any vertibrate or invertebrate, including, but not limited to humans, birds and fish.

An antigen is a macromolecule that is capable of stimulating the production of antibodies upon introduction into a mammal or other animal including humans. As used in this application, antigen means an antigen per se, an antigenic determinant or the antigen, or a fusion protein containing the antigen or antigenic determinant sometimeing referred to a native epitopes.

An antigenic determinant is a small chemical complex that determines the specificity of an antigen-antibody reaction colonization and/or virulence antigens of a pathogen contain one or more antigenic determinants.

An amino acid domain is an amino acid sequence within a protein that can be associated with a particular function or sequence homology.

A colonization or virulence antigen is an antigen on the surface of a pathogenic microorganism that is associated with the ability of the microorganism to colonize or invade its host. Discussion and claims may refer to colonization or virulence antigens or antigenic determinants thereof. A pathogen may contain antigens of either colonization or virulence or both and one or more DNA sequences for each or both may be transferred to a vector and used to transform a plant such that it expresses the antigen or antigens.

An immunogenic agent is any antigen that is capable of causing an immune response in animals such as upon oral ingestion of plants carrying vectors that express the antigen.

A chimeric sequence or gene is a DNA sequence containing at least two heterologous parts, i.e., parts derived from, or having substantial sequence homology to pre-existing DNA sequences which are not associated in their pre-existing states. The pre-existing DNA sequences may be of natural or synthetic origin.

A coding DNA sequence is a DNA sequence from which the information for making a peptide molecule, mRNA or tRNA are transcribed. A DNA sequence may be a gene, combination of genes, or a gene fragment.

A foreign DNA is a DNA that is exogenous to or not naturally found in the microorganisms or plants to be transformed. Such foreign DNA includes viral, prokaryotic, and eukaryotic DNA, and may be naturally occurring, chemically synthesized, cDNA, mutated, or any combination of such DNAs. The foreign DNA of this invention is derived from or has substantial sequence homology to DNA of pathogenic microorganisms and viruses, or is a synthetic gene which encodes a protein which is of similar amino acid sequence to prokaryotic genes.

A fusion protein is a protein containing at least two different amino acid sequences linked in a polypeptide where the sequences were not natively expressed as a single protein. Fusion proteins are frequently the result of genetic engineering whereby DNA sequences from different genes are joined together to encode a single protein composed of amino acid sequence from the originally separate genes.

A gene is a discrete chromosomal region that codes for a discrete cellular product.

An LT-B containing protein is any protein that is substantially homologous in amino acid sequence to, or substantially functionally similar to bacterially derived LT-B protein or CT-B protein. LT-B containing proteins include, but are not limited to proteins with at least one domain with at least about 90% amino acid sequence homology with bacterially derived LT-B or CT-B proteins, proteins that are substantially functionally similar to bacterially derived LT-B or CT-B proteins in binding to GM I gangliosides, and protein fusions in which domains that are substantially similar to bacterially derived LT-B or CT-B are fused to other amino acid sequences either at the N or C terminus of the other amino acid sequences, or fused within the other amino acid sequences.

An LT-A containing protein is any protein that is substantially homologous in amino acid sequence to, or substantially functionally similar to the bacterially derived LT-A protein. LT-A containing proteins include, but are not limited to proteins with at least one domain with at least about 90% amino acid sequence homology with bacterially derived LT-A, and proteins that are substantially functionally similar to bacterially derived LT-A.

A microorganism is a member of one of the following classes: bacteria, fungi, protozoa, or viruses.

A plant tissue is any tissue of a plant in its native state or in culture. This term includes, without limitation, whole plants, plant cells, plant organs, plant seeds, protoplasts, callus, cell cultures, and any group of plant cells organized into structural and/or functional units. The use of this term in conjunction with, or in the absence of, any specific type to plant tissue as listed above or otherwise embraced by this definition is not intended to be exclusive of any other type of plant tissue. Plants suitable for transformation according to the processes of this invention included, without limitation, monocots such as corn, wheat, barley, sorghum, rye, rice, banana, and plantains, and dicots such as potato, tomato, alfalfa, soybean, beans in general, canola, apple, pears, fruits in general, and other vegetables.

A plant transformation vector is a plasmid or viral vector that is capable of transforming plant tissue such that the plant tissue contains and expresses DNA not pre-existing in the plant tissue.

A food stuff or edible plant material is any plant material that can be directly ingested by animals or humans as a nutritional source or dietary complement.

A pre-existing DNA sequence is a DNA sequence that exits prior to its use, in toto or in part, in a product of method according to this invention. While such pre-existence typically reflects a natural origin, pre-existing sequences may be of synthetic or other origin.

An immune response involves the production of antibodies, which are proteins called immunoglobulins. The antibodies circulate in the bloodstream and permeate the other body fluids, where they bind specifically to the type of foreign antigen that induced them. Binding by antibody inactivates viruses and bacterial toxins (such as tetanus or botulinum toxin) frequently by blocking their ability to bind to receptors on target cells. Antibody binding also marks invading microorganisms for destruction, either by making it easier for a phagocytic cell to ingest them or by activating a system of blood proteins, collectively called complement, that kills the invaders. Cell-mediated immune responses, the second class of immune responses, involve the production of specialized cells that react with foreign antigens on the surface of other host cells. The reacting cell can kill a virus-infected host cell that has viral proteins on its surface, thereby eliminating the infected cell before the virus has replicated. In other cases the reacting cell secretes chemical signals that activate macrophages to destroy invading microorganisms.

A secretory immune response (SIR) is a specific type of immune response. It involves the formation and production of secretory IgA antibodies in secretions that bathe the mucosal surfaces of human and other animals and in secretions from secretory glands. An agent which causes the formation and production of such antibodies is considered to stimulate secretory immunity or to elicit a SIR. Secretory immunity is also sometimes referred to as mucosal immunity.

A substantial sequence homology is a functional and/or structural equivalence between sequences of nucleotides or amino acids. Functional and/or structural differences between sequences having substantial sequence homology is frequently de minimus A transgenic plant is a plant that contains and expresses DNA that was not pre-existing in the plant prior to the introduction of the DNA into the plant.

Transgenic plant material is any plant matter, including, but not limited to cells, protoplasts, tissues, leaves, stems, fruit and tubers both natural and processed, containing and expressing DNA that was not pre-existing in the plant prior to the introduction of the DNA into the plant. Further, plant material includes processed derivatives thereof including, but not limited to food products, food stuffs, food supplements, extracts, concentrates, pills, lozengens, chewable compositions, powders, formulas, suryps, candies, wafers, capsules and tablets.

An edible plant material includes a plant or any material obtained from a plant which is suitable for ingestion by mammal or other animals including humans. This term is intended to include raw plant material that may be fed directly to animals or any processed plant material that is fed to animals, including humans. Materials obtained from a plant are intended to include any component of a plant which is eventually ingested by a human or other animal.

An endoplasmic reticulum (ER) retention sequence is any DNA sequence that codes for an amino acid sequence known to result in the retention of a given protein at or associated with the endoplasmic reticulum such as DNA sequences coding for the amino acids KDEL, HDEL, SEKDEL, and SEHDEL.

An ER signal sequence is any DNA sequence that codes for an amino acid sequence known to result in the recognition of a given protein by the signal recognition particle on the endoplasmic reticulum resulting in the localization of the protein within the ER. Examples of signal sequences which direct newly synthesized proteins to the endoplasmic reticulum in plant cells include barley lectin (Dombrowski J E, Schroeder M R, Bednarek S Y, Raikhel NV, 1993, *Plant Cell* 5:587–596), barley aleurain (Holwerda B C, Padgett H S, Rogers J C, 1992, *Plant Cell* 4:307–318), sweet potato sporamin (Matsuoka K, Nakamura K, 1991, *Proc. Natl. Acad. Sci. USA* 88:834–838), patatin (Sonnewald U, Braur M, von Schaewen A, Stitt M, Willmitzer L, 1991, Plant J. 1:95–106), soybean vegetative storage proteins (Mason H S, Guerrero F, Boyer J, Mullet J, 1988, *Plant Mol. Biol.* 11:845–856), and β-fructosidase (Faye L, Chrispeels M J, 1989, *Plant Physiol.* 89:845–851).

A LT holotoxin is a protein complex produced by enterotoxic *E. coli* or by transgenic organisms containing the gene for LT-A and LT-B, such as the enterotoxin itself or proteins that contain replacement codons to facilitate plant transcription through the replacement of bacterial preferred amino acid codons for plant preferred amino acid codons.

A CT holotoxin is a protein complex produced by *V. cholerae* or by transgenic organisms containing the gene for CT-A and CT-B, such as the cholera toxin itself or proteins that contain replacement codons to facilitate plant transcription through the replacement of bacterial A and T rich preferred mino acid codons for plant preferred amino acid codons.

An LT fusion protein is a protein where portions of either the LT-A sub unit or the LT-B subunit or both subunits of the LT toxin have been modified to include coding regions for amino acid sequences derived from other antilenic proteins or synthetic proteins or other synthetic molecules designed mimic the immunogenic response of other antigenic proteins or agents. A CT fusion protein is analogously defined except that the fusions occur on either one or both of the CT subunits. Preferred fusion proteins are those fusions to the LT-B or CT-B subunit that do not interfere with the LT-B or CT-B subunit oligomerization into pentamer and/or LT-A or CT-A fusions that preserve that portion of the LT-A or CT-A protein that associates with the pentameric B subunit to form the intact holotoxin in the unmodified form.

The present invention provides an edible vaccine comprising a transgenic plant comprising or expressing at least a DNA sequence encoding an LT-B or CT-D containing protein where the vaccine is designed to elicit immune responses in animals including humans. This invention also provides transgenic plants comprising or expressing at least a DNA sequence encoding an LT-B or a CT-B containing protein which can be used to produce vaccines with enhanced immune responses in animals. The transgenic plants of this invention are especially designed as vaccines or vaccine adjuvants for oral administration and stimulation of immune responses in the GALT of animals including humans.

The present invention also provides a transgenic plant capable of enhancing the immune responses to antigens where the transgenic plant comprises or expresses a DNA sequence encoding an LT-B or a CT-B containing protein. The transgenic plants may also include genetic elements encoding other desired antigens capable of eliciting a secretory immune response in animals. Such other antigens, when presented with transgenic plants containing adjuvantic bacterial toxin antigens can further be enhanced in their immunogenicity via the adjuvant effect of the plant-produced transgenic bacterial toxin antigens.

The present invention also provides for methods for administering the vaccines of this invention, methods for producing the vaccines of the present invention, and methods for preparing the transgenic plants of this invention. This includes the significant and unexpected improvements of causing the production of increased levels of the antigenic protein and by compartmentalization in microsomal vesicles of transgenic plants of an orally active LT-B protein which is highly immunogenic, and by the increased expression of such transgenic bacterial antigens in plants through i) alterations in the plant promoters to increase the level of expression of transgenic proteins in plants, ii) alteration of 3' messages and polyadenylation signals to increase the production of transgenic proteins in plants and iii) production of synthetic genes encoding bacterial antigens where the codon usage has been changed to increase the usage by plants thus increasing the level of transgenic proteins produced in plants. Further, this includes the instant and unexpected discovery that the compartmentalized foreign protein expression in edible transgenic plant tissues allows expression and delivery of additional, desired antigens of value as oral vaccines, since the microsome-encapsulated LT-B serves as an oral adjuvant.

The method for preparing the transgenic plants of this invention includes transforming a target plant with a plant transformation vector containing at least a DNA sequence that codes for a LT-B or a CT-B containing protein. The DNA sequence m also contain DNA elements coding for one or more colonization antigens, a virulence antigens, or a antigenic determinant of virulence or colonization antigen of pathogenic microorganisms.

This invention further provides for plant transformation vectors capable of stable incorporation of at least an LT-B or CT-B containing protein gene and promoter regions into target plants. The transformation vectors are prepared by inserting a DNA sequence coding for an LT-B or CT-B containing protein and, optionally, for one or more DNA sequences coding for other antigens where the LT-B or CT-B gene acts as an oral adjuvant and is designed to enhance immune responses to the optionally expressed antigen. The DNA sequences may be natural or synthetic and may comprise entire genes or fragments of genes which code for antigens. Additionally, the DNA sequences may contain plant functional p promoters and genetic tags designed to make identification and selection of the transformed plant cells easier, and sequences for selected compartmentalization in desired plant tissues or cellular constituents.

The present invention also provides for transgenic plants usable as oral vaccines or oral vaccine adjuvants wherein the plants comprise or express a DNA sequence encoding an LT-B or CT-B containing protein, sequences encoding proteins containing components of LT-A or CT-A or protein components of LT-A or CT-A, and sequences encoding cellular signal and retention polypeptides or proteins, where the LT-B, CT-B, LT-A, and/or CT-A proteins may include fusions of other antigenic agents. Additionally, the DNA sequence can include encoding elements for the coordinate expression of other non-LT or non-CT antigens. Further, the present invention also provides for the coexpression and/or coprovision of other antigens, such as viral antigens, along with LT-B antigen such that the additional antigens can benefit from the adjuvant effect of the transgenic LT-B. In addition, the present invention provides for the coexpression of both the LT-A and LT-B subunits such that the holotoxin can be assembled in the plant tissue to act as both an immunogen and an adjuvant.

The present invention also provides for a food composition useful for eliciting immune responses comprising a transgenic plant or material derived from the plant. The food composition can include the transgenic plant itself, processed food products of the plant, nutrients, vitamins, coloring, and/or flavoring.

BRIEF DESCRIPTION OF THE FIGURES

FIGS. 1A, 1B, and 1C depict the structure of vectors pLTBI40, pLTKI10, and pLTB110, respectively;

FIGS. 2(A–B) depicts ELISA levels of recombinant LT-B and LT-B-SEKDEL proteins in soluble extracts from transgenic tobacco and potato plants transformed with the vectors pLTB110 and pLTK110;

FIG. 3 depicts radioactively labeled LT-B and LT-B-SEKDEL (labeled LT-B-KDEL in the figure) immunoprecipitates from leaf extracts from transgenic tobacco transformed with the vectors pLTB110 an pLTK110;

FIG. 4 depicts a size exclusion chromatogram of the LT-B-SEKDEL proteins for transgenic tobacco leaves;

FIGS. 5(A–B) depicts immunogenicity of transgenic tobacco leaf extracts (labeled LT-B-KDEL in figure) when fed orally to Balb/c mice;

FIG. 6 depicts immune response in mice fed LT-B-SEKDEL (labeled 110–1, 110–3, 110–4, and 110–7 in the figure) expressing potato tubers;

FIG. 7 depicts non-coding regulatory elements of vectors which can be used to transform plants and lead to the production of the LT-B protein in the resulting plants;

FIG. 8 depicts potato microtubers of transformed potato plants;

FIG. 9 depicts potato tubers obtained from selected transformants carrying the pLTB110 and pLTK110 vectors;

FIG. 10 depicts detection of mRNA encoding LT-A and LT-B in transformants carrying the pLT100 and pLT101;

FIG. 11 depicts the structure of pLTB120, LT102, LT103, LT104, LT105 and LTK140;

FIG. 12 depicts the synthetic oligonucleotides segments, A1–A4, used to create the synthetic LT-B gene;

FIG. 13 depicts the process of the creation of the A set of fragments used to create the synthetic LT-B gene;

DETAILED DESCRIPTION OF THE INVENTION

Figure 1A:
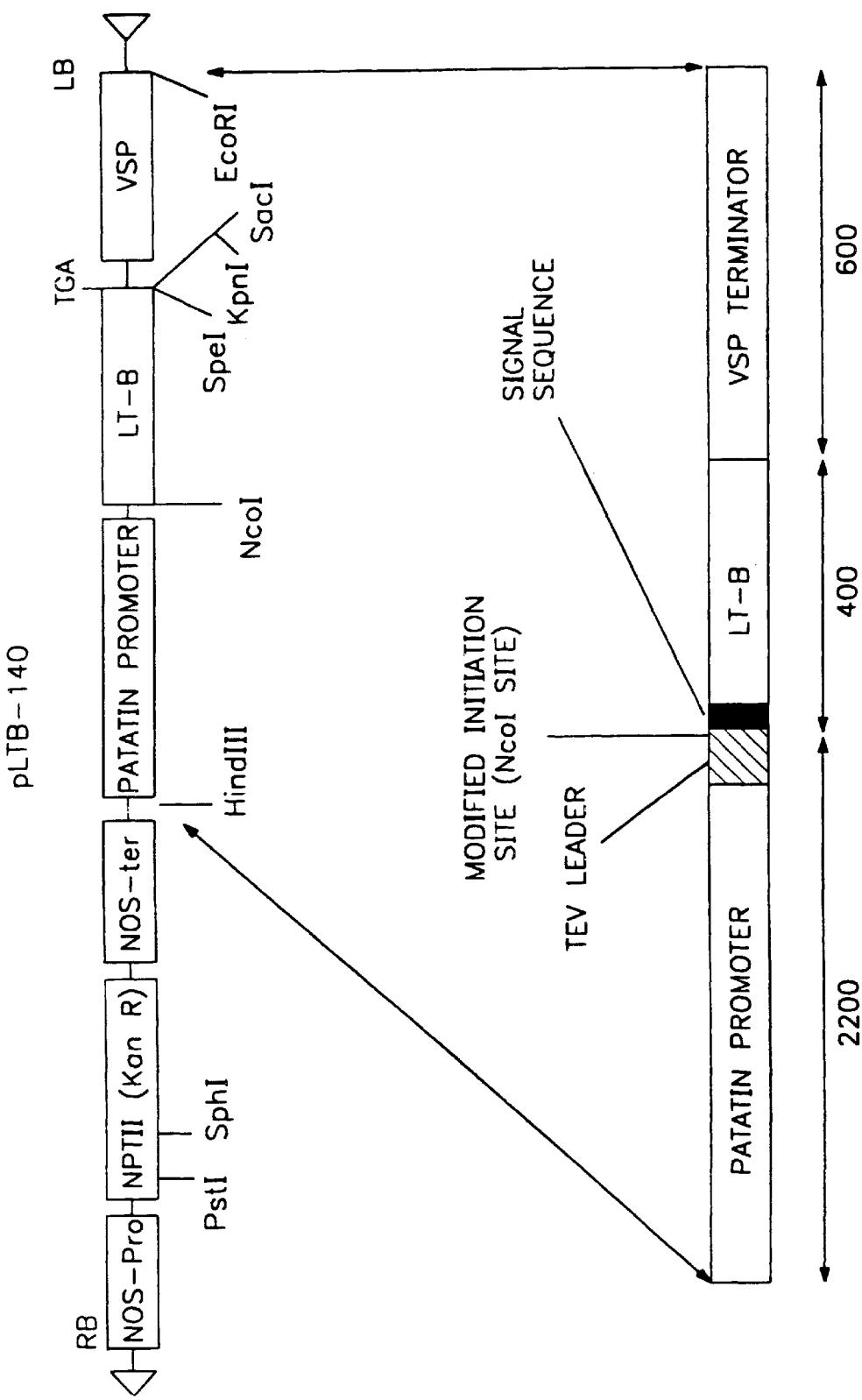
Figure 1B:
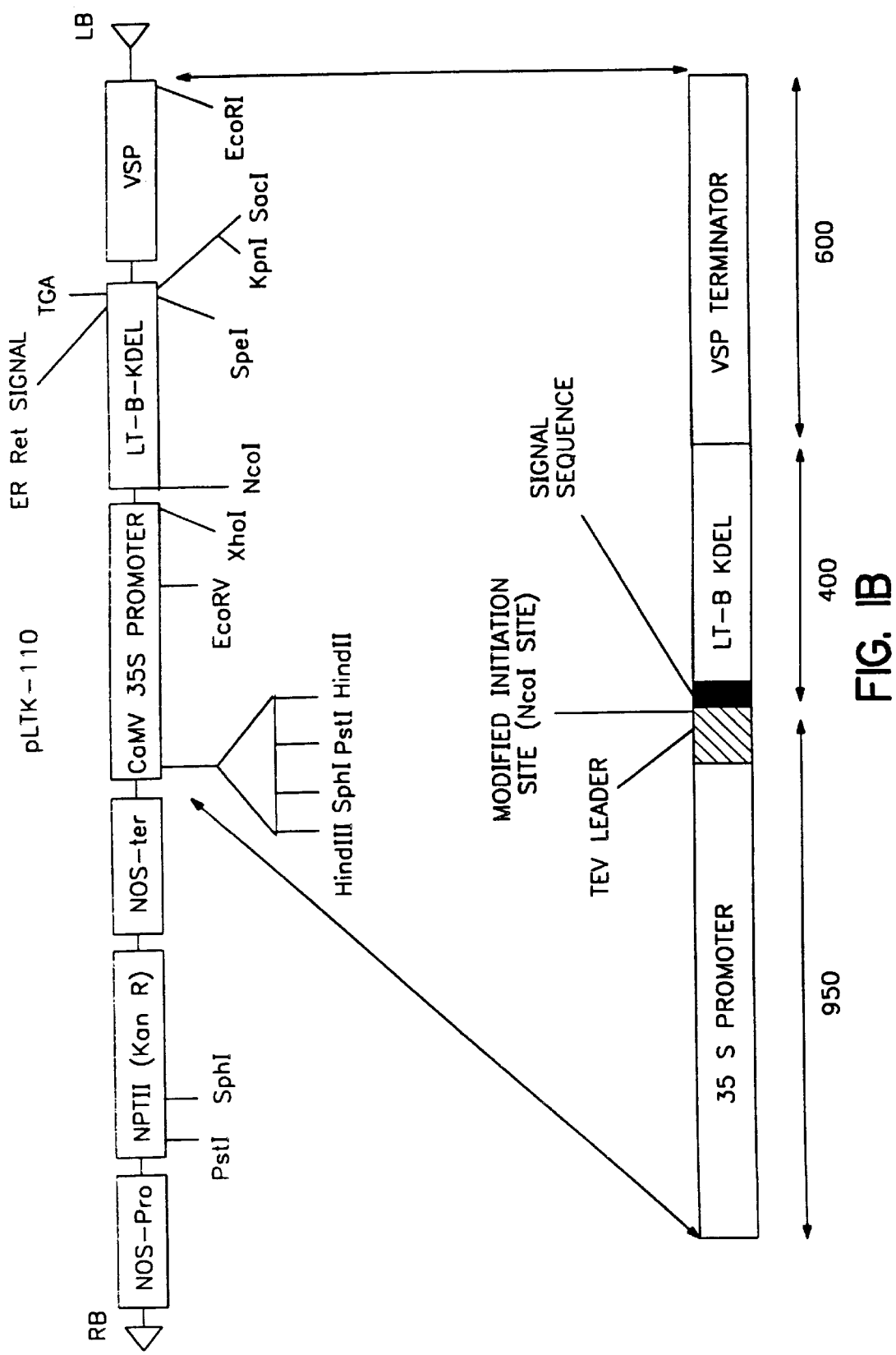
Figure 1C:
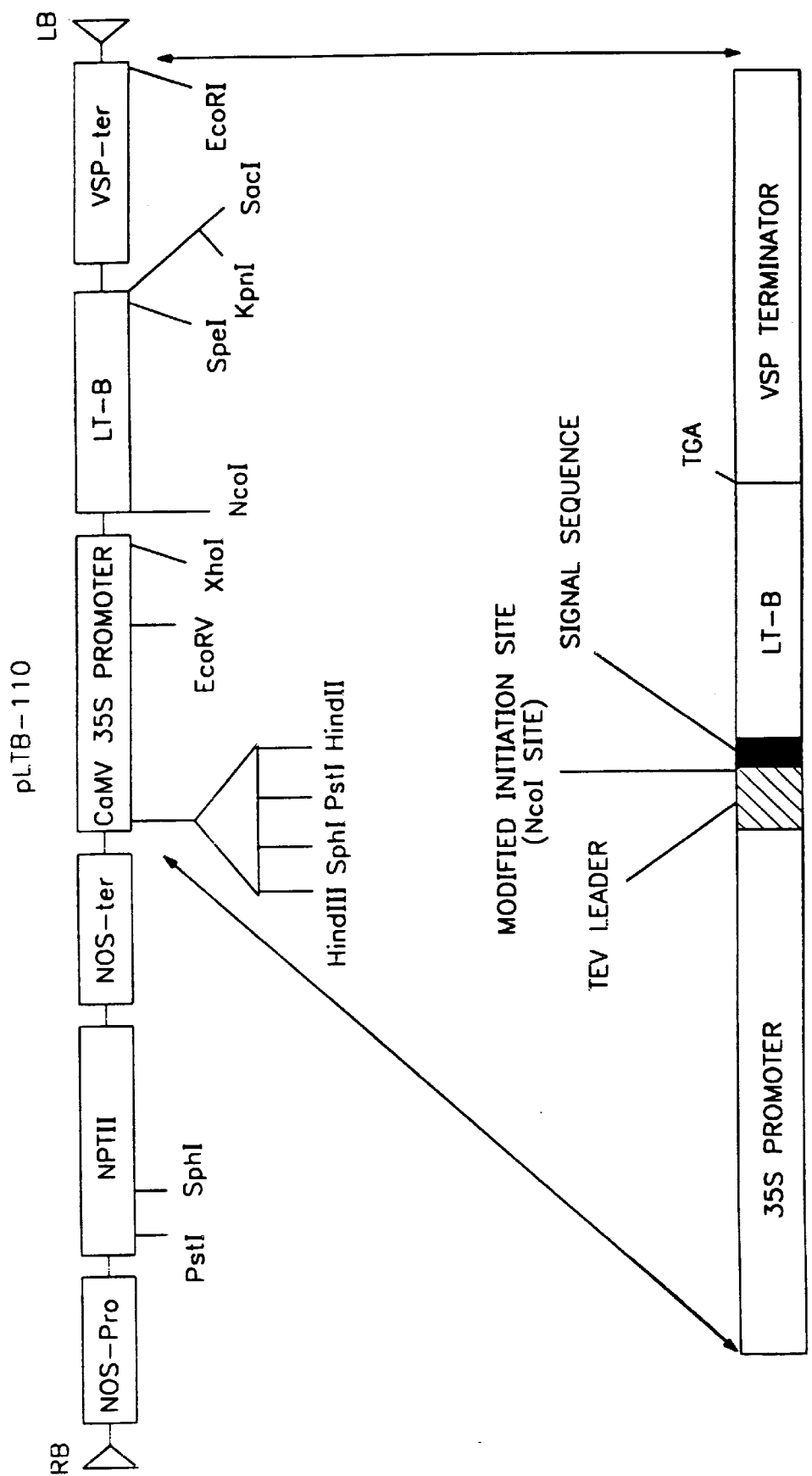

The feasibility of providing vaccines through the oral route has been described for prevention of diarrhea caused by bacteria. M. Lebens, S. Johansson, J. Osek, M. Lindbald, J. Holingren, *Bio/Technology*, 11:1574–578 (1993). Stimulation of the GALT with an antigen can lead to the development of protective antibody responses in the gut and at other mucosal sites.

In comparison to parenteral immunizations, oral immunization with nonviable antigens is often ineffective in stimulating an immune response and usually requires large amounts of antigen (mg vs. ug in parenteral) to produce an immune response. Thus, current oral subunit vaccine candidates being evaluated will require large scale fermentors and stringent purification protocols to obtain sufficient amounts of recombinant protein for oral delivery. These factors will be an important Congideration in manufacturing costs.

The B subunit pentamer of cholera toxin (CT-B) is capable of attaching to the GM-1 ganglioside of the intestinal epithelium and causing translocation across the epithelial membrane in the same manner as the *E. coli* heat labile enterotoxin (LT-B). Thus, it is expected that either CT-B or LT-B toxin when administered orally with an antigen will also serve as an adjuvant to enhance the protective immune response by acting as a "pilot" or "triggering" protein in eliciting a local immune response.

The present invention is directed to the perfection and enablement of oral vaccines using transgenic plants. Unlike the prior art, the instant invention presents the unexpected improvements that are both novel and necessary in order to immunize via transgenic plants. Unlike the prior art, the inventors have herein for the first time demonstrated that transgenic plants which express candidate oral vaccine antigens in their edible tissue can be fed to animals to cause production of antigens which demonstrate specific humoral and mucosal immune response. Further, for the first time the inventors have addressed the issue of the use of transgenic bacterial antigens not only as immunogens for themselves, but also as adjuvants for additional immunogens. The inventors believe that transgenic plants expressing antigenic proteins will constitute an inexpensive production and delivery system for such antigens to animals.

The present invention critically demonstrates and evaluates this concept by expressing a gene encoding a bacterial antigen in transgenic plants. Enterotoxigenic *Escherichia coli* (ETEC) is a well recognized etiologic agent of acute watery diarrhea which affects people of all ages. The pathogenicity of ETEC is by colonization of the small intestine and synthesis of one or more enterotoxins, one of which is the heat labile enterotoxin (LT). The LT holotoxin consists of a pentamer of binding (LT-B) subunits and an enzymatically active (LT-A) subunit.

The inventors have successfully demonstrated that DNA encoding LT-B with a C-terminus SEKDEL andoplasmic reticulum (ER) retention sequence substantially increases the amount of LT-B and LT-B pentamer in the transformed plant cells. Further, the inventors have demonstrated the unexpected improvement that the expression of transgenic bacterial antigens in plants can be increased to levels sufficient for them to act as both immunogens and adjuvants through i) alterations in the plant promoters to increase the level of expression of transgenic proteins in plants, ii) alteration of 3' messages and polyadenylation signals to increase the production of transgenic proteins in plants and iii) production of synthetic genes encoding bacterial antigens where the codon usage has been changed to increase the usage by plants thus increasing the level of transgenic proteins produced in plants. The inventors believe that the increased levels of LT-B pentamer in the microsomal vesicles of transgenic cells themselves is a preferred method for inducing a secretory immune response in animals fed such transgenic plant cells. In an analogous fashion, plants can be transformed with DNA encoding the cholera toxin B subunit (CT-B) as a chimeric gene including the SEKDEL coding sequence.

The inventors have found that vaccines capable of eliciting secretory immune responses in animals can be prepared from transgenicplants comprising and expressing at least a DNA sequence encoding an LT-B containing protein where the LT-B containing protein is expressed in sufficient amounts to induce pentamer formation in the cell. A digestible composition derived from transgenic plants expressing an LT-D containing protein when ingested by mice causes an immune response which causes them to produce immunoglobin that neutralize the LT.

In one preferred embodiment, and unexpected improvement over the prior art, the inventors have found that including a DNA segment which encodes additional amino acids at the C-terminus of the LT-B sequence that codes for an endoplasmic reticulum (ER) retention sequence results in transgenic plants that retain enhanced concentrations of the LT-B containing protein inside the cell in pentamer form in vesicles that recycle to the ER. The preferred ER retention sequences include DNA coding for KDEL (Lys-Asp-GIU-Leu) (SEQ ID NO: 1) (all sequences are summarized on the accompanying Sequence Listing, a copy of which is also being submitted on a computer readable disk), HDEL (His-Asp-Glu-Leu) (SEQ ID NO: 2), SEKDEL (Ser-Glu-Lys-Asp-Glu-Leu) (SEQ ID NO: 3), and SEHDEL (Ser-Glu-His-Asp-Glu-Leu) (SEQ ID NO: 4) where SEKDEL and SEHDEL are particularly preferred. The inventors fully expect the same behavior in transgenic plants transformed with CT-B genes, and indeed with any genes having the same C-terminus modifications.

Additionally, the present invention relates to transgenic plants that can be produced through the stable or transient incorporation of DNA encoding an LT-B or CT-B containing protein where the protein contains an LT-B or CT-D sequence, a N-terminus ER signal sequence, and a C-terminus ER retention sequence. These transformants show enhanced production of the LT-B or CT-B protein with concurrent retention of the proteins in vesicles in the cell. The inventors have also found that the preferred transformants are those that have LT-B pentamers which are retained in the cellular microsomal membranes in a "salvage compartment." The inventors fully expect that the CT-B transformed plant tissues will also show CT-B pentamers in the cells.

It is thought that the retention of the proteins by recycling through the salvage compartment and the ER is one factor in the success of these new transgenic plants in edible vaccines for inducing secretory immune responses in animals including humans.

In another preferred embodiment of this invention, the LT holotoxin can be produced in transformed plants by stable or transient incorporation of DNA coding for an LT-B or CT-B containing protein and an LT-A or CT-A containing protein. Again the preferred LT-B or CT-B containing proteins are those that have C-terminus modifications to include an ER retention sequence with LT-B or CT-B containing proteins having N-terminus ER signal sequences and C-terminus ER retention sequences being particularly preferred. It is thought that the presence and retention of holotoxin in the plant cells may act as even a better adjuvant for enhanced secretory immune response in some circumstances.

Additionally, fusion proteins of both the LT-B or CT-B containing protein and LT-A containing protein can be stably or transiently incorporated into plant cells in such a way that the fusion modified LT-B or CT-B pentamer and/or LT or CT holotoxins are formed and retained in the cell in ER recycling vesicles or ER salvage vesicles. These vesicles are believed to form or bud on the ER surface, but instead of migrating to cell machinery that direct the vesicles to other parts of the cell, the vesicles recycle back to the ER. Thus, fusing a gene for a given colonization and/or virulence antigen to an N-terminal or C-terminal sequence encoding the LT enterotoxin subunits or the CT toxin subunits can be used to enhance immune responses to other antigens, such as viral antigens such as the Norwalk virus capsid protein or antigens of Newcastle disease virus. Of course, the fusions must be of such a nature as to not destroy the ability for the B unit of LT or CT to form pentamers or to inhibit or prevent their ability to bind to GM-1 ganglioside. Additionally, for LT or CT coding frames that have LT-A or CT-A elements, the A or B subunit fusions must be designed so that the A subunit can still associate with the B, preferably the A1 part of the A subunit is conserved to facilitate C-terminus association of A subunit with the B subunit pentamer to form fused LT or CT holotoxin.

Besides the LT enterotoxint the cholera toxin, the PapG protein adhesion that specifically binds to alpha-D-galactopyranosyl-(1,4)-beta-D-galactopyranoside, or the invasions causing penetration of bacteria through epithelial cell membranes as identified in a clone from *Yersinia pseudotuberculosis*, Shigella, and Salmonella can also be used in the present invention. The inventors believe that the inclusion of DNA sequences coding for either LT-B, CT-B, LT-B and LT-A, or CT-B and CT-A will facilitate the transportation into cells of the intestinal mucosa of the gene fusion of other vaccine antigens and will lead to enhanced mucosal and humoral immune responses to the other antigens. Thus, the LT-B or CT-B pentamers or holotoxin components of the fusion proteins should act as adjuvants to enhance the immune response to the fused antigens, especially when the fused LT-B or CT-B pentamers or LT or CT holotoxin is retained in the salvage compartment of the transformed plants.

This invention includes plants, seeds, and plant tissue capable of expressing at least a DNA sequence encoding an LT-B or CT-B containing protein and optionally another antigen including colonization and/or virulence antigens, and/or antigenic determinants thereof and/or fusion proteins of the antigens or determinants of pathogens, compositions useful for the stimulation of a secretory immune response in a mammal, methods for stimulating a secretory immune response in mammals so as to inhibit colonization and/or invasion through mucosal surfaces by pathogens, unique vectors containing DNA sequences coding for colonization or virulence antigens, and a method for producing colonization or virulence antigens or pathogenic microorganisms in plants. Again, the LT-B or CT-B coding sequence preferably includes a C-terminus ER retention sequence and/or a N-terminus ER signal sequence.

The antigens of pathogenic microorganisms suitable for fusing with either the LT-B or LT-A subunits of the LT enterotoxin or the CT-B or CT-A subunits of the CT toxin and expressed in transgenic plants of the present invention include, without limitation, colonization antigens, virulence antigens, antigenic determinants of virulence antigenc or colonization antigen, or a fusion protein containing either the antigen or its determinant.

Additionally, the present invention is directed to the coexpression of antigens of pathogenic microorganisms with at least DNA encoding LT-B or CT-B containing a C-terminus ER retention sequences. Suitable antigenic determinants for coexpression in the transgenic plants of the present invention include, without limitation, colonization antigens, virulence antigens, antigenic determinants of virulence antigens or colonization antigen, or a fusion protein containing either the antigen or its determinant.

Moreover, this invention is also directed to the transformation of plants or plant tissues with synthetic DNA sequences encoding LT-B and/or LT-A and/or CT-B and/or CT-A where the bacterially preferred amino acid codons have been systematically replaced by plant preferred amino acid codons. This replacement or substitution of plant preferred codons for the corresponding bacteria preferred condon will further enhance the transgenic plant expression of the LT-B and/or LT-A and/or CT-B and/or CT-A proteins and/or facilitate the expression of the protein in a particular part of the plant.

The present invention also relates to an immunogenic system comprising a genetically transformed plant tissue and an antigenic agent where the tissue is comprising or expressing a DNA sequence encoding one or more immunogenic agents where the tissue is capable of inducing an immune response to the expressed immunogenic agents in animals sufficient to immunize the animals against the agents when the animal is administered the plant material by oral ingestion.

The present invention also relates to a food comprising at least a portion of a transgenic plant material comprising or expressing a DNA sequence encoding one or more immunogenic agents where the material is capable of inducing an immune response to the expressed immunogenic agents in animals sufficient to immunize the animals against the agents when the animal is administered the plant material by oral ingestion.

The present invention also relates to a plasmid vector for causing genetic transformation of plant cells to yield a plant comprising or expressing sequences coding for one or more immunogenic agents where the agents are capable of inducing an immune response in animals sufficient to immunize the animals against the agents when the animal is administered the plant material carrying the vector by oral ingestion.

The present invention also relates to a DNA fragment useful for microparticle bombardment transformation of plant cells to yield a plant comprising or expressing a DNA sequence encoding one or more immunogenic agents where the agents are capable of inducing an immune response to the expressed immunogenic agents in animals sufficient to immunize the animals against the agents when the animal is administered the plant material carrying the fragment by oral ingestion.

The present invention also relates to an immunologic protocol comprising administering a sufficient oral dose of an immunogenic system comprising a transgenic plant expressing a DNA sequence encoding one or more immunogenic agents where the system is capable of inducing an immune response to the expressed immunogenic agents in the animal sufficient to immunize the animals against the agents.

The present invention also relates to a method for producing a vaccine or vaccine adjuvant comprising the steps of constructing a plasmid vector or a DNA fragment by operably linking a DNA sequence encoding one or more immunogenic agents where the material is capable of inducing an immune response to the expressed immunogenic agents in animals sufficient to immunize the animals against the agents and a plant-functional promoter operably linked to the DNA sequence capable of directing the expression of the agents in a plant, transforming a plant cell with the vector or DNA fragment to produce a transganic plant, growing the transgenic plant, and preparing an effect dose of the transgenic plant to fed to animals.

The present invention further relates to a plasmid vector for transforming a plant comprising a DNA sequence encoding a synthetic LT-B or CT-D containing protein designed to replace bacterial preferred amino acid codons with plant preferred amino acid codons in LT-B or CT-B encoding region and a plant-functional promoter operably linked to the DNA sequence capable of directing the expression of the protein in the plant. A preferred LT-B plant specific designed DNA sequence is shown in Example 20.

A. Brief Description Of Experimental Data

The inventors constructed LT-B expression vectors (pLTB110 and pLTB140) and LT-B-SEKDEL expression vectors (pLTK110 and pLTK140) for plant transformation. The 110 vectors contain the 35 S promoter, while the 140 vectors contain the patatin promoter. The vectors were constructed by ligating the LT-B gene 5' of soybean vegetative storage protein terminator (VSP-ter) into the vector plBT200. The LTB110 and pLTK110 vectors were constructed to contain a plant expression cassette that includes a nopaline synthase promoter (Nos-pro), a neomycin phosphotransferase coding region (NPT II) for kanamycin resistance, a nopaline synthase polyadenylation site (Nos-ter), and a cauliflower mosaic virus (CaNV) 35 S promoter linked to the TEV (tobacco etch virus) 5' nontranslated leader sequence which acts as a translational enhancer. This expression cassette was cloned into the expression vector pBI101 (available from Clonetech Laboratories, Inc., Palo Alto, Calif.) to obtain the target pLTB110 vector. For the formation of an expression vector (pLTK110) containing an LT-B gene with an endoplasmic reticulum retention sequence, the above construct was further modified by an oligomer for the coding region of the polypeptide SEKDEL ligated at the SpeI site of the LT-B gene.

Plant transformation experiments were conducted using a leaf disc system with *Agrobacterium tumefaciens* as the gene transfer agent. Shoots were regenerated from transformed callus on medium containing the antibiotic kanamycin for selection. These shoots were rooted and transplanted to soil for propagation.

Because Agrobacterium-mediated transformation of plant cells results in random nuclear insertion of the transfer DNA (T-DNA), individual transformants were expected to have varying levels of gene expression due to chromosomal positional effects, but all unexpectedly higher than the prior art due to the improved expression design of the instant invention. Expression of the LT-B coding gene in tobacco or potato plant transformants was assayed by Northern blots and the levels of recombinant proteins quantified by ELISA. The transformants expressing high level of LT-B were selected for further studies. Generally, LT-B expression levels of between about 1 to about 15 µg per gram of total soluble protein were preferred in the selection process. A sufficiently high level of antigen expression in the cells of transformants is necessary to ensure that the levels of antigen are above the threshold level for eliciting an immune response in animals when the transgenic plant material is consumed as food by an animal.

In order to facilitate this selection process, the inventors have discovered and perfected a set of novel procedures for identifying the rare potato transformants that show the sufficiently high levels of expression of a given antigen such as LT-B to result in the desired immune response when appropriately presented to an animal.

Upon visual inspection of the LT-B pentamer crystal structure, the inventors reasoned that the C-terminus of LT-B in the pentamer may be sufficiently exposed at the protein surface to permit selective genetic engineering. The engineering designed to attach an ER retention sequence such as KDEL to the C-terminus of the LT-B gene with the hope that the attached ER retention sequence would not interfere with protein folding and oligomerization and possibly result in the formation of LT-B pentamers with enhanced endoplasmic reticulum retention. Previous fusion-protein studies have demonstrated successful expression of peptides at the C-terminus of LT-B in which the conformation of both the LT-B and the peptide was retained. F. Schodel, H. Will, S. Johansson, J. Sanchez, J. Holmgren, *Gene*. 99, 225 (1991); T. O. Nashar, T. Amin, A. Marcello, T. R. Hirst, *Vaccine*. 11, 235 (1993); L. Cardenas and J. D. Clements, *Infect-Immun*. 61, 4629 (1993). However, other fusion-proteins have been shown to interfere with pentamer formation of LT-B or to interfere with holotoxin formation.

To confirm stable incorporation of antigen coding sequences in transgenic plants, the inventors used a vector (pLTK110) encoding a LT-B-SEKDEL fusion protein, generally constructed by ligating an oligonucleotide encoding for amino acids SEKDEL at the carboxy terminus of the LT-B gene. Plants transformed with this vector showed significantly elevated levels of the recombinant protein, compared to LT-B levels from plants transformed with a vector (pLTB110) which lacked C-terminus modification. Tobacco plants expressing LT-B-SEKDEL accumulated 4 to 14 µg per gram of total soluble protein; a level substantially higher on average than the LT-B expressing plants. Of course, the vector construction incorporating these alternate ER retention sequences would include the DNA sequence coding for them in place of the DNA sequence encoding SEKDEL at the C-terminus.

To investigate the oligomerization of LT-B and LT-B-SEKDEL, the immunoprecipitates from radio-labeled leaves of transformed tobacco plants were analyzed. This analysis showed that the transformants gave similar protein migrations as compared to bacterial synthesized protein.

Additionally, the signal where the monomer migrates increased when the sample was boiled prior to being run on SDS-PAGE. This increase in monomer signal indicates that the LT-B-SEKDEL fusion-protein does indeed oligomerize inside the transformant cells and that the oligomern of LT-B or TT-B-SEXDEL dissociates into monomers in a fashion similar to the bacteria-produced rLT-B (protein purified from *E. coli* expressing it from a recombinant plasmid).

The gel filtration profile of the plant sample was also the same as that of the bacterially derived protein. Both proteins eluted with an apparent molecular weight of 38 kDa, as has been previously shown for the LT-B pentamer indicating the similarity in the quaternary structure of the proteins expressed in bacterial or plant systems.

To determine the immunogenicity of plant-derived LT-B-SEKDEL when fed orally, Balb/c mice were given by gavage a soluble extract of the tobacco leaves expressing the LT-B-SEKDEL. Another group of mice were given rLT-B purified from *E. coli* expressing the antigen from a recombinant plasmid. An antigen equivalent dose (as determined by ELISA) of 12.5 pg was administered to each mouse by gavage. Serum and mucosal antibody responses were examined by ELISA for antibodies. Anti LT-B antibodies were detected in both serum as well as mucosal extracts of the sacrificed mice. We found both serum and mucosal antibody responses to rLT-B in mice given either the plant extracts or bacteria-derived protein.

Toxin neutralization assays were performed to determine the protective nature of the antibodies elicited in mice by the plant derived samples. Both serum and mucosal (humoral and secretory) antibodies from animals immunized orally with LT-B-SEKDEL transformed plant tissue were able to neutralize the biological activity of LT to the same extent as serum and mucosal antibodies from animals immunized orally with an antigen equivalent dose of rLT-B.

Tobacco was our initial test system since it has been extensively utilized as a transgene expression model. However, since tobacco leaves are rich in toxic alkaloids, it was desirable to work with a plant system of which the edible tissue expressing the vaccine antigen could be fed to animals in an unmodified form.

To avoid alkaloid toxicity problems we transformed potatoes because tubers can be obtained from transformed plants in a short period of time and are readily accepted by mice as alternatives to laboratory feed mixtures. Leaf explants from axenically grown potato variety "FL1607," H. Wenzler, G. Mignery, G. May, W. Park, Plant Science 63, 79 (1989), were transformed with *A. tumefaciens* harboring pLTB110 and pLTK110. Transformants were selected and tubers were analyzed. The levels of the LT-B or LT-B-SEKDEL ranged from 2 to 30 $\mu$g per gram and 60 to 110 $\mu$g per gram of total soluble protein respectively, which represents an upper level of expression of about 0.01% foreign soluble protein.

The tubers when fed to mice gave an immune response similar to that for the transformed tobacco leaves confirming our hypothesis that antigen expressing edible tissue when fed in an unmodified form can induce an immune response.

Mice fed with the control (non-transformed) tubers developed no such response. Also shown are responses from animals fed an antigen equivalent dose of soluble bacterially expressed LT-B. This data demonstrates the feasibility of using transgenic plants as expression and delivery systems of oral immunogens for eliciting an immune response by simply feeding the edible tissues. It is especially significant since the immunogen was still associated with the other plant material which was unmodified in any fashion whatsoever.

Taken together, our results demonstrate the successful expression and production of LT-B and LT-B-SEKDEL fusion protein in plants. The plant derived rLT-B shows properties analogous to the bacterial LT-B. It is antigenic and binds to $G_{M-1}$ ganglioside, its natural ligand on the intestinal epithelia. We have also demonstrated the efficacy of the transgenic plant tissue as an oral immunogen when fed to mice. This is the first demonstration that antigens expressed in transgenic plants retain immunogenic properties and are orally active immunogens.

The following examples will serve to illustrate the practice of the invention in more detail.

EXAMPLE 1

This example illustrates the construction of expression plasmid vectors containing a LT-B coding region.

Plasmids (pDF82 and pJC217) containing the coding regions for the A and B subunits of the *E. coli* heat-labile entertoxin (LT) were obtained from Dr. John D. Clements, Tulane University School of Medicine, New Orleans, La. pDF82 (Clements et al. *Infect. Immunity*, 40, 653 (1983)) contains both the LT-A and LT-B coding sequences in an overlapping configuration on a PstI fragment cloned in pBR322. pJC217 contains the LT-B coding sequence on a 777bp HindIII fragment from pDF82, subcloned in the HindIII site of pUC8.

We modified the C-terminus of the LT-B coding region to contain the amino acids Ser-Glu-Lys-Asp-Glu-Leu (SEKDEL) in the following way. pJC217 was digested with SpeI, which cuts at the translation termination site, and ligated with a synthetic DNA fragment obtained by annealing the following oligonucleotides:

5'-CTCTGAGAAAGATGAGCTATGA-3' (SEQ ID NO: 5), and

5'-CTAGTCATAGCTCATCTTTCTCAGAG-3' (SEQ ID NO: 6).

The remaining free SpeI terminus was digested with mung bean nuclease to a blunt end, and the plasmid circularized to form pLTK217. The 3' end of the modified C-terminus thus reads (the SpeI site is underlined):

```
AGT ATG GAA AAC TCT GAG AAA GAT GAG CTA TGA CTA GT
 S   M   E   N   S   E   K   D   E   L stop
(SEQ ID NO: 7)
``` where the upper line shows the nucleotide sequence, and the lower line shows the corresponding amino acid sequence.

The LT-B coding regions and flanking sequences from the unmodified (pJC217) and C-terminal SEKDEL modified (pLTK217) were subcloned into pBluescript KS (Stratagene, La Jolla, Calif.) using EcoRI and HindIII, to give pLTB10 and pLTK10, respectively. The EcoRI sites in pLTB10 and pLTK10 were destroyed by blunting with mung bean nuclease and recircularizing to give pLTB11 and pLTK11, respectively. The coding sequences were then excised from pLTB11 and pLTK11 with BamHI and DraI, and ligated into pIBT200 digested with BamHI and SmaI, to form pLTB200 and pLTK200 respectively.

pLBT200 contains regulatory elements needed for expression in plant cells of inserted coding sequences, an it was constructed as follows. A 576 bp fragment containing a polyadenylation signal from the 3' flanking region of the soybean vspB gene (Mason et al., *Plant Cell*, 5, 241 (1993)) was ligated into the SacI and EcoRI sites of pUC19 (Gibco-BRL, Bethesda, Md.) to give PUC-V. A 950 bp fragment containing the cauliflower mosaic virus 35S promoter with duplicated enhancer fused to the tobacco etch virus 5'-UTR (TEV leader) was obtained by digestion of pRTL2-GUS (Carrington et al., *Plant Cell*, 3, 953 (1991) with NcoI, blunting the resulting ends with mung bean nuclease, and digestion with HindIII. The resulting fragment was inserted into pUC-V digested with SmaI and HindIII to give pIBT200, which contains a polylinker that carries the sites Ba-mHI, SmaI, KpnI, and SacI between the 35S promoter-TEV leader and the vspB 3' end, for insertion of foreign coding sequences for expression in plant cells.

We modified the translation initiation site of LT-B to contain a NcoI site, using polymerase chain reaction (PCR) and mutagenic primers. A 68 bp fragment comprising the 5' end of the LT-B coding sequence was obtained by PCR using pDF82 as template and the following primers!

5'-GGGGCCATGGTTAAAGTAAAATGTTATGTTTTA-3' (SEQ ID NO: 8), and

5'-AGACTGGGGAGCTCCGTATG-3' (SEQ ID NO: 9).

The NcoI site is underlined.

The resulting PCR fragment was digested with NcoI and SacI, and ligated into pIBT210.1 digested likewise, to give pLTB5'.

pIBT210.1 is similar to pIBT200, except that its polylinker carries the sites NcoI, BaMHI, Smal, KpnI, and SacI. It was constructed as follows. The 35S promoter-TEV leader fusion from pRTL2-GUS was modified to remove the EcoRI site at the promoter-leader junction by filling in with Klenow enzyme and recircularizing to give pRZL4. plTL4 was digested with NcoI, and the resulting ends blunted filling in with Klenow enzyme, and the resulting DNA digested with HindIII to release the promoter-leader fragment. Likewise, pUC-V was digested with BamHI and the resulting ends blunted by filling in with Klenow enzyme, and the resulting DNA digested with HindIII. The pUC-V vector and the pRTL4 promoter-leader fragment thus prepared were ligated to form pIBT210.1.

The modified 5' end of LT-B it pLTB51 was then combined with the unmodified (pLTB200) and modified (pLTK200) 3' ends of the coding sequence as follows. pLTB200 and pLTK200 were digested with SacI to obtain the 3' end coding sequence fragments, which were ligated separately into pLTB5' digested with SacI, to give pLTB210 and pLTK210, respectively. These plasmids contain the LTB coding sequence with modified 5' end and the unmodified (pLTB210) or modified (pLTK210) 3' ends between the 35S promoter-TEV leader and the vspB polyadenlation signal and 3' flanking region.

The expression cassettes in pLTB210 and pLTK210 were transferred to the Agrobacterium T-DNA vector pBI101 (Clonetech Laboratories, Inc., Palo Alto, Calif.) by digesting with HindIII and EcoRl, and ligating with pBI101 digested likewise to give PLTB110 and pLTK110, respectively. Thus, pLTB110 and pLTK110 contain the coding sequenoes of LT-B with a modified 5' end and either unmodified (pLTB110) or modified (pLTK110) 3' ends, positioned between the 35S promoter-TEV leader and the vspB polyadenylation signal and 3' flanking region, all within the T-DNA borders from pBI101, allowing transfer of the expression cassettes to the nuclear DNA of plant cells by Agrobacterium-mediated transformation, and selpction of transformants on kanamycin-containing media.

A further modification of pLTB110 was constructed by substitution of the patatin promoter from potato for the 35S promoter. The patatin promoter from pPS20 (Wenzler et al., *Plant Mol. Bio.*, 12, 41 (1989)) was obtained by digestion of pPS20 with BamHI, followed by partial filling in with Klenow enzyme and dGTP and DATP only. The resulting DNA was digested with HindIII to release the 2.3 kbp promoter fragment. pLTB110 was digested with XhoI, followed by partial filling in the Klenow enzyme and dCTP and TTP only, and finally was digested with HindIII. The pLTB110 vector fragment was purified free of the 35S promoter fragment thus released, and the resulting vector ligated with the patatin promoter fragment prepared as described above, to give pLTB140.

A similar construct (containing the modified SEKDEL C-terminus) is made by substitution of pLTK110 for pLTK110 in the preceding paragraph.

The structures of pLTB140 and pLTK110 are shown in FIGS. 1A and 1B, respectively, while the structure of pLTB110 is shown in FIG. 1C.

EXAMPLE 2

This example illustrates the construction of expression plasmid vectors containing an LT-A coding region.

We modified the translation initiation site of LT-A to contain a NcoI site, using polymerase chain reaction (PCR) and mutagenic primers. An 88 bp fragment comprising the 5' end of the LT-A coding sequence was obtained by PCR using pDF82 as template and the primers:

5'-GGGGCCATGGTTAAAAATATAACTTTCATTTTT-3' (SEQ ID NO: 10), and

5'-ATCTGGGGGTCTAGAGTC-3' (SEQ ID NO: 11).

The NcoI site is underlined.

The resulting PCR fragment was digested with NcoI and XbaI, and ligated with pRTL4 of Example 1 digested likewise to give pLTA5'. This plasmid contains the 35S promoter-TEV leader fused to the modified 5' end of the LT-A coding sequence, which fragment was obtained by digestion of pLTA5' with HindIII and XbaI, and ligated with pUC-V digested likewise to give pLTA210.5. The 3' end of the LT-A coding sequence was obtained by digestion of pDF82 with XbaI and SacI, and ligated with pLTA210.5 digested likewise to give pLTA210. Thus pLTA210 contains the LT-A coding sequence with a modified 5' end positioned between the 35S promoter-TEV leader and the vspb polyadenylation signal and 3' flanking region.

The expression cassette in pLTA210 was transferred to the Agrobacterium T-DNA vector pIBT100, which had been constructed as follows. pIBT200 of Example 1 was digested with HindIII and EcoRI to give a fragment containing the polylinker (BamHI, SmaI, KpnI, SacI) between the 35S promoter-TEV leader and the vspB 3' end, which was ligated with pBI101 digested likewise to give pIBT100. pLTA210 was digested with Xhol and SacI to give a fragment containing the TEV leader-LTA coding sequence, which was ligated with pIBT100 digested likewise to give pLTA110. Thus, pLTA110 contains the LT-A coding sequence with a modified 5' end positioned between the 35S promoter-TEV leader and the vspB polyadenylation signal and 3' flanking region, all within the T-DNA borders from pBI101, allowing transfer of the expression cassette to the nuclear DNA of plant cells by Agrobacterium—meditated transformation.

EXAMPLE 3

This example illustrates the construction of vectors for coordinate expression of LT-A and LT-B.

Here we describe the construction of plasmids which will allow coordinate expression of LT-A and LT-B for the assembly of holotoxin LT in potato tuber cells. Because the A and B subunits in LT are combined in the ratio of 1:5, it is necessary to modulate the transcription levels for these genes in transgenic plants so as to approximate a similar ratio of the mRNAs for LT-A and LT-B in the transformed cells. We have done this by using promoters having different activities in potato tubers to drive transcription of the LT-A and LT-B coding sequences.

The 5' end of the LT-A coding sequence in pLTA210.5 was fused with two different promoters as follows. In one case the patatin promoter was truncated to contain only the 3' terminal 350 bp. The 2.3 kb HindIII/BamHI patatin promoter fragment from pPS20 of Example 1 was subcloned in pUC19 to form pUC-PS. pUC-PS was digested with XbaI and SAlI, followed by blunting the ends by filling in with Klenow enzyme and recircularization to exclude the 5' terminal 1.95 kb of the patatin promoter, to yield pPSX. The 350 bp truncated patatin promoter was obtained by digestion of pPSX with namHI, followed by blunting the ends by filling in with Klenow enzyme, and finally digestion with HindIII, and ligated with pLTA210.5 prepared by digestion with NcoI, followed by blunting the ends by filling in with Klenow enzyme, and finally digestion with HindIII. The resulting pLTA-PX contains the truncated 350 bp patatin promoter fused to the modified 5' end of the LT-A coding sequence.

Figure 11:
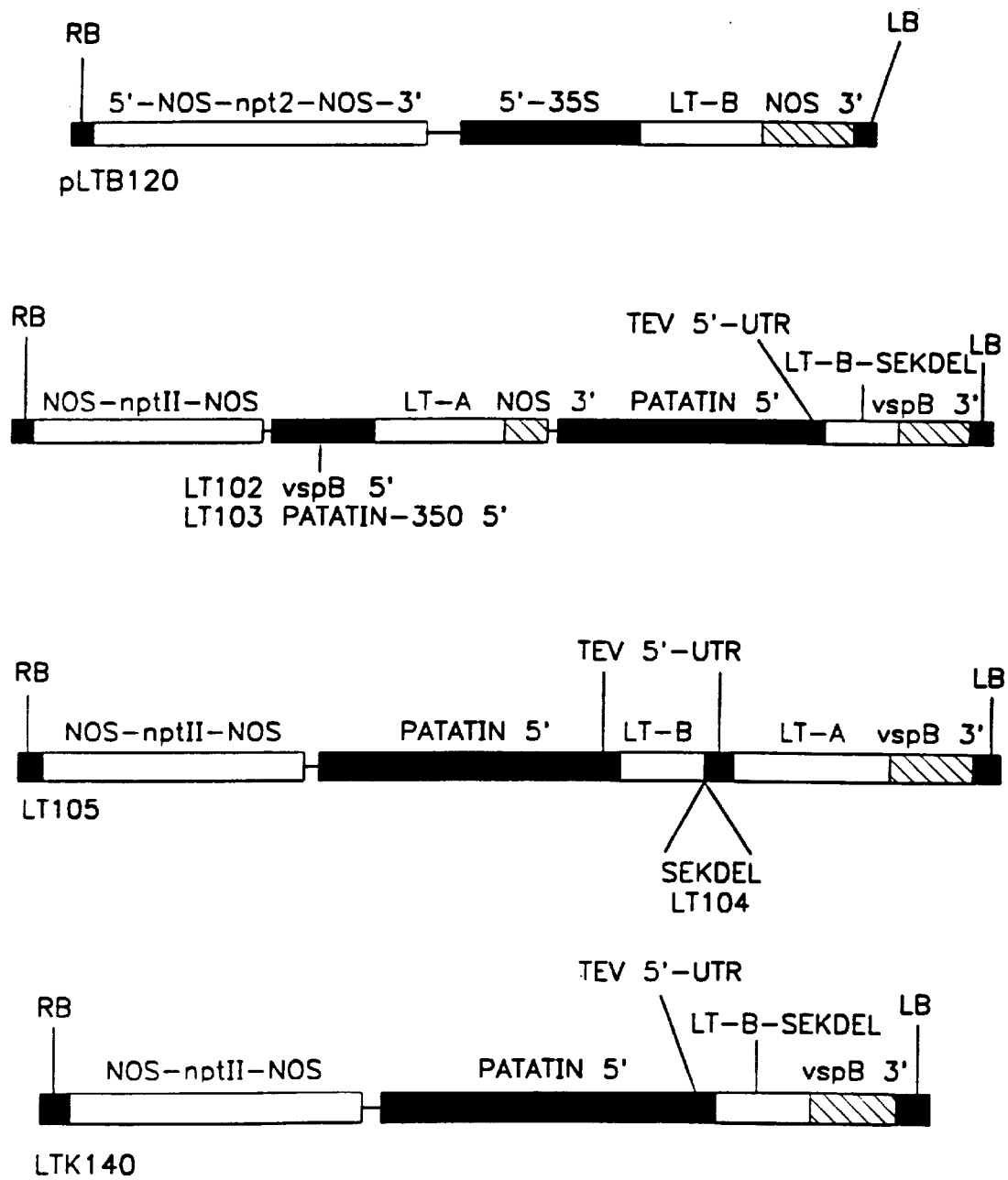
Figure 12:
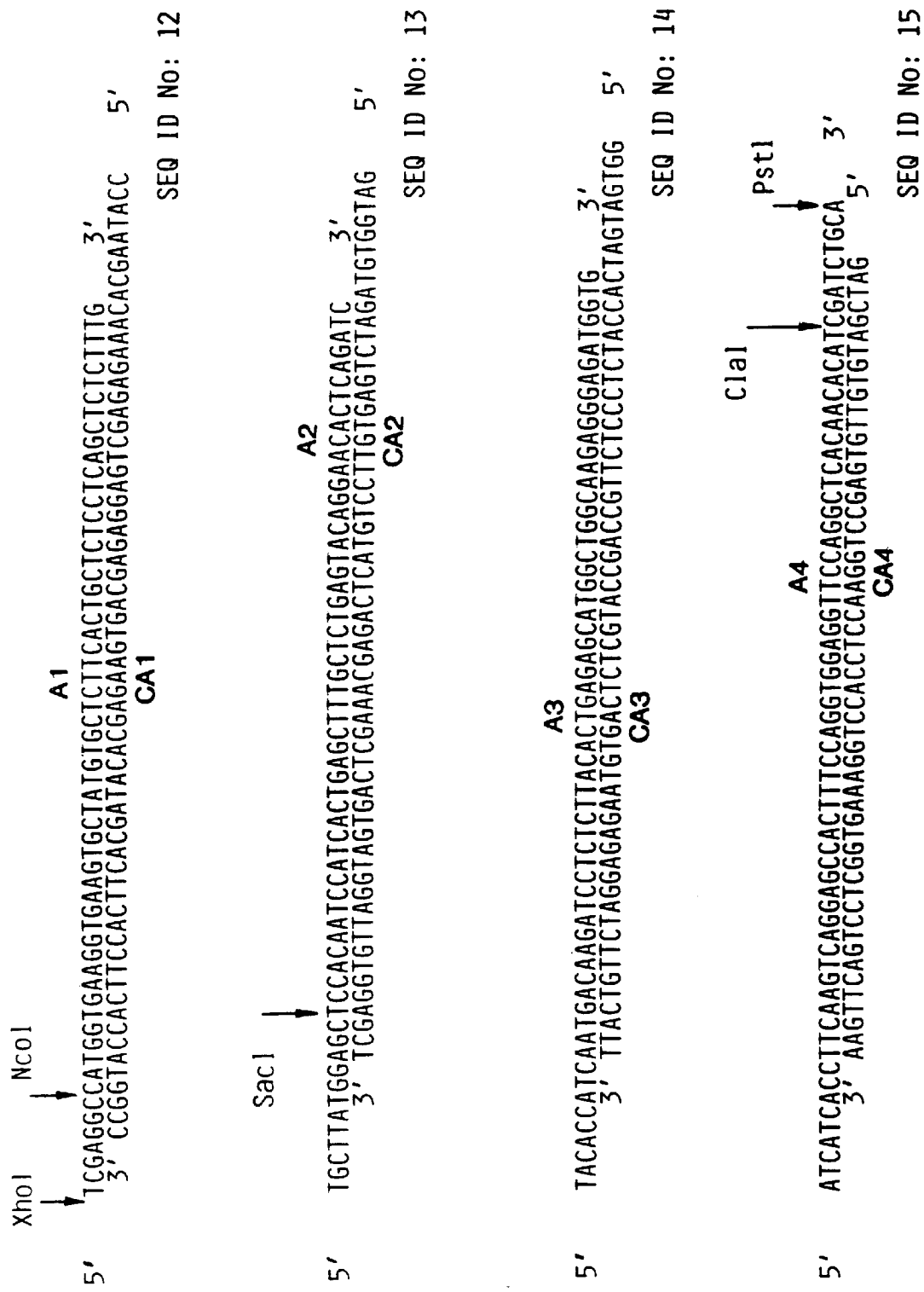

In the second case the LT-A coding sequence in pLTA210.5 was fused with a truncated form of the soybean vspB promoter. A 1534 bp vspB promoter fragment in pKS-vspBXP (Mason et al., Plant Cell, 5, 241 (1993)) was deleted from the 3' end to a point 7 bp upstream of the initiation codon for vspB using exonuclease III and mung bean nuclease, to yield pxg-vspBXΔ10. A 5' deletion of 665 bp was obtained by first digesting pKS-vspBXΔ10 with KpnI, followed by blunting the ends with T4 DNA polymerase, and finally digestion with HindIII, and the resulting 835 bp fragment purified. This truncated promoter fragment was ligated with pLTA210.5 prepared by digestion with NeoI, followed by blunting the ends by filling in with Klenow enzyme, and finally digestion with HindIII, to give pLTA-VH which contains the truncated 835 bp vspB promoter fused to the modified 5' end of the LT-A coding sequence.

The 3' end of the LT-A coding sequence was fused to the nopdline synthase (NOS) polyadenylation signal as follows. The 756 bp XbaI/SacI fragment from pDF82 (containing the 3' end of the LT-A coding sequence) was ligated together with the 250 bp SacI/EcoRI fragment from pBI101 (containing the NOS polyadenylation signal) and pBluescriptKS digested with XbaI and EcoRI to give pLTA-3N.

The two different promoter-$5^1$ coding sequence fusions were combined separately with the 3' coding sequence-NOS polyadenylation signal fusion as follows. pLTA-PX and pLTA-VH were digested with HindIII and XbaI, and the promoter-5S coding sequence fragments purified. pLTA-3N was digested with Xbal and SAlI, and the 3' coding sequence-NOS polyadanylation signal fragment purified. The pLTA-PX HindIII/XbaI fragment was ligated together with the pLTA-3N XbaI/SalI fragment and pLTB110 of example 1 was digested with HindIII and SalI to give pLT101. Similarly, the pLTA-VH HindIII/XbaI fragment was ligated together with the pLTA-3N XbaI/SalI fragment and pLT'B110 digested with HindIII and SalL to give pLT100. Thus pLT101 and pLT100 contain expression cassettes for both LT-A and LT-B, under the control of different 5' and 3' regulatory elements, all within the T-DNA borders, allowing insertion of the construct into the nuclear DNA of plant cells using Agrobacterium-mediated transformation.

Construction of pLTl02 and pLT 103:

More specifically, this describes the construction of two plasmids for the coordinate expression of LT-A and LT-B-SEKDEL in potato tuber cells, for the assembly of a recombinant holotoxin LT where the B subunit is modified to contain a microsomal retention signal at the carboxy terminus (SEKDEL). The resulting plasmids, pLT102 and pLT103, are identical to pLT100 and pLT101, respectively with the sole exception that the LT-B coding sequences are modified to encode SEKDEL at the 3' ends.

LT-B-SEKDEL is an example of an LT-B containing protein. LT-B-SEKDEL contains at least one amino acid domain that is substantially homologous with the amino acid sequence of bacterially derived LT-B and CT-B proteins, said amino acid sequence homology is least about 90%, and, in addition, LT-B-SEKDEL is substantially functionally similar to bacterially derived LT-B or CT-B in binding to GM I gangliosides.

To construct pLT102, pLT100 was digested with SpeI and SalI to release the patatin promoter-LT-B coding sequence fusion, and purified the 12 kbp vector fragment containing the vspB promoter-LT-A coding seguence-NOS $_3$' end cassette on the SalI side, and the vspB 3' end on the SpeI side. The TEV 5' -UTR fused to the LT-B coding sequence modified to encode SEKDEL at the carboxyl terminus was obtained from pLTK210 of Example 1 by digestion with XhoI, followed by partial filling in with Klenow enzyme and dCTP and TTP only, and finally digestion with SpeI. The patatin promoter from pPS20 (Wenzler et al., *Plant Mol. Bio*., 12, 41 (1989)) was obtained by digestion of pPS20 with BamHI, followed by partial filling in with Klenow enzyme and dGTP and dATP only, and finally digestion with Sal I to release the 2.3 kbp promoter fragment. All three fragments were ligated together to form pLT102, shown in FIG. 11.

To form pLT103, pLT102 was digested (described above) with HindIII and SalI to release the LT-A expression cassette and purified the vector fragment containing the LT-B-SEKDEL expression cassette. The LT-A cassette was reconstructed by digestion of pLTA-PX (see above) with HindIII and Xbal to obtain the 450 bp fragment, and digestion of pLTA-3N (see above) with Xbal and Sal I to obtain the 700 bp fragment. All three fragments were ligated together to form pLT103, shown in FIG. 11.

Construction of pLTK140:

This example describes the construction of pLTK140, which is identical to pLTB140 of Example 1 with the sole exception that the LT-B coding sequence is modified to encode SEKDEL at the 3' end. Plasmid pLT103 (FIG. 11) was digested with SalI to release the LT-A expression cassette, followed by religation of the vector, to obtain pLTKI40, also shown in FIG. 11. pLTK140 uses the patatin promoter to drive tuber-specific expression of LT-B-SEKDEL in potato plants.

Construction of pLT104 and pLT105:

Plasmid pLT104 was created as a bicistonic cassette for the coordinate expression of LT-A and LT-B-SEKDEL, and pLT105, a bicistronic cassette for the coordinate expression of LT-A and LT-B, for more efficient formation of the holotoxin LT. Because association of the LT-A polypeptide with the LT-B pentamer is inefficient after the LT-B polypeptides have aggregated into the pentamer, a closer proximity of the folding polypeptides may allow more efficient holotoxin formation. Therefore, translation of LT-A and LT-B on separate mRNA's may not allow close proximity of the LT-A and LT-n polypepcider during folding, which could be afforded by translation of LT-A and LT-B from a single RNA containing both coding sequences. The strategy links the patatin promoter to a TEV 5'-UTR/LT-B-SEKDEL (pLT104) or TEV 5'UTR/LT-B (pl.T105) fusion, followed by a TEV 5'-UTR/LT-A fusion and the vspB 3' end. The mRNA generated from this construct in potato tuber cells will contain both LT-B-SEKDEL and LT-A coding sequences.

First, a BamHI site was created at the 3' end of the LT-B-SEKDEL coding sequence by subcloning the 300 bp SacI/SpeI fragment from pLTK210 of Example 1 into pBluescriptKS (Stratagene) to give pLTK-SS. pLTK-SS was then digested with BamHI, followed by partial filling in with Klenow enzyme and dGTP and DATP only, and resulting DNA digested with SacI to obtain the 300 bp fragment. The TEV 5'-UTR/LT-A fragment was obtained by digestion of pLTA210 of Example 2 with XhoI, followed by partial filling in with Klenow enzyme and dCTP and TTP only, and finally digestion with SacI. These two fragments were then ligated together with pLTK140 which had been digested with SacI and purified to obtain the vector fragment, to give pLT104, shown in FIG. 11.

pLT105 was created by ligation of the 2.8 kbp SpeI/SalI fragment from pLTB140 of Example 1 with the vector fragment obtained by digestion of pLT104 (this Example) with SpeI/SalI. pLT105 is shown in FIG. 11.

EXAMPLE 4

This example illustrates the construction of expression vectors that coordinately express LT-A and LT-B coding sequences modified to contain the C-terminus SEKDEL amino acid sequence.

Constructs are made for coordinate expression of LT-A and the LT-B coding sequence modified to contain the C-terminal SEKDEL amino acid sequence, simply by using pLTK110 instead of pLTB110 in the final steps of the process described in Example 3.

EXAMPLE 5

This example illustrates the construction of vectors for the coordinate expression of LT-B and other antigens.

In order to test the ability of LT-B to act as an immune system stimulant or adjuvant when expressed in plant cells coordinately with other antigens and fed to animals, we have constructed a plasmid vector which will allow the coordinate expression of LT-B along with the Norwalk virus capsid protein (NVCP) (Jiang et al., J. Virol., 66, 6527 (1992)). An expression plasmid for NVCP was constructed in a way similar to that described above for pLTB140 of Example 1, to give pNVI40, which contains the patatin promoter, TEV leader, NVCP coding sequence, and NOS polyadenylation signal.

The 4.2 kb pNVI40 SalI/SacI fragment containing the patatin promoter, TEV leader, and NVCP coding sequence, was purified. The 1.3 kb HindIII/SpeI fragment from pLTK210 of Example 1, containing the 35S promoter, TEV leader, and LT-B coding sequence was purified. The 0.6 kb SpeI/EcoRI fragment from pLTK210, containing the vspB (SEKDEL coding sequence and the polyadenylation signal) was purified. These three fragments, pNV140 SalII/SacI, pLTK120 HindIII/SpeI, and pLTK210 SpeI/EcoRI, were ligated together with pBI101 digested with HindIII and EcoRl to give pLTK-NV. Thus, pLTK-NV contains an LT-B expression cassette with the modified C-terminal SEKDEL, and an NVCP expression cassette, all within the T-DNA borders, allowing insertion of the construct into the nuclear DNA of plant cells using Agrobacterium-mediated transformation.

EXAMPLE 6

This example illustrates the transformation of tobacco leaves with a vector containing DNA coding for an LT-B protein having a C-terminus SEKDEL ER retention sequence, pLTK110.

The plasmid pLTK110 was first mobilized into *Agrobacterium tumefaciens* LBA4404 (Clonetech Laboratories, PaloAlto, Calif.) by the direct freeze-thaw method, An G. Meth, Enzymol. 153:292–305 (1987). Transformed clones were isolated by selection on 50 mg/L kanamycin, and plasmid prepared from liquid cultures by alkaline lysis. The structure of plasmids from Agrobacterium were verified by restriction endonuclease digestion.

The technique of in vitro transformation of plants by the Agrobacterium-Ti plasmid system is based on cocultivation of plant tissues or cells and the transformed Agroloacterium for about two days with subsequent transfer of plant materials to an appropriate selective medium. The material can be either protoplast, callus, or organ tissue, depending upon the plant species. Organ cocultivation with leaf pieces is a convenient method.

Tobacco leaves were transformed using a leaf disc system with *Agrobacterium tumefaciens* as the gene transfer agent. Leaf disc transformation was performed in accordance with the procedure described in R. B. Horsch et al. *in Plant Molecular Biology* Manual A5, Kluwer 5 Academic Publishers, Dordecht (1988) p. 1–9. Tobacco seedlings were grown aseptically in tissue culture boxes until 8–10 cm tall. The leaves were cut into small strips or squares to produce a wounded edge.

Leaf discs were precultured for one to two days upside down on MS104 medium to allow initial growth and to eliminiate those discs that were damaged during sterilization or handling. Only the lead discs which showed viability as evidenced by swelling were used for subsequent inoculation. The *A. tumefaciens* containing pLTB110 or pLTK110 which had been grown in YEP medium (10 g/L Bacto-peptone, 10 g/L Yeast extract, 5 g/L NaCl) were diluted one to ten with MSO for tobacco discs. Leaf discs were inoculated by immersion in the diluted transformed A. tumefaciens culture and cocultured on regeneration medium MS104 for three days. Leaf discs were then washed with sterile water to remove the free *A. tumefaciens* cells and placed on fresh MS selection medium which contained 100 μg/mL of kanamycin to glect for transformed plant cells and 500 μg/mL carbenicillin to kill any remaining *A. tumefaciens*. The leaf discs were then transferred to fresh MS selection medium at two week intervals. As shoots formed at the edge of the leaf discs and grew large enough for manual manipulation, they were excised (usually at three to six weeks after cocultivation with transformed *A. tumefaciens*) and transferred to a root-inducing medium, e.g., MS rooting medium. As the roots appeared the plantlets were either allowed to continue to grow under sterile tissue culture conditions or transferred to soil and allowed to grow in a controlled environment chamber.

EXAMPLE 7

This example illustrates the ELISA analysis of plant extracts, specifically tobacco leaf extracts, for the amount of cellular expression of the LT-B and LT-B-SEKDEL protein.

ELISA for LT-B in plant extracts: dissolved in GM-X ganglioside (Sigma, G2375) carbonate buffer (pH 9.6) was coated on polystyrene ELISA plates. After one hour of incubation at room temperature, the buffer was washed of f with PBST and the wells blocked for non-specific binding with 5% milk in PBST. Samples to be assayed were loaded into the wells PBST in duplicates. To obtain standard curve for quantification of LT-B, different dilutions of bacterially derived LT-B were loaded on the same plate. The plates were washed with PBST after one hour incubation at room temperature. Goat antiserum to LT-B diluted 1:1000 in PBST and 2% BSA was incubated in the wells for one hour at room temperature. After washing 4 times with PBST, this was probed with rabbit antiserum against goat IgG conjugated with alkaline phosphatase (Sigma A7650), diluted 1:200 in PBST and 2% BSA. After washing the wells with PBST, they were incubated with nitrophenyl phosphate substrate in diethanolamine buffer, pH 9.8. After incubation for 10 to 30 minutes, the reaction was stopped, by adding NaOH and the absorbance read at 410 nm.

EXAMPLE 8

This example illustrates the ELISA analysis of tobacco plant transformants for LT-B and LT-B-SEKDEL expression.

Figure 2A:
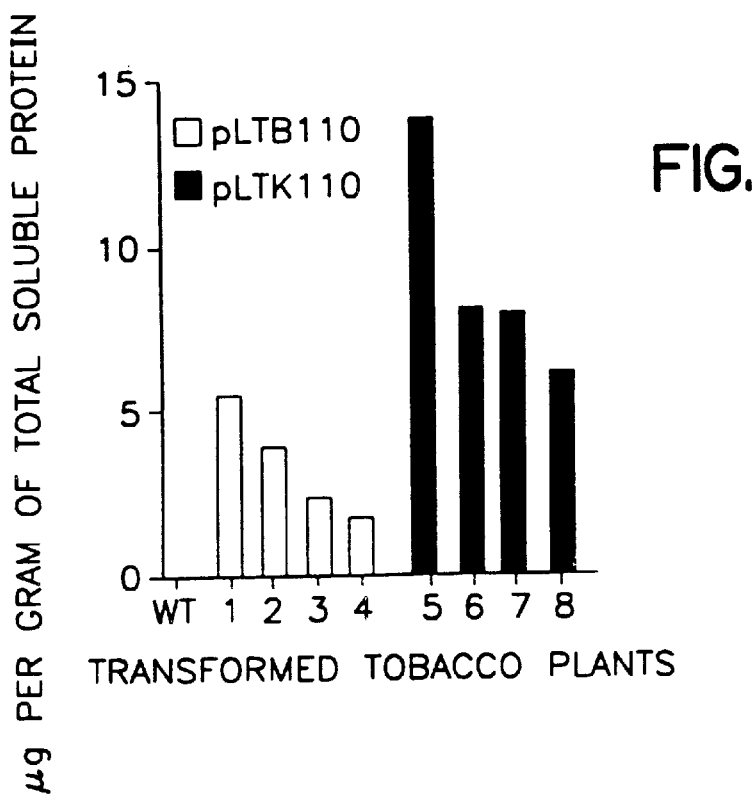
Figure 2B:
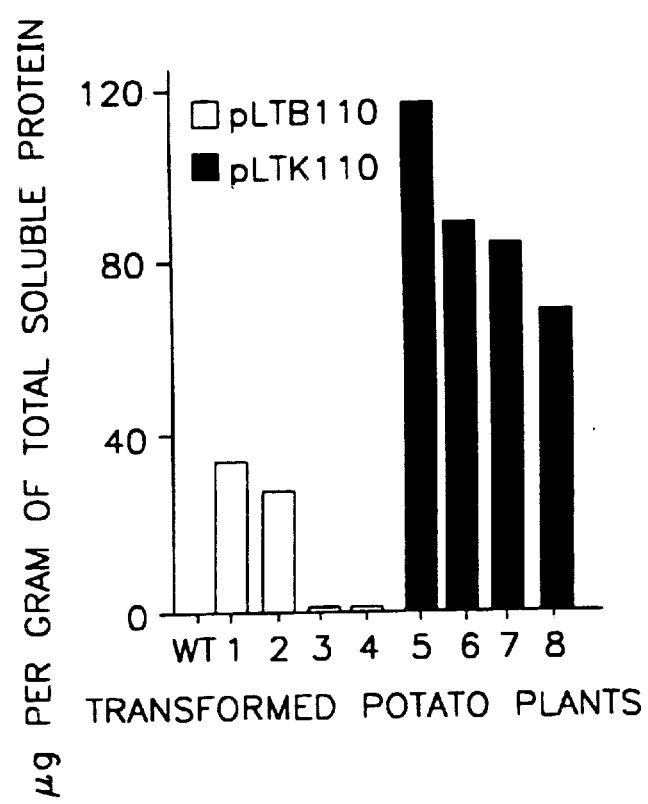

Expression of the LT-D coding gene in tobacco plant transformants was assayed by quantitation of the levels of recombinant proteins by ELISA as shown in FIG. 2. ELISA levels of recombinant protein were determined from soluble protein extracts from independent tobacco transformants (labeled "A" in FIG. 2) which carried either the native LT-B coding region (open bars) or LT-B-SEKDEL (solid bar) coding region with a Ser-Glu-Lys-Asp-Glu-Leu (SEKDEL) ER retention sequence at the LT-B gene C-terminus. Extracts from the tobacco transformants in PBST (phosphate buffered saline, 2mM PMSF, 20 mM ascorbate and 0.05% TWEEN) were centrifuged at 12,000×g and the supernatants obtained were tested by ganglioside-dependent ELISA of Example 7. The 4 transformants showing the highest antigen levels after background subtraction are shown in FIG. 2A.

EXAMPLE 9

This example illustrates the anti-LT-B antibody immunoprocipitation analysis of tobacoo transformants containing genes coding for LT-B and LT-B-SEKDEL.

Figure 3:
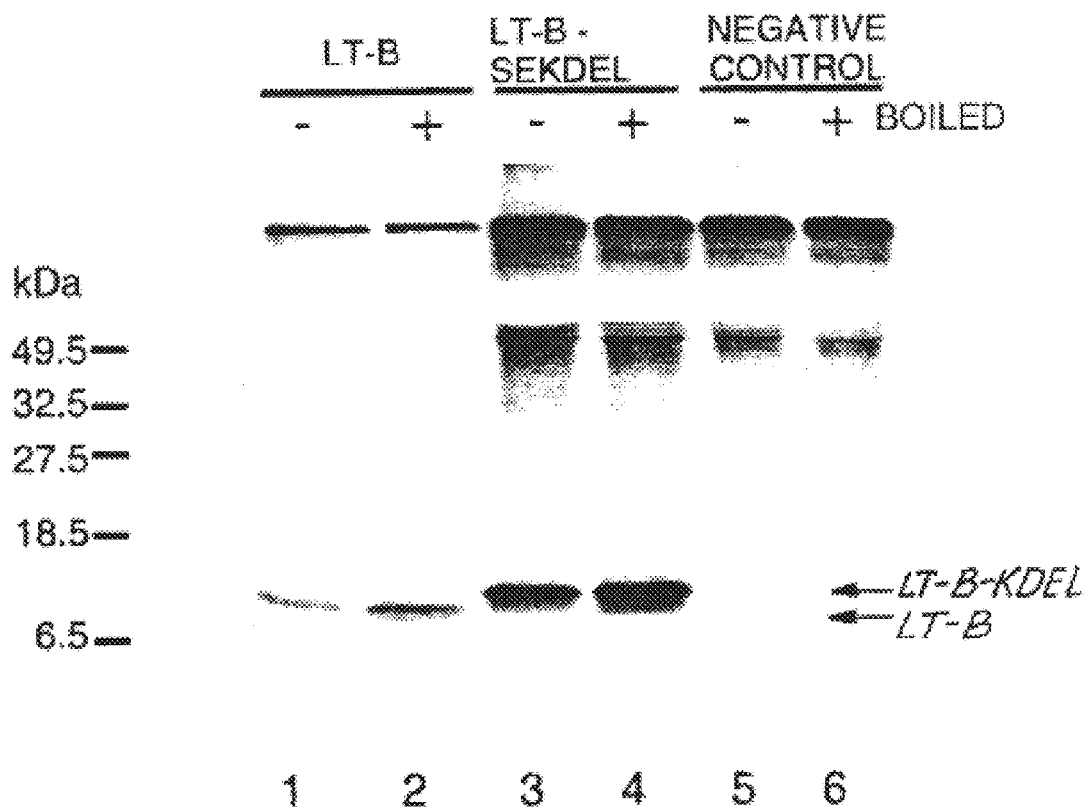

FIG. 3 shows a radiogram of immunoprecipitates using antibodies against LT-B. Immunoprecipitates of extracts from radiolabelled transgenic tobacco leaves expressing LT-B (lanes 1 and 2), LT-B-SEKDEL (lanes 3 and 4), or negative control plants (lane 5 and 6) were used. Leaves were excised and petiolar uptake of 35S labelled Met and Cys was performed for 2 hours at room temperature and illumination of 5380 Lux. The leaves were homogenized in PYREX-Ten Broeck tissue grinder with 0.15 mm clearance and extracted in IP buffer (50 MM Tris pH 7.5, 0.2 M NaCl, 2 MM EDTA, 2mM PMSF, 5 mM DTT, 0.1% BSA and 1% Triton X 100). The extracts were centrifuged at 12000×g for 10 minutes and the supernatant was immunoprecipitated. (Mason et al., Plant Mol. Biol. 11, 845–856 (1988)) and eluted in Laemmli sample heated in boiling water bath for 5 minutes (+), were run on a 15% SDS polyacrylmide gal. The migration of Dio-Rac pre-stainea broad range molecular weight protein standards is indicated to the left. The migration of bacterial-synthesized protein was similar to LT-B-SEKDEL.

EXAMPLE 10

This example illustrates the analysis of the LT-B-SEKDEL proteins in tobacco transformants by size exclusion chromatography designed to demonstrate the oligomerization of the protein in transformant cells.

Figure 4:
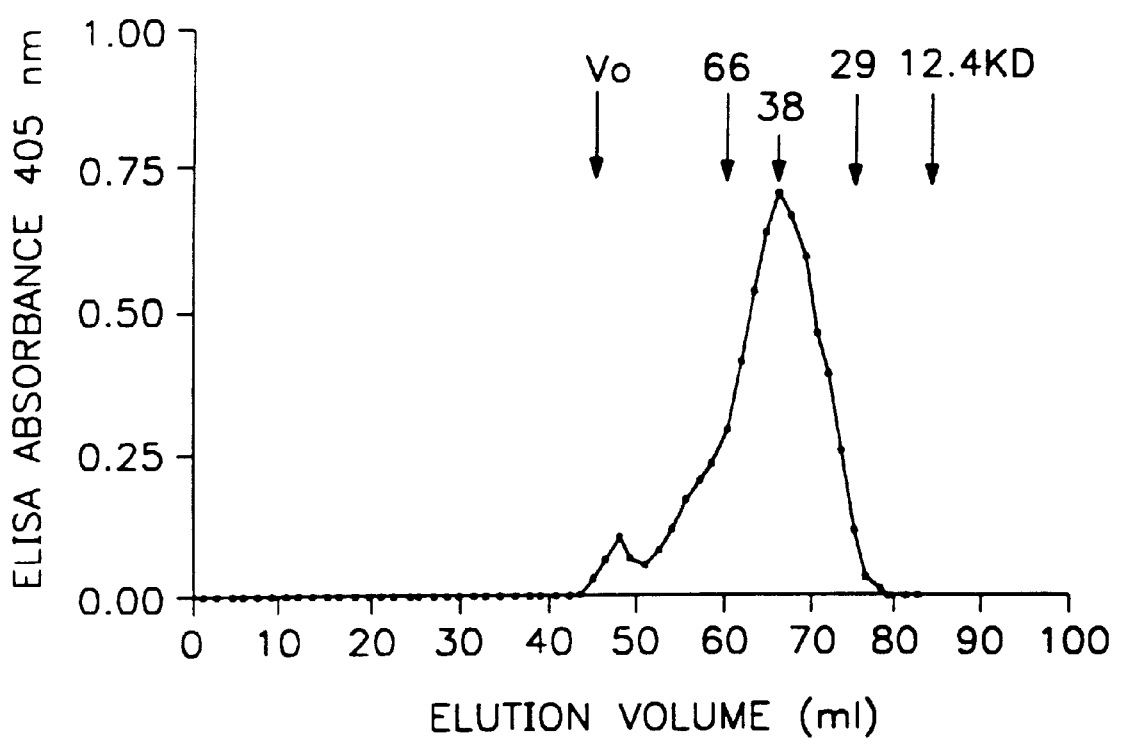
Figure 5A:
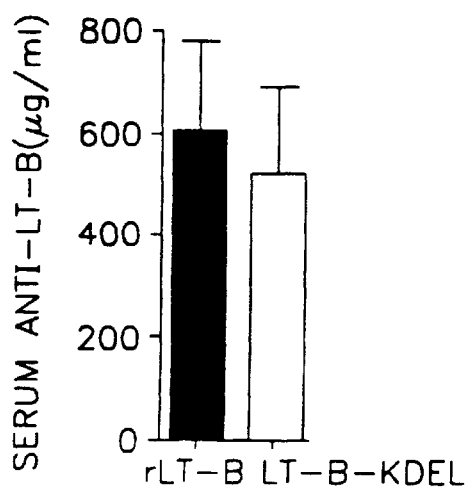
Figure 5B:
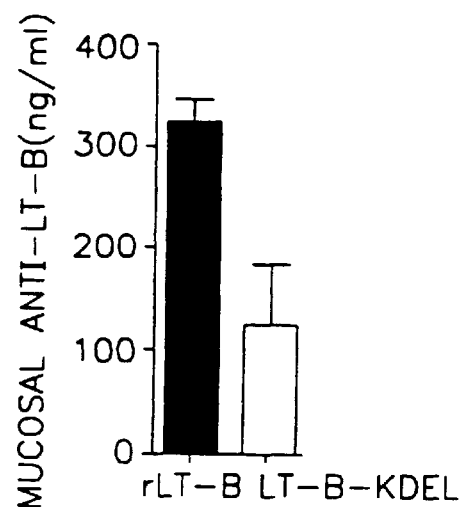
Figure 6:
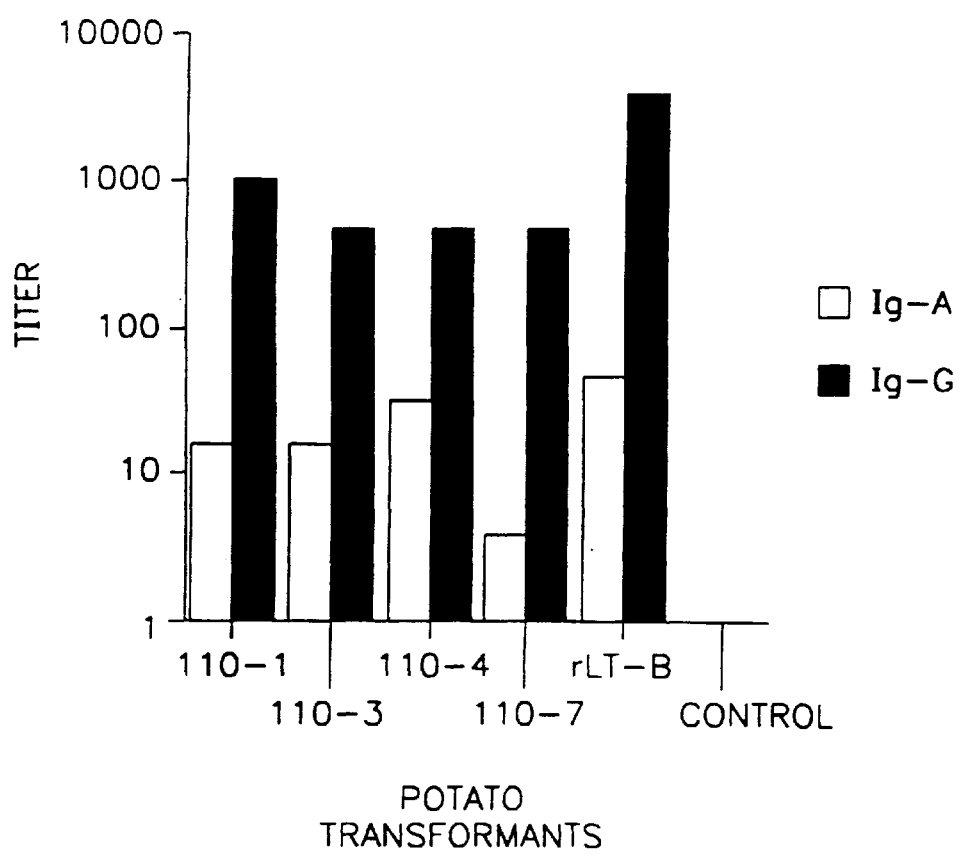

Tobacco transformant cell extracts were prepared and analyzed by size exclusion chromatography. Leaves of tobacco plants transgenic for LT-B-SEKDEL were extracted with PBS 1% Triton X-100, 2 MM PMSF and 20 mM Acorbate. After centrifugation at 12,000×g, the supernatant was loaded on a column of Sephacryl® 200, and eluted with 50 mM Tris-HCI, pH 7.5, 200 mM NaCl, 20 mM EDTA, 2 mM PMSF, 0.05% Triton X-100. Fractions were collected and assayed by ganglioside-dependent LT-B ELISA (O.D. 405 profile). A representative chromatogram is shown in FIG. 4. Arrows in FIG. 4 mark the positions of the void volume (Vo), and molecular size standards. The major antigen peak eluted at Mr 38 kDa, coincident with the position of rLF-B from $E.\ coli$.

EXAMPLE 11

This example illustrates the preparation of tobacco leaf extracts for administration to mice to induce secretory immune responses in mice GALT to the LT-B protein containing a C-terminus SEKDEL ER retention sequence (LT-B-SEKDEL).

Tobacco leaves expressing either LT-B or LT-B-SEKDEL were frozen in liquid nitrogen and homogenized in a waring blender. The soluble protein was extracted in PBST, 40mM ascorbate, 20 mM EDTA and I mM PMSF. The insoluble plant cell debris were removed by centrifugation at 15,000× g. This plant extract was precipitated with 40% ammonium sulfate at 4° C. The supernatant obtained after centrifugation at 15,000×g was further precipitated at 60% ammonium sulfate final concentration at 4° C. and the precipitate thus obtained after centrifugation at 15,00×g was solubilized in PBS and used for oral immunization studies.

EXAMPLE 12

This example illustrates the induction of an anti-LT-B serum and mucosal immune responses in mice after being fed extracts of tobacco plants transformed with a vector encoding the LT-B-SEKDEL protein.

Balb/c mice were given a soluble extra of the tobacco plant leaves of example 10 expressing the LT-B-SEKDEL. Another group of mice were given rLT-B purified from $E.\ coli$ expressing the antigen from a recombinant plasmid. An antigen equivalent dose (as determined by ELISA) of 12.5 pg was administered to each mouse by gavage on days 0, 4, 21, and 25. Serum and mucosal antibody responses were examined by ELISA for antibodies from samples collected on days 30–32. Anti-LT-B antibodies were detected in both serum as well as mucosal extracts of the sacrificed mice. Isolation of serum and mucosal extracts from mice was done by first anesthetizing the mice with Xylazine/Retamine. Serum is removed by cardiac puncture and the mice sacrificed with cervical dislocation. The small intestine is removed from the duodenum to cecum and placed in a plastic capped tube containing ice cold EDTA/STI (50 MM EDTA, 0.1 mg/mL soybean trypsin inhibitor). The intestine is homogenized in EDTA/STI using tissue homogenizer and then centrifuged at 32,000×g. The supernatant is lyophilized overnight, resuspended and dialyzed in TEAN buffer, and assayed by ELISA. ELISA for mouse IgA and IgG against LT-B: Polystyrene ELISA plates were coated with ganglioside $G_{MX}$ as described above. 100 μL of LT-B was added to each well (10 μg of LT-B/well) and incubated for 1 hr at room temperature. In a separate 96 well plate (dilution plate), two fold dilutions of a $\frac{1}{16}$ dilution of serum from immunized mice were prepared (in first well). Dilutions were taken out in at leant 12 wells (125 μL into 125 μL). Plates containing LT-B were washed four times with PBST and after final wash 100 μL of dilutions of the serum (lowest to highest concentration) from the dilution plate were applied onto the LT-B coated plate. After incubation for one hour at room temperature, the plates were washed with PBST and 100 μL of 1:4 dilution of alkaline phosphatase conjugated rabbit antiserum to mouse IgG (Sigma A1902) in PBST was added to each well. Plates were washed four times with PBST and 100 µL of 1 mg/ml nitrophenyl substrate in diethanolamine buffer was added to each well. After incubation for 10 to 30 minutes, the reaction was stopped with 25 µL of 3N NaOH per well. The absorbance of the wells was read at 410 nm. The ELISA for estimating IgA in mucosal material was similar as for IgG except that the material was probed with 1:500 dilution of goat antiserum to mouse IgA (Sigma M7144) which was in turn probed with 1:100 dilution of alkaline phosphatase conjugated rabbit antiserum to goat IgG (Sigma A7650). Values for IgG and IgA were determined from a standard curve with purified mouse myeloma proteins (MOPC 315), gA(IgA12); MOPC 21, gGi1 Litton Bionetics, Inc., Charleston, S.C.). Cross reactivity was determined by crossing reagents (i.e., IgG bound to plates to check antiserum against IgA). Cross reactivity for our reagents =2.4% for IgG and 6.7% for IgA. Values were corrected for cross reactivity. Mucosal IgA values were further corrected for contamination of mucosa with serum (Corrected Mucosal IgA=Mucosal IgA−[Serum IgA×[Mucosal IgG/Serum IgG]]). Below is the formula used to calculate the amount of antigen specific IgG (or IgA) in the unknown samples. A linear regression line is drawn for the standard and the value (in ng/ml) of the linear midpoint (assumed to be 1.0) is determined. Each unknown is then evaluated separately by taking 5 data points along the linear portion of each dilution curve, determining the slope, y intercept, and finally, the dilution that gives the absorbance value of 1.0 (i.e., linear midpoint). This dilution is then multiplied by the standard value in the product is divided by 1,000 to return a value in µg/ml.

Slope $(b)=(Sxy-[(Sx)(Sy)]/n)/(SX^2-(Sx)^2/n)$ y intercept $(a)=(Sy/n)-(Slope(b)/n)$ Log Stdx=[1.0-y intercept (a)]/slope (b)

Std (x)=Exp(Log Std (x))

EXAMPLE 13

This example illustrates the ability of antibodies of Example 12 from mice fed plant-derived LT-B-SEKDEL to neutralize enterotoxin LT.

As shown in table I, both serum and mucosal immunoglobulins from animals immunized orally with LT-B-SEKDEL transformed plant tissue were able to neutralize the biological activity of LT to the same extent as serum and mucosal antibodies from animals immunized orally with an antigen equivalent dose of bacterial rLT-B. These findings demonstrate that plant expressed antigens retain native epitopes and thereby have potential value as vaccines.

TABLE I

| ANTIBODY SAMPLES | TITER |
| --- | --- |
| Bacterial LT-B SERA | 320 |
| Plant LT-B-KDEL SERA | 320 |
| Bacterial LT-B MUCOSA | 5,120 |
| Plant LT-B-KDEL MUCOSA | 5,120 |

Neutralization of adrenal cell activity of E. Coli enterotoxin. The adrenal cell assay was conducted using mouse Y-1 adrenal cells in miniculture. A selected dose of toxin was mixed with serial dilutions of pooled sera or mucosal samples from mice orally immunized with either tobacco plant extract (Plant LT-B-KDEL) or with bacterially derived LT-B (Bacterial LT-B). Following a preincubation for one hour at 37° C., samples were applied to a monolayer of mouse YI adrenal cells (ATCC CCL79) and the incubation continued for 18 hours. Titer is defined as the reciprocal of the highest serum dilution showing complete neutralization of biological activity of 50 picograms (approximately 10 rounding doses) of toxin.

EXAMPLE 14

This example illustrates the transformation of potato with pLTK110 and selection of transgenic plants.

The T-DNA plasmid vector pLTK110 of Example 1 was used to transform potato plants using Agrobacterium-mediated transformation. The plasmid pLTK110 was first mobilized into Agrobacterium tumefaciens LBA4404 (Clonetech Laboratories, Palo Alto, Calif.) by the direct freeze-thaw method, An G. Meth. Enzymol. 153:292–305 (1987). Transformed clones were isolated by selection on 50 mg/L kanamycin, and plasmid prepared from liquid cultures by alkaline lysis. The structure of plasmids from Agrobacterium were verified by restriction endonuclease digestion. Positive clones were used for potato plant transformation as described in Wenzler H, Mignery G, May G, Park W. *Plant Science* 63, 79–85 (1989).

Potato variety FL1607 (available from Frito-Lay, Inc., Rhinelander Wis.) was cultured aseptically in sterile media containing basal medium (MS salts, 100 mg/L myo-inositol, 0.4 mg/L thiamine-HCl and 60 mM sucrose, solidified with 0.8% agar) in GA-7 vessels (Magenta Corp.), at 25° C. under diffuse fluorescent light from equal numbers of cool-white and Grow-lux (Sylvania) lamps, energy flux 10 W/m$^2$, with a 16 h light period alternating with 8 h dark. Strips of leaves 2–3 mm wide were excised under aseptic conditions from 3–4 week-old cultured shoots, and placed abaxial side down on 100×20 mm petri plates containing stage I medium (basal medium supplemented with 10 mg/L gibberellic acid, 0.2 mg/L naphthaleneacetic acid, and 2.24 mg/L 6-benzyalminopurine), and incubated for 4 days at 25° C. with 16 h light per day.

Liquid cultures of Agrobacterium were grown in 5 ml YEP medium (10 g/L Bacto-peptone, 10 g/L yeast extract, 5 g/L NaCl, pH 7.0) at 29° C. from a single colony grown on YEP medium solidified with 15 g/L agar. Leaf strips were placed for 10 minutes in a sterile petri dish containing a 1:50 dilution with sterile water of a saturated liquid culture of *A. tumefaciens* harboring the plasmid to be transferred. Excess liquid was removed by blotting the leaf strips on sterile paper towels, and the explants returned to stage I medium and incubated as above for 3–4 days until a slight ring of bacterial growth was visible surrounding the leaf explants. The explants were then transferred to GA-7 vessels containing stage I medium supplemented with 50 mg/L kanamycin sulfate and 500 mg/L carbenicillen (antibiotics were filter sterilized before use).

To produce shoots, explants were incubated as described above for 12 days, and then transferred to GA-7 vessels containing stage II medium (stage I medium lacking naphthaleneacetic acid and containing 50 mg/L kanamycin sulfate and 500 mg/L carbenicillen. When shoots containing at least 2 nodes and measuring at least 2 cm tall had formed, they were transferred to rooting medium (basal medium containing 50 mg/L kanamycin sulfate and 500 mg/L carbenicillen). When roots had formed (after approximately 2 weeks), shoots could be transferred to pots containing soil and grown in a growth chamber or green house.

In order to screen transformants for expression of the LT-B and LT-B-SEKDEL proteins in tubers, we generated microtubers in aseptic tissue culture according to Perl A, Aviv L, Willmizter L, Galum E. *Plant Science* 73:87–89

Figure 8:
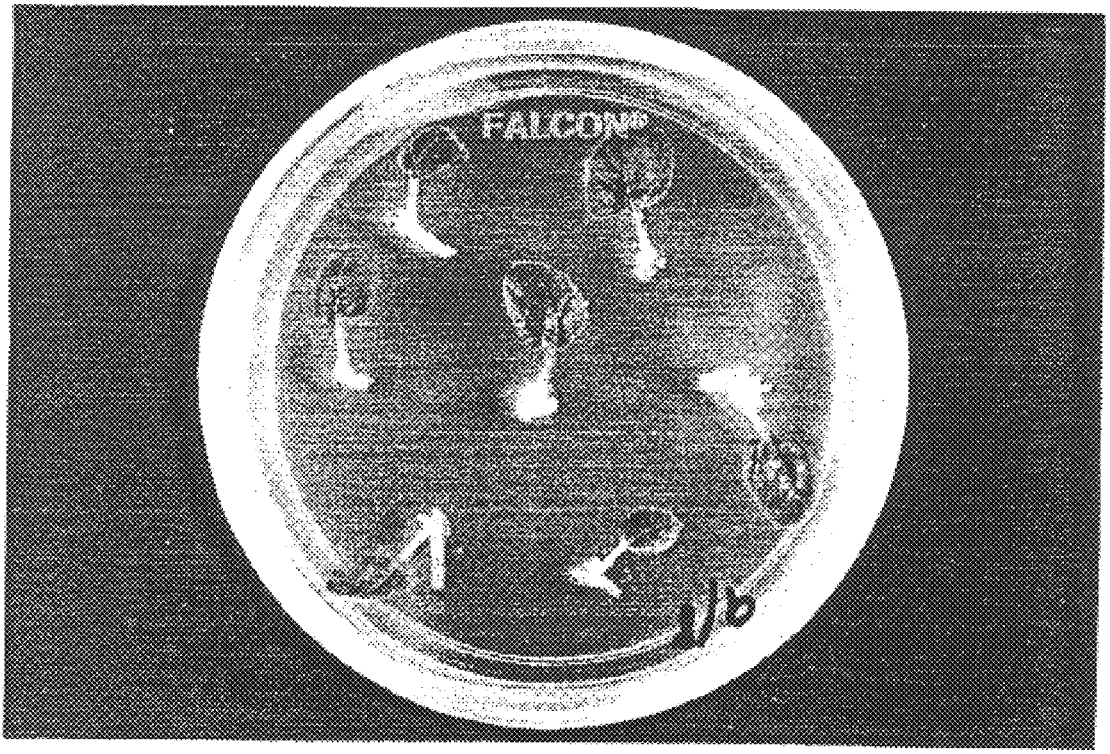

(1991). Shoots cultured on rooting medium were grown until they had 5–8 nodes, and were dissected under sterile conditions. Individual nodes were cultured in petri plates containing tuberization medium (0.5×MS salts, 8% sucrose, 5 ml/L kinetin, and 5 mg/L ancymidol [trade name A-rest, DowElanco, Indianapolis, Ind.]), in the dark at 18° C. After 2 weeks, microtubers formed at the axillary meristem, as shown in FIG. 8. The microtubers were excised and extracted as described in Example 8, and assayed for LT-B by ELISA, as described in Example 7.

EXAMPLE 15

This example illustrates the ELISA analysis of microtubers from potato plant transformants for LT-B and LT-B-SEKDEL expression.

Expression of the LT-B coding gene in microtubers from potato plant transformants was assayed by quantitation of the levels of recombinant proteins quantified by ELISA as shown in FIG. 2. ELISA levels of recombinant protein were determined from soluble protein extracts from independent potato transformants (labeled "B" in FIG. 2) which carried either the native LT-B coding region (open bars) or LT-B-SEKDEL (solid bars) coding region in which LT-B gene was modified to code for Ser-Glu-Lys-Asp-Glu-Leu (SEKDEL) endoplasmic reticulum (ER) retention sequence at the LT-B gene C-terminus. Extracts from the potato transformants in PBST (phosphate buffered saline, 2 mM PMSF, 20 mM ascorbate and 0.05% TWEEN) were spun at 12000×g and the supernatant obtained were tested by ELISA as described in Example 7. The 4 transformants showing the highest antigen levels are shown in FIG. 2.

EXAMPLE 16

This example illustrates the growth of potato plant transformants for tuber production.

Figure 9:
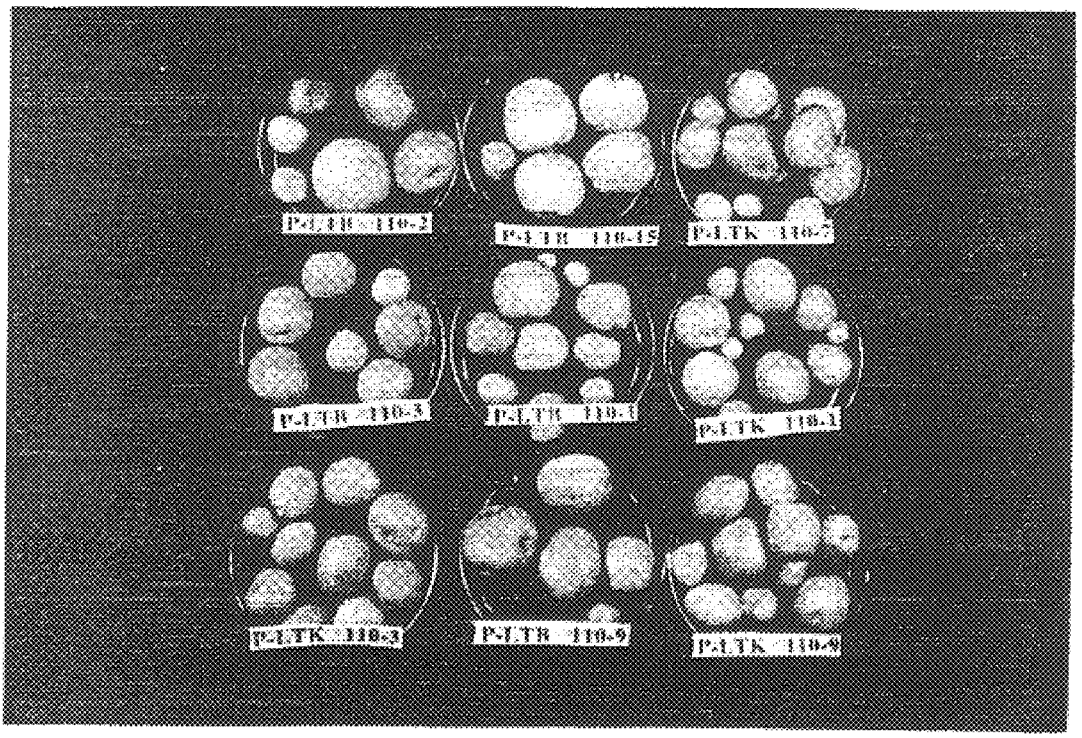

Those individual transformants whose microtubers showed the highest levels of LT-B or LT-B-SEKDEL, accumulation (as described in Example 14) were cloned by culturing the nodes aseptically on rooting medium. Rooted shoots were transferred to soil and grown in a growth chamber at 22° C. with 16 h light per day, and watered an needed with Peters Plant Starter 9-45-15 fertilizer (Hiummert Seed Co., St. Louis, Mo.). After 4–6 weeks the plants had developed to about 10 cm in height, and they were transferred to a short day growth chamber (8 h light per day) at 18° C., and watered without fertilizer. Only enough water to maintain the plants was used, because it was found that overwatering could cause rotting of the developing tubers. After 4–6 weeks, tubers varying in size from 1 cm to 4 cm in diameter had formed, as shown in FIG. 9. Tubers were removed, washed free of soil, air dried, and stored in the dark, sealed in polyethylene or paper bags at 4° C. until used for feeding studies. Tubers left in the light were found to develop a green color, which indicates that toxins are present in the skin which could be harmful if fed to animals. After removal of tubers, the plants were cultured under short day conditions as described above for further tuber development.

EXAMPLE 17

This example describes the production and selection of transgenic potato plants which are engineered to produce LT-A and LT-B within the same cells of tuber tissue.

pLT100 and pLT101 of Example 3 were used to transform Agrobacterium as described in Example 14. After verification of plasmid structure in Agrobacterium as described in Example 14, the appropriate strains were used to transform potato variety FL1607 as described in Example 14. Microtubers were generated as described in Example 14 and tested for expression of LT-A and LT-B genes by RNA blot analysis.

Total RNA was extracted from microtubers by grinding 50 mg of tissue in a 1.5 ml microcentrifuge tube with a pellet pestle in 0.25 ml of buffer (0.2 M Tris-HCl, pH 8.6; 0.2 M NaCl; 20 mM EDTA; 2% SDS). The homogenate was mixed thoroughly for 2 minutes with 0.25 ml of phenol (equilibrated with TE, pH 8.0) and 0.25 ml of CHC13, and centrifuged in a microcentrifuge at 14,000×g. The upper aqueous phase was recovered and mixed with 0.1 volume of 3 M potassium acetate, pH 4.8, and 2.5 volumes of ethanol, and stored overnight at –20° C. to precipitate nucleic acids. The samples were centrifuged at 14,00×g. for 10 minutes to pellet nucleic acids, and the pellets washed with 70% ethanol and air dried, and redissolved in 50–100 $\mu$L of sterile nuclease-free water. After determination of RNA concentration by spectrophotometric absorbance at 260 nm, 5 $\mu$g of RNA from each sample were aliquoted and denatured in 20 $\mu$L total volume containing 10 $\mu$L formamide, 3.5 $\mu$L formaldehyde, and 20 mM 3-(N-morpholino) propanesulfonic acid (MOPS), pH 7.0, 40 mM sodium acetate, 1 mM EDTA, and heated at 65° C. for 15 minutes. The samples were then mixed with 2 $\mu$L. of 50% glycerol, 20 mM EDTA, 0.25% bromophenol blue, and electrophoresed on a 1.5% agarose gel in 20 mM MOPS, pH 7.0, 40 mM sodium acetate, 1 mM EDTA,.at 80 V for 1.5 h.

The RNA in the agarose gel was then blotted to a nylon membrane (Zeta-probe, BioRad, Hercules, Calif.) by capillary blotting in 25 mM sodium phosphate, pH 6.5, for 16 hours, and cross-linked to the membrane by UV irradiation using a Stratalinker (Stratagene, La Jolla, Calif.) or by baking at 80° C. for 1 hour. RNA was visualized on the blot (in order to verify loading density) by staining with 0.25% methylene blue in 0.1 M sodium acetate, pH 5.0, and destaining with water. The membrane was then incubated for 1 hour in hybridization buffer (0.25 M sodium phosphate, pH 7.2; 1 mM EDTA; 7% SDS) at 65° C., after which the buffer was replaced with fresh hybridization buffer at 65° C., containing approximately 10 cpm/ml of random primed 32P-labelled DNA probe using coding sequences of LT-A and LT-B as template. The templates were the XhoI/SacI fragment from pLTA210 of Example 2, and the XhoI/SpeI fragment from pLTB210 of Example 1. The membrane was incubated at 65° C. for 16 hours, then washed twice with wash buffer 1 (40 mM sodium phosphate, pH 7.2; 5% SDS; 1 mM EDTA) at 65° C. for 20 minutes, and twice with wash buffer 2 (40 mM sodium phosphate, pH 7.2; 1% SDS; 1 mM EDTA) at 65° C. for 20 minutes, air dried, and exposed to Kodak X-Omat AR film with an intensifying screen for 4 days at –80° C.

Figure 10:
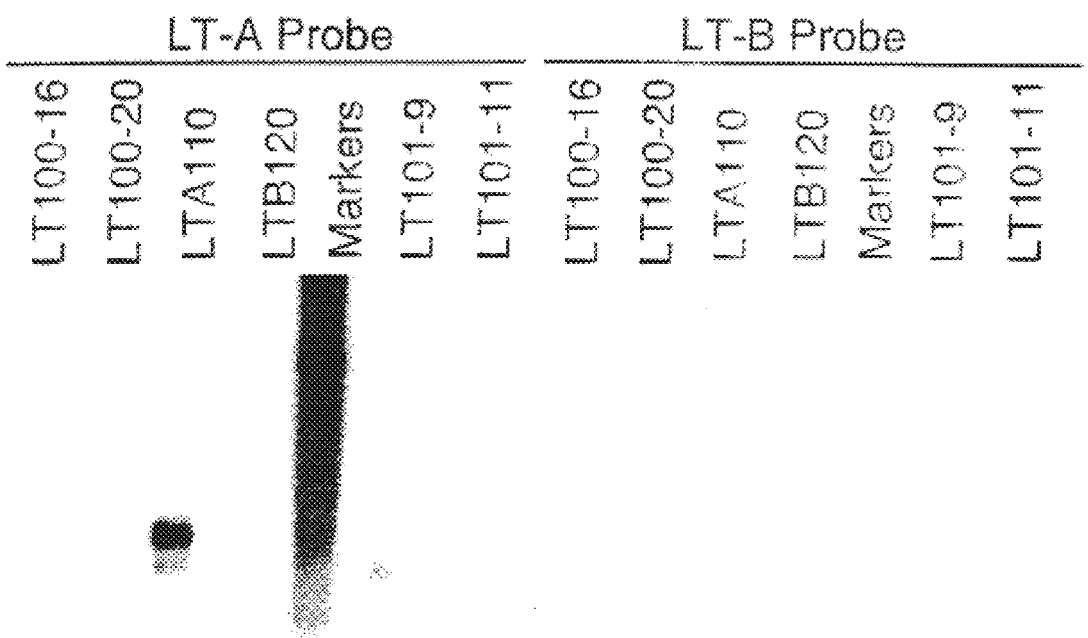

The resulting radiogram, shown FIG. 10, indicates that sequences encoding both LT-A (A-probe) and LT-B (B-probe) are present in RNA from plants transformed with pLT100 (samples 0–16, 0–20), and pLT101 (1–9, 1–11). Although the experiment is not quantitative with respect to absolute levels of mRNA encoding LT-A and LT-B, it shows that the plants transformed with pLT100 appear to have a more favorable ratio of LT-A to LT-B mRNA.

EXAMPLE 18

This example serves to illustrate a method for testing the tubers of Example 17 (above) for the presence of holotoxin LT.

Tubers (of Example 17) from plants transformed with pLT100 or pLT 101 of Example 16 are extracted and precipitated with 40% and 60% ammonium sulfate as described in Example 11. The material is then used in the adrenal Y-1 cell assay for LT, as described in Example 13.

Figure 13:
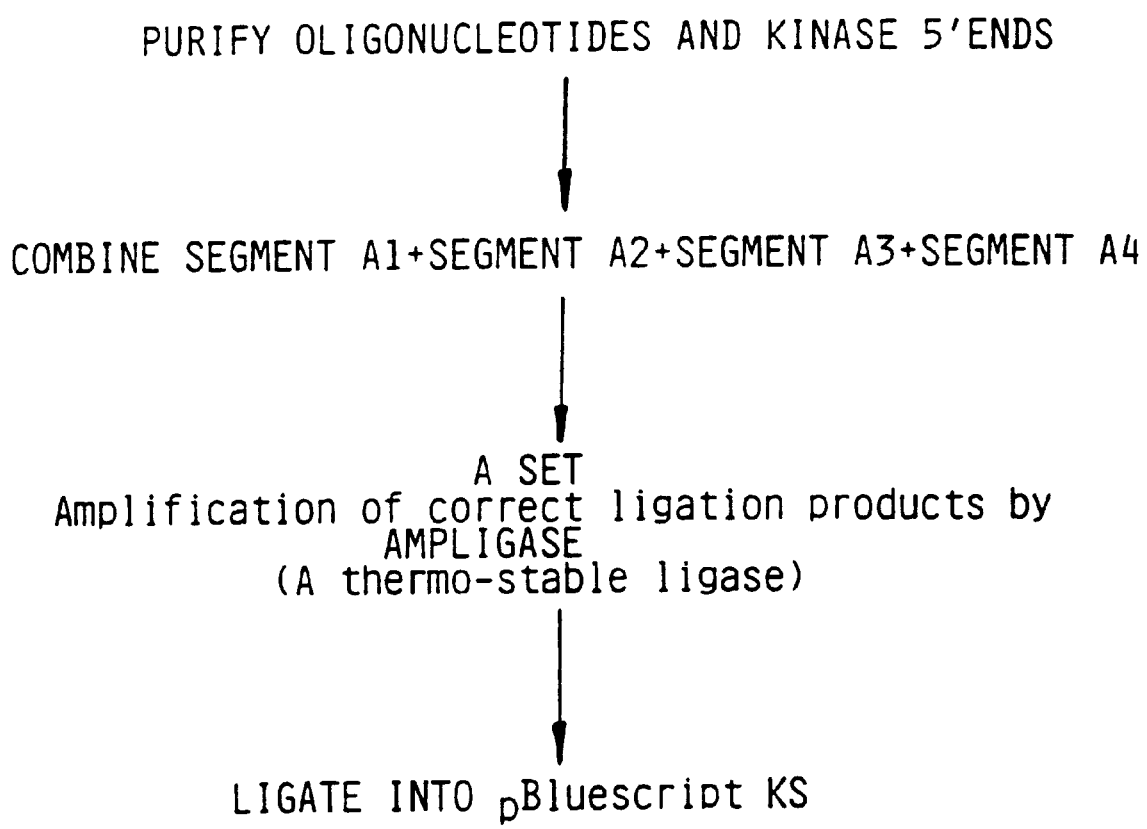

Alternatively, the extract is tested for LT-A by ganglioside-dependent ELISA, as described in Example 7, except that the antibody probe is specific for LT-A rather than LT-B.

EXAMPLE 19

This example illustrates the preparation of potato for administration to mice to induce secretory immune responses in mice GALT to the LT-B protein containing a C-terminus SEKDEL ER retention sequence (LT-B-SEKDEL).

Potato tuber feeding to mice: Groups of Balb/C mice housed individually were fed 5 grams of antigen expressing potato slices on days 0, 4, 14, and 18. The mica were taken off food and water before the feeding and until the entire 5 gram potato slices had been consumed. As a negative control, a group of mice were fed non-transformed potatoes. On day 28, animals were sacrificed and serum and mucosal materials examined for the presence of anti-LT-B antibodies by ELISA. FIG. 6 shows that mice f ed transformed tubers developed significant levels of serum IgG and mucosal IgA directed against the foreign (bacterial) antigen expressed in the tubers.

EXAMPLE 20

This example illustrates the construction of a synthetic LT-B gene, with a modified nucleotide sequence that has codons optimized for expression in plants as opposed to bacteria.

The coding sequence of LT-B was analyzed for its codon usage. It was compared with frequency of codon usage age in abundant proteins found in potato and tobacco and plants in general as shown in Table 2.

TABLE 2

| | | LT-B | | Potato | Tobacco |
|---|---|---|---|---|---|
| AA | CODON | Count | % Use | % use | % use |
| ARG | CGA | — | — | 14 | 11.2 |
| | CGC | 1 | 25 | 6.5 | 9 |
| | CGG | — | — | 4.4 | 5 |
| | CGU | — | — | 23 | 21 |
| | AGA | 2 | 50 | 28 | 27 |
| | AGG | 1 | 25 | 24 | 27 |
| LEU | CUA | 3 | 50 | 10.4 | 9 |
| | CUC | — | — | 11.6 | 16 |
| | CUG | 1 | 16.7 | 8.5 | 8 |
| | CUU | — | — | 28 | 29 |
| | UUA | 2 | 33.3 | 17 | 12 |
| | UUG | — | — | 24 | 26 |
| SER | UCA | 2 | 20 | 25 | 20 |
| | UCC | 1 | 10 | 12 | 14 |
| | UCG | 2 | 20 | 6 | 6 |
| | UCU | 2 | 20 | 27 | 30 |
| | AGC | 1 | 10 | 10 | 14 |
| | AGU | 2 | 20 | 4 | 17 |
| THR | ACA | 6 | 55 | 31 | 32 |
| | ACC | 3 | 27 | 16 | 21 |
| | ACG | 2 | 18 | 6 | 8 |
| | ACU | — | — | 47 | 39 |
| PRO | CCA | — | — | 39 | 43 |
| | CCC | 2 | 67 | 15 | 13 |
| | CCG | 1 | 33 | 7.5 | 7 |
| | CCU | — | — | 39 | 37 |
| ALA | GCA | 3 | 50 | 32 | 27 |
| | GCC | 1 | 16.6 | 15 | 21 |
| | GCG | 1 | 16.6 | 5.2 | 5 |
| | GCU | 1 | 16.6 | 47 | 47 |
| ASN | AAC | 2 | 33 | 31 | 49 |
| | AAU | 4 | 67 | 69 | 51 |
| GLY | GGA | — | — | 39 | 35 |
| | GGC | 3 | 100 | 16 | 17 |
| | GGG | — | — | 12 | 11.5 |
| | GGU | — | — | 33 | 37 |
| VAL | GUA | 1 | 25 | 16 | 15.5 |
| | GUC | 2 | 50 | 15 | 21 |
| | GUG | — | — | 23 | 22 |
| | GUU | 1 | 25 | 46 | 42 |
| LYS | AAA | 7 | 70 | 48 | 43 |
| | AAG | 3 | 30 | 52 | 57 |
| GLN | CAA | 3 | 60 | 64 | 63 |
| | CAG | 2 | 40 | 36 | 37 |
| HIS | CAC | — | — | 32 | 46 |
| | CAU | 1 | 100 | 68 | 64 |
| GLU | GAA | 7 | 70 | 60 | 51 |
| | GAG | 3 | 30 | 40 | 49 |
| ASP | GAC | 3 | 60 | 28 | 36 |
| | GAU | 2 | 40 | 72 | 64 |
| TYR | UAC | — | — | 44 | 47 |
| | UAU | 4 | 100 | 56 | 53 |
| CYS | UGC | — | — | 42 | 47 |
| | UGU | 2 | 100 | 58 | 53 |
| PHE | UUC | — | — | 36 | 43 |
| | UUU | 2 | 100 | 64 | 57 |
| ILE | AUA | 4 | 33 | 18 | 18 |
| | AUC | 3 | 25 | 26 | 28 |
| | AUU | 5 | 42 | 56 | 54 |
| MET | AUG | 4 | 100 | 100 | 100 |
| TRP | UGG | 1 | 100 | 100 | 100 |
| TER | UAA | — | — | 50 | 42 |
| | UAG | — | — | 16 | 16 |
| | UGA | 1 | 100 | 34 | 42 |

The codons of the native LT-B gene which have low or zero frequency of use in plants were modified to conform with the plant codons used in the genes for the abundantly expressed plant proteins. The segments of codons with possible poly-A signal sequences were modified to other codons for the same amino acids. The codon for aspargine, position 90, and/or threonine, position 92, in the glycosylation signal were modified to codons of other amino acids. The replacement amino acids were determined by observing the effect of residue change in the secondary structure by following Chou and Fasman structure prediction and by computer simulation in the 3-dimensional structure of LT-B. The designed gene was synthesized in stretches of ~50 nucleotides with complementary sequences and ligated together as described below.

The sequence of this newly designed LT-B gene is shown below in Table 3 along with the native gene and the amino acid sequence for which they code.

Regarding the cloning of the synthetic LT-B gene, first, FIGS. 12 and 13 show the construction of A set region composed of segments A1, A2, A3, and A4 (SEQ ID NOS: 12–15, respectively), which were prepared as follows.

FIG. 12 shows the oligonucleotides comprising the A set of fragments of the synthetic gene. The oligonucleotides synthesized to construct the designed-synthetic gene for LT-B are depicted annealed to their complementary strands. The 5' and the 3' overhangs to allow annealing and ligation to the adjacent fragments are shown. The useful restriction enzyme sites are shown to allow cloning.

FIG. 13 shows that complimentary oligonucleotides were purified by electrophoresis on a 6% urea, 12% polyacrylamide sequencing gel. The bands were observed by UV shadowing, cut out and crushed in an micro centrifuge tube. The oligonucleotides were eluted in water overnight and centrifuged at 12000×g to remove the acrylamide. The supernatant was removed and filtered through glass wool to remove any polyacrylamide. The oligonucleotides were quantified and kinased with polynucleotide kinase and ATP. Equimolar ratios of the oligonucleotides were mixed and ligated using the thermostable ligase. "Ampligase" according to the specifications by the supplier. The A set was then ligated into the KpnI and PstI sites of pKSbluescript plasmid.

Figure 14:
FIG. 14 depicts the synthetic oligonucleotides segments, B1–B4, used to create the synthetic LT-B gene.
Figure 15:
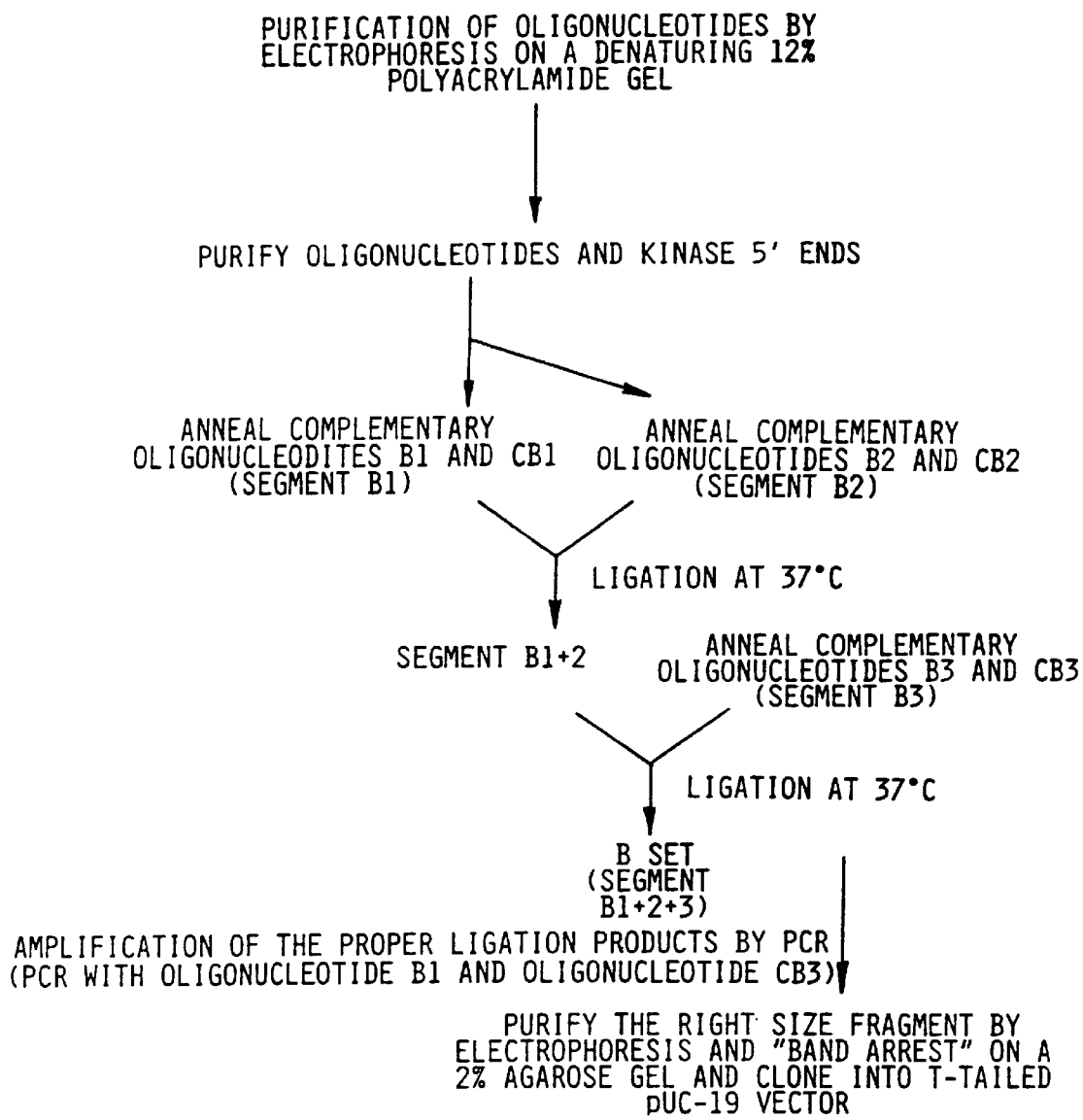
FIG. 15 depicts the process of the creation of the B set of fragments used to create the synthetic LT-B gene.
Figure 16:
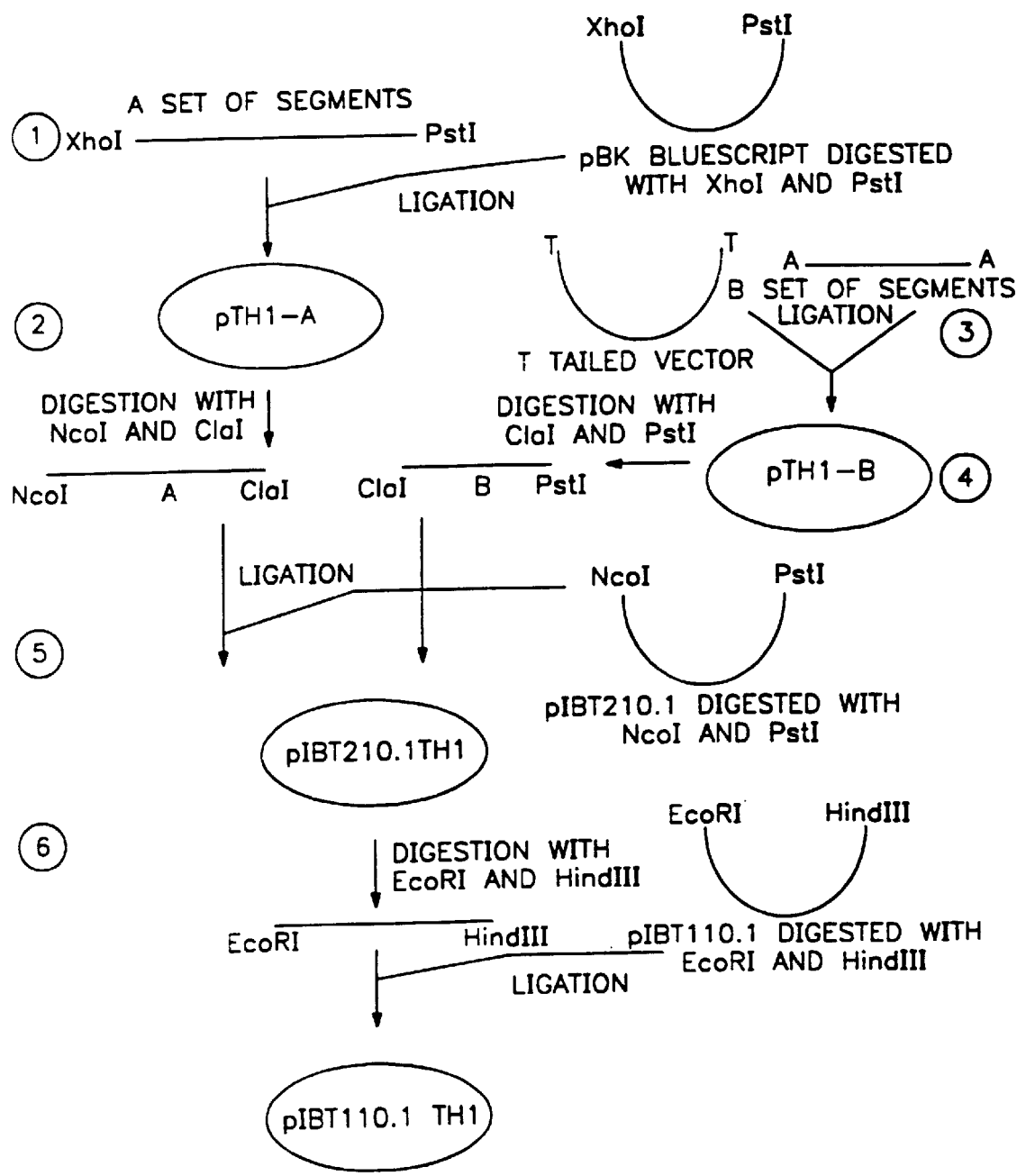
FIG. 16 depicts the process of the creation of the synthetic LT-B gene including the ligation of the A and B sets of fragments.

FIGS. 14 and 15 show the construction of a B set region of fragments composed of segments B1, B2, and B3 (SEQ ID NOS: 16–18, respectively), which were prepared as follows.

FIG. 14 shows the oligonucleotides comprising the B set of fragments of the synthetic gene. Oligonucleotides comprising the B set of fragments of the synthetic gene.

The oligonucleotides synthesized to construct the designed-synthetic gene for LT-B are depicted annealed to their complementary strands. The 5' and the 3' overhangs to allow annealing and ligation to the adjacent fragments are shown. The useful restriction enzyme sites are shown to allow cloning.

FIG. 15 shows that the complimentary oligonucleotides were purified by electrophoresis on a 6% urea, 12% polyacrylamide sequencing gel. The bands were observed by UV shadowing, cut out and crushed in an micro centrifuge tube. The oligonucleotides were eluted in water overnight and centrifuged at 12000×g to remove the polyacrylamide. The supernatant was removed and filtered through glass wool to remove any polyacrylamide. The oligonucleotides were quantified and kinased with polynucleotide kinase and ATP. Equimolar ratios of the oligonucleotides were mixed and annealed. Adjacent segments of B set were ligated to each other and the proper ligation product amplified by PCR. The PCR products were electrophoresed on 2% agarose gel and correct size fragment purified by band arrest. The B set fragment was cloned into a T tailed pUC-19 vector.

FIG. 16 then shows the construction of the LT-B expression vectors p210TH1 and p110TH1 via the following procedure: (1) the A set segment of the synthetic gene (see below) was ligated into the XhoI and PstI digested pBluescriptKS (Stratagene) to form pTH1-A. The plasmid was amplified in a Dam methylase mutant *E. coli* strain; (2) the A block was excised out with digestion with NcoI and ClaI and purified by electrophoresis on a 2% agarose gel; (3) the B set of segments was ligated into a T-tailed vector to form pTH1-B and the plasmid amplified in a Dam methylase mutant *E. coli* strain; (4) the B set was excised with digestion with ClaI and PstI and purified by electrophoresis on a 2% agrose gel; (5) the A and the B set were ligated in to the pIBT210.1 vector digested with NcoI and PstI to form pIBT210.1TH1; and (6) the expression cassette from pIBT210.1TH1 was digested by EcoRI and HindIII and ligated into the EcoRI and HindIII sites of Agrobacterium T-DNA vector pIBT110.1 to form pIBT110.1TH1.

Table 3 shows the sequence of the newly designed LT-B gene along with the native gene and the amino acid sequence for which they code. The table shows the comparison of the native LT-B gene (N) and designed LT-B gene (D). Codons were modified to be consistent with the codon usage in plants for the particular amino acid. The base changes are indicated by bold letters. The amino acid sequence is shown below the native gene sequence. The box represents the putative poly-adenylation signal sequence in the native gene. Sequence coding for the mRNA destabilizing sequence AUUUA in the native gene is underlined. AT rich regions were modified to remove potential mRNA destabilizing sequences or cryptic splice sites. The genes are shown without the sequence encoding the bacterial leader peptide.

TABLE 3

| | | | | | | | | | | | | | | | | |
|---|---|---|---|---|---|---|---|---|---|---|---|---|---|---|---|---|
| N | GCT | CCC | CAG | TCT | ATT | ACA | GAA | CTA | TGT | TCG | GAA | TAT | CGC | AAC | ACA | CAA |
| D | GCT | CCA | CAA | TCC | ATC | ACT | GAG | CTT | TGC | TCT | GAG | TAC | AGG | AAC | ACT | CAG |
| | Ala | Pro | Gln | Ser | Ile | Thr | Glu | Leu | Cys | Ser | Glu | Tyr | Arg | Asn | Thr | Gln |
| | 1 | 2 | 3 | 4 | 5 | 6 | 7 | 8 | 9 | 10 | 11 | 12 | 13 | 14 | 15 | 16 |
| | | 54 | | 63 | | | 72 | | | 81 | | 90 | | | | |
| N | ATA | TAT | ACG | ATA | AAT | GAC | AAG | ATA | CTA | TCA | TAT | ACG | GAA | TCG | ATG | GCA |
| D | ATC | TAC | ACC | ATC | AAT | GAC | AAG | ATC | CTC | TCT | TAC | ACT | GAG | AGC | ATG | GCT |
| | Ile | Tyr | Thr | Ile | Asn | Asp | Lys | Ile | Leu | Ser | Tyr | Thr | Glu | Ser | Met | Ala |
| | 17 | 18 | 19 | 20 | 21 | 22 | 23 | 24 | 25 | 26 | 27 | 28 | 29 | 30 | 31 | 32 |
| | 99 | | 108 | | | 117 | | | 126 | | 135 | | | 144 | | |
| N | GGC | AAA | AGA | GAA | ATG | GTT | ATC | ATT | ACA | TTT | AAG | AGC | GGC | GCA | ACA | TTT |
| D | GGC | AAG | AGG | GAG | ATG | GTG | ATC | ATC | ACC | TTC | AAG | TCA | GGA | GCC | ACT | TTC |
| | Gly | Lys | Arg | Glu | Met | Val | | Ile | Ile | Thr | Phe | Lys | Ser | Gly | Ala | Thr |

TABLE 3-continued Phe

|     | 33  | 34  | 35  | 36  | 37  | 38  | 39  | 40  | 41  | 42  | 43  | 44  | 45  | 46  | 47  | 48  |
|-----|-----|-----|-----|-----|-----|-----|-----|-----|-----|-----|-----|-----|-----|-----|-----|-----|

|   | 153 |     | 162 |     |     | 171 |     |     | 180 |     |     |     | 189 |     |
|---|-----|-----|-----|-----|-----|-----|-----|-----|-----|-----|-----|-----|-----|-----|
| N | CAG | GTC | GAA | GTC | CCG | GGC | AGT | CAA | CAT | ATA | GAC | TCC | CAA | AAA | AAA | GCC |
| D | CAG | GTG | GAG | GTT | CCA | GGC | TCA | CAA | CAC | ATC | GAT | TCC | CAG | AAG | AAG | GCC |
|   | Gln | Val | Glu | Val | Pro | Gly | Ser | Gln | His | Ile | Asp | Ser | Gln | Lys | Lys | Ala |
|   | 49  | 50  | 51  | 52  | 53  | 54  | 55  | 56  | 57  | 58  | 59  | 60  | 61  | 62  | 63  | 64  |

|   | 198 |     | 207 |     |     | 216 |     |     | 225 |     |     | 234 |     |     |
|---|-----|-----|-----|-----|-----|-----|-----|-----|-----|-----|-----|-----|-----|-----|
| N | ATT | GAA | AGG | ATG | AAG | GAC | ACA | TTA | AGA | ATC | ACA | TAT | CTG | ACC | GAG | ACC |
| D | ATT | GAG | AGG | ATG | AAG | GAC | ACC | TTG | AGG | ATC | ACC | TAC | CTC | ACT | GAG | ACC |
|   | Ile | Glu | Arg | Met | Lys | Asp | Thr | Leu | ArG | Ile | Thr | Tyr | Leu | Thr | Glu | Thr |
|   | 65  | 66  | 67  | 68  | 69  | 70  | 71  | 72  | 73  | 74  | 75  | 76  | 77  | 78  | 79  | 80  |

|   | 243 |     | 252 |     | 261 |     |     | 270 |     |     | 279 |     |     | 288 |     |
|---|-----|-----|-----|-----|-----|-----|-----|-----|-----|-----|-----|-----|-----|-----|-----|
| N | AAA | ATT | GAT | AAA | TTA | TGT | GTA | TGG | AAT | AATAAA | ACC | CCC | AAT | TCA | ATT |
| D | AAG | ATT | GAC | AAG | CTC | TGT | GTG | TGG | AAC | AAC | AAG | ACT | CCA | AAC | TCC | ATT |
|   | Lys | Ile | Asp | Lys | Leu | Cys | Val | Trp | Asn | Asn | Lys | Thr | Pro | Asn | Ser | Ile |
|   | 81  | 82  | 83  | 84  | 85  | 86  | 87  | 88  | 89  | 90  | 91  | 92  | 93  | 94  | 95  | 96  |

|   | 297 |     |     | 306 |     |     |     |
|---|-----|-----|-----|-----|-----|-----|-----|
| N | GCG | GCA | ATC | AGT | ATG | GAA | AAC | TGA |
| D | GCT | GCC | ATC | AGC | ATG | GAG | AAC | TAA |
|   | Ala | Ala | Ile | Ser | Met | Glu | Asn | Ter |
|   | 97  | 98  | 99  | 100 | 101 | 102 | 103 | 104 |

Table 4 shows a comparison of the native LT-B gene and the designed-synthetic gene in terms of the AT content, the number of CG doublets and the TA doublets. Note that "N" is SEQ ID NO: 19, "D" is SEQ ID NO: 20 and the amino acid sequence is SEQ ID NO:21.

TABLE 4

| | % AT | CG DOUBLETS | CG DOUBLETS |
|---|---|---|---|
| NATIVE LT-B GENE | 62.9 | 14 | 47 |
| SYNTHETIC LT-B GENE (TH1) | 51.2 | 1 | 7 |

EXAMPLE 21

This example illustrates the construction of an expression vector for LT-B which lacks the bacterial signal sequence for facilitation of the insertion of plant-preferred ER signal sequences flanked by NcoI sites.

The bacterial signal sequence on the LT-B coding sequence was removed and a NcoI site inserted at the site of the mature processed N-terminus of LT-B by PCR-mediated mutagenesis as follows. A 104 bp PCR fragment was obtained using pDF82 as template and the primers 5'GGGGCCATGGCTCCCCAGTCTATT-3' (SEQ ID NO: 22) (NcoI site is underlined) and 5'TGCCATCGATTCCGTATA-3' (SEQ ID NO: 23). The PCR fragment was digested with NcoI and ClaI, and ligated with pLTB210 of Example 1 digested likewise and purified to remove the bacterial signal sequence, to give pLTB212. The entire expression cassette in pLTB212, including the 35S promoter, TEV leader, LT-B coding sequence lacking the bacterial signal sequence, and the vpsB polyadenylation signal and 3' flanking sequence, was obtained by digestion with HindIII and EcoRI, and ligated with pBI101 likewise and purified to remove the GUS coding sequence, to give pLTB112. Thus, pLTB112 is a T-DNA vector for the Agrobacterium-mediated transformation of plant cells, using selection on kanamycin-containing media.

A similar construct with the C-terminus of LT-B modified to contain SEKDEL is made by substitution with pLTK210 of Example 1 for pLTB210.

EXAMPLE 22

This example illustrates the construction of an expression vector for LT-B or LT-B-SEKDEL containing a plant-preferred ER signal sequence at the N-terminus.

A plasmid containing the ER signal sequence of soybean vegetative storage protein VSPa (Mason et al., 1988. *Plant Mol. Biol*, 11, 845) on a 66 bp NcoI fragment, paSIG-GUS, is available from H. Mason, Institute of Biosciences & Technology, Texas A&M University, Houston, Tex. 77030. paSIG-GUS is digested with NcoI, and the 66 bp fragment is purified and ligated with pLTB212 or pLTK212 of Example 21) digested with NcoI. The resulting plasmids, pLTB213 and pLTK213, are screened for the proper orientation of the insert by DNA sequencing, using primers derived from the flanking sequences. The entire expression cassettes in pLTB213 and pLTK213 are obtained by digestion of the plasmids with HindIII and EcoRI, and ligated with pBI101 digested likewise and purified to remove the GUS coding sequence, to give pLTB113 and pLTK113. Thus, pLTB113 and pLTK113 are T-DNA vectors for the Agrobacterium-mediated transformation of plant cells, using selection on kanamycin-containing media.

EXAMPLE 23

This example illustrates the construction of vectors for the expression in plants of fusion proteins composed of the LT-B protein and other antigenic determinants, either with or without a C-terminal SEKDEL for ER retention.

Plasmid pLTB210 (of Example 1) is digested with SpeI and ligated with a synthetic DNA fragment encoding foreign antigenic determinant made by annealing oligonucleotides such that a blunt end is formed on the N-terminal coding cide of the foreign insert, while a SpeI-complimentary site is formed on the C-terminal coding side of the foreign insert (as shown for SEKDEL addition in Example 1). If a C-terminal SEKDEL is desired, the synthetic oligonucleotides used will contain the appropriate nucleotides encoding SEKDEL at the C-terminus of the foreign insert. The resulting ligation products are digested with mung bean nuclease to convert the remaining SpeI site at the 3' end of the LT-B coding sequence to a blunt end, and ligated again to circularize the plasmid. It is necessary to design the synthetic fragment so that the fusion of the foreign antigen is in the same reading frame as the LT-B coding sequence. The resulting plasmids are screened for orientation of the insert, which can ligate in either the forward (preferred) or reverse orientation, and for correct reading frame fusion, by DNA sequencing, using primers which flank the insert site. Plasmids with correct fusions are then amplified and used for transient expression studies an described in Example 24.

For stable expression, LT-B fusion expression cassettes described in the preceding paragraph are obtained by digestion of the fusion plasmids with HindIII and EcoRI, and ligation with pBI101 digested likewise and purified to remove the GUS coding sequence. The resulting plasmids are used for transformation of *A. tumefaciens* LBA4404 as described in Example 6, and the resulting *A. tumefaciens* strains are used for transformation of tobacco as described in Example 6, or potato as described in Example 14.

EXAMPLE 24

This example illustrates the transient expression in protoplasts using the expression vectors of Example 23.

The half life of fusion proteins are determined using transient expression of gene constructs and pulse-chase labeling of leaf protoplasts as described. Suspension culture of plant cells in their exponential phase of growth or leaves are used to derive protoplasts (Power and Davey, Methods in Molecular Biology, Vol. 6, Plant Cell and Tissue Culture, J. W. Pollard and J. M. Walker, eds., pp. 237–259 (1990)). Epidermis of the leaves from aseptically grown tobacco or potato plants (see Example 6) are removed and the leaf pieces floated on enzyme solution (Meicelase 1.5%, Macerozyme, 0.05%, Pectolyase 0.1%, 0.4 M glucose in plant culture medium). After incubation, the leaf pieces are squeezed and the protoplast suspension transfered to centrifuge tubes. After centrifugation at 100×g the protoplast suspension is removed from the surface and utilized for transient expression of introduced genes by electroporation. The viability of protoplasts is determined by staining with fluorescein diacetate.

The protoplasts are washed in HBS (HEPES buffered saline: 150 mM LCl, 4 mM CaC12, 10 mM HEPES (pH 7.2) and mannitol. Equal volumes of protoplasts are mixed with supercoiled plasmid carrying constructs of gene fusions and transferred to a sterile electroporation chamber and voltage applied across the chamber. The electroporated protoplasts are resuspended in culture medium and incubated at 28° C.

The protoplasts pulse labeled are mixed and cultured with a $^{35}$S-Met/$^{35}$S-Cys containing medium to allow expression of labeled proteins. The cultured protoplast are then chased with an unlabelled Met/Cys mixture for different intervals of time. The protoplasts are then collected by centrifugation and extracted. The protein samples are immunoprecipitated with specific antisera against the expressed protein and/or signal sequences. Immunoprecipitates are then fractionated by poly-acryl-amide gel electrophoresis. The bands in the gels are detected and quantified by using phosphor imager.

EXAMPLE 25

This example illustrates the antigenicity and ligand binding of recombinant proteins derived from the transformants of Example 23.

The antigenicity and ligand binding capabilities of recombinant fusion proteins are analyzed by competitive ganglioside binding assays. Different dilutions of recombinant proteins are mixed with constant concentrations of biotin labeled LT and incubated with ganglioside (GMx) adsorbed on ELISA plates. The plates are subsequently washed and incubated with horseradish peroxidase conjugated strepavidin. The peroxidase is detected using its substrate ABTS. The absorbance are determined spectrophotometrically and the resulting mean absorbance of each dilution plotted against the concentration of the competitor.

EXAMPLE 26

This example illustrates the expression of hepatitis B surface antigen (HBsAg) in potato tubers, and feeding of recombinant tubers to mice for testing of immunogenic responses.

The HBsAg expression vector pHB102 (Mason et al., 1992. *Proc. Natl. Acad, Sci, USA*, 89,11745) was used to transform potato variety FL1607 as described in Example 14. Potato tubers were obtained from selected transformants which showed approximately 0.01% of the soluble tuber protein as HBsAg.

For testing of oral immunogenicity of the tuber material expressing HBsAg, the tubers are prepared and fed to mice as described in Example 19, except that 10 ug of cholera toxin (CT) are added per dose as an oral adjuvant. The mice are tested for serum and mucosal immunoglobulin production as described in Example 12. At least 25% of the mice are found to demonstrate an immune response to HBsAg when compared to standard controls.

EXAMPLE 27
Chicken Feeding with LTK110-4 tubers

Chickens and other fowl comprise a sizeable market for animal vaccines for protection against bacterial, fungal, and viral diseases which substantially limit production. As a test in fowl for the ability of food-borne anigens to cause immune responses, we have fed to chicks raw transgenic potato tubers expressing the *Escherchia coli* heat-labile enterotoxin B-subunit (LT-B), and subsequently assayed the serum from these chicks for IgG specific for LT-B. One-day-old Leghorn B12/B12 syngenic chicks were given tubers from transgenic potato line LTK110-4 (Haq. et al., 1995), containing approximately 5 μg LT-B per gram of tuber weight. Food was withheld from the chicks for 4–6 hours before feeding the potatoes. The potatoes were chopped into 1–2 mm pieces and the chicks could eat them very well. On days 0, 4, 14 and 18, 5 g of transgenic potato tuber was given to each chick, and on day 28, blood was obtained from chicks and serum prepared. The serum was assayed for anti-LT-B by the method of Cardenas & Clements (1993, *Infect. Immun.* 61:4629–2636) as follows.

ELISA FOR Anti-LT-B
REAGENTS
Coating buffer: per 300 ml-0.48 g $Na_2CO_3$, 0.88 g $NaHCO_3$, 0.06 g $NaN_3$ (pH=9.6) Store at 4° C. for not more than 2 weeks.
PBS: 10X Concentrated, per liter—15 g $Na_2HPO_4$, 61.2 g Nacl(pH of 1X=7.2)
PBS: PBS+0.05% Tween-20 1N $H_2SO_4$
GMx. sigma Type III (G2375). Add 2.5 ml $H_2O$ to 25 mg to make 10 mg/ml. Store at −20° C. Dilute 1:100 with coating buffer to make plates.
LT-B: Reconstitute lyophilized powder to the indicated volume with sterile distilled water, store at 4° C. Final buffer is 0.05 M Tris, 1 mM EDTA, 3 mM $NaN_3$, 0.2 M NaCl (pH 7.5). Rabbit anti-chicken IgG HRP conjugate (Sigma A9046) Slow TMB substrate (Pierce 34024)
PROCEDURE
1. Coat microtiter plates (polyvinylchloride), with 75 μl/well (1.5 μg) of diluted Gmx (20 μg/ml) in coating buffer. Incubate 1 h at RT.
2. Wash 3X with PBST.
3. Block wells with 200 μl/well of 5% dry milk (DM) in PBST, 37° C. for 1 h.
4. Wash 3X with PBST.
5. Add LT-B diluted to 13.3 μg/ml in PBST, 75 μl (1 μg) per well. Incubate 23° C. for 1 h.
6. Wash 3X with PBST.
7. Add 75 μl/well serum samples diluted (1:25, 1:50, 1:100, 1:200, 1:400) in 2% DM/PBST. Incubate at 4° C. overnight or 16 h.
8. Wash 4X with PBST.
9. Add 75 μl/well of rabbit anti-chicken IgG-HRP conjugate diluted 1:1000 in 2% DM/PBST. Incubate 2 h at 37° C.
10. Wash 4X with PBST.
11. Add 75 μl/well of slow TMB substrate. Incubate at RT for 15–30 min.
12. Add 75 μl/well of 1 N $H_2SO_4$.
13. Read absorbance at 450 nm. The serum samples from four different chicks were diluted as described above and assayed in duplicate, and the results averaged and shown in Table 1.

TABLE 5

Anti-LT-B ELISA on Chick Sera

| | Abs. at 450 nm for dilution | | | | |
|---|---|---|---|---|---|
| Sample | 25 | 50 | 100 | 200 | 400 |
| A | 0.470 | 0.370 | 0.233 | 0.134 | 0.067 |
| B | 0.038 | 0.019 | 0.012 | 0.007 | 0.007 |
| C | 0.473 | 0.454 | 0.383 | 0.305 | 0.214 |
| D | 0.027 | 0.018 | 0.011 | 0.008 | 0.005 |

The data show that two of the four chicks which at the LT-B containing tubers developed a strong humoral IgG response against LT-B. This result shows that chickens can be immunized against a foreign antigen expressed in an edible tissue of transgenic plants simply by eating the uncooked plant tissue.

EXAMPLE 28
Co-Ordinate Expression of LT-B-SEKDEL and Norwalk Virus Capsid Protein This example describes the analysis of potato plants which were formed with pLTK-NV of Example 5. RNA blot analysis was performed on leaf RNA samples from 19 independent transformants, using a LT-B coding region probe and the method of Mason et al., 1992, *Proc. Natl Acad. Sci. USA* 89:11745–11749. The 6 transformants that showed the highest levels of LT-B RNA were further propagated and induced to form microtubers as described in Example 14.

We made soluble extracts of the microtubers and performed ELISA assays for Norwalk virus capsid protein (NVCP). The NVCP ELISA was done as described earlier (Jiang, X., Wang, M., Graham, D. Y., and Estes, M. J., 1992, *J. Virol* 66, 6527–6532), using rabbit anti-i-rNv as the capture antibody and guinea pig anti-i-rNV as the detector antibody. Rabbit anti-serum diluted 1:10,000 in 0.01 M phosphate-buffered saline (PBS) (50 μl/well) was bound to 96-well polyvinylchloride microtiter plates for 4 h at 23° C., and then blocked with 5% nonfat dry milk in PBS (DM/PBS) for 1 h at 37° C. After washing the wells 3 times with PBS+0.05% Tween-20 (PBST), samples (50 μl/well) diluted in PBS were added, and incubated 16 h at 4° C. The wells were washed and incubated in succession with guinea pig anti-NVCP serum and rabbit anti-guinea pig IgG-HRP conjugate, each diluted 1:5000 in 2% DM/PBS, for 2 h at 37° C. The plate was developed with Slow TMB substrate (Pierce) for 15–20 min at 23° C., the reaction ended by addition of an equal volume of 1 N $N_2SO_4$, and the absorbance read at 450 nm. For a standard curve, NVCP prepared in a baculovirus-infected insect cell system (Jiang, X., Wang, M, Graham, D.Y ., and Estes, M. K., 1992, *J. Virol* 66, 6527–6532), was diluted with PBS to concentrations between 1.4 and 45 ng/ml and processed as above. The microtuber extracts were also assayed for total protein using the Coomassie dye-binding assay (BioRad) with bovine serum albumin as a standard, and the level of NVCP expressed as μg per mg total protein (Table 6).

TABLE 6

Levels of NVCP in microtubers of pLTK-NV transformants

| Transformant | μg NVCP per g total protein |
|---|---|
| 4 | 540 |
| 8 | 540 |
| 10 | 400 |

TABLE 6-continued

Levels of NVCP in microtubers of pLTK-NV transformants

| Transformant | μg NVCP per g total protein |
|---|---|
| 13 | 850 |
| 17 | 180 |
| 19 | 760 |

Plant of each transformant were transplanted to soil and grown in a controlled environment chamber to develope tubers as in Example 16. Tubers obtained from each transformant were weighed, and tubers of similar size (6 to 8 grams) were washed and peeled, and a sample of the storage parenchyma from each tuber was weighed and extracted in 4 ml per grala of buffer (25 mM sodium phosphate, pH 6.6; 100 mM NaCl; 25 mM sodium ascorbate; 5 mM EDTA; 0.1% Tween-20; 1.0 μg/ml leupeptin). The extracts were diluted with PBST and assayed by ELISA for LT-B and NVCP, and for total protein as described above, and the results expressed as μg antigen per gram of tuber mass or μg antigen per gram of total protein (Table 7).

TABLE 7

Levels of LT-B-SEKDEL and NVCP in tubers of pLTK-NV transformants

| Transformant | LT-B-SEKDEL | NVCP |
|---|---|---|
| ug antigen per gram of tuber tissue | | |
| 4 | 2.20 | 1.73 |
| 10 | 3.73 | 2.07 |
| 13 | 5.02 | 4.18 |
| 17 | 5.17 | 0.0 |
| 19 | 2.00 | 2.81 |
| ug antigen per gram of tuber protein | | |
| 4 | 205 | 160 |
| 10 | 390 | 215 |
| 13 | 625 | 520 |
| 17 | 585 | 0 |
| 19 | 290 | 400 |

These data show that L-TB-SEKDEL levels in pLTK-NV transformants selected for high LT-B mRNA expression are higher than those previously reported in Example 15 and FIG. 2. The highest level of LT-B-SEKDEL in microtubers of pLTK110 transformants was 120 μg per gram microtuber protein, while pLTK-NV transformants showed between 205 and 625 μg per gram tuber protein. This may be an effect of transcriptional enhancement due to the proximity of the patatin promoter downstream of the LT-B-SEKDEL cassette in pLTK-NV, but no data is now available to assess this. Further, NVCP accumulated in the same tubers to levels up to 4.18 μg per gram of tuber mass, and 520 μg per gram of total tuber protein. In all transformants except number 17, LT-B-SEKDEL and NVCP accumulated to similar levels. Thus, it is clear that multiple antigens can be expressed in the same trancganic plants, demonstrating the use of LT-B exressing plants as adjuvants for the immunization of other antigens.

EXAMPLE 29
Immunogenicity and Adjuvanticity of LT-B-SEKDEL Expressed in Potato Tubers This example illustrates the use of transgenic potato tubers expressing LT-B-SEKDEL as an adjuvant in chickens when provided orally with a herologous antigen (in this case, a virus), and further illustrates the immunogenicity in chickens of potato tubers expressing LT-B-SEKDEL.

The virus used in this study was the Ulster strain of Newcastle disease virus (NDV). It was ilolated in Ulster in 1967 (McFerran, et al. 1968. Vet. Rec. 82:589) and has been used in a few studies as an "enterotropic, non-pathogenic NDV" (Cheville, et. al. 1972. Vet. Path 9, 38–52; Russell, P. H. 1994. Vet. Immuno and Immunopathology 42: 357–365.) It has also been developed recently as a vaccine in Europe Van Eck and Goren, 1991, Avian Pathology 20: 497–507. NDV is a paramyxovirus, negative sensed single stranded RNA which infects all orders of birds and is distributed more or less worldwide. These are 3 varieties of NDV, lentogens (low pathogenic like the Ulster) mesogens (intermediate pathogens) and velogens (highly pathogenic).

We performed the following experiment. Potato tubers (Examples 14 and 16, transformant LTK110-4) transformed with pLTK110 of Example 1, or control untransformed potato tubers (FK1607, Example 14) were peeled and homogenized by blending for 30 seconds in a aring blender. The LTK110-4 tubers contained approximately 2.5 μg of LT-B-SEKDEL per gram of tuber mass. In some cases the tuber slurry was mixed with Necastle disease virus ($10^9$ virus per dose). The mixtures were delivered by gavage using a 10-ml plastic pipet to white leghorn chickens, mixed sex, 4-weeks old at day 1. Doses containing 10 ml were given on days 1, 2, 3, 8 and 10, and the birds were bled by wing venipuncture on day 14. The sera obtained were diluted and used to measure hemagglutinin inhibition activity (Beard, C. W., S. R. Hopkins, and J. Hammond. 1975. "Preparation of Newcastle disease virus hemagglutinin-inhibition test antigen". Avian Diseases 19:692–699.) and to assay IgG specific for LT-B, as described above in Example 27. Each group contained 5 individual birds.

A. Immunga Ragnn against NDV

The data for hemagglutinin inhibition activity, which indicates the antibody response specific for NDV hemagglutinin protein, were obtained as the highest dilution of sera that gave activity. The dilution factors for all birds in a group were used to calculate the geometric mean titer (GMT) for that group by 1) obtaining the $\log_{10}$ for each dilution factor, 2) determining the mean and standard deviation for the log10 values, and 3) obtaining the antilogs of the mean and standard deviation. Table 8 shows the date for birds which received $10^9$ virus with 4 g control tuber (Group 1), $10^9$ virus with 1 g of LTK110-4 tuber (Group 2), and 4 g of LTK110-4 tuber without virus (Group 3).

TABLE 8

Hemagglutinin Inhibition Activity in Sera of Chickens Gavaged with NDV with or without LTK110-4 Potato Tubers
Geometric mean of highest dilution showing activity ± standard deviation

| Group 1 | Group 2 | Group 3 |
|---|---|---|
| $10^9$ virus | $10^9$ virus | No virus |
| 4 g control tuber | 1 g LTK110-4 tuber | 4 g LTK110-4 tuber |
| 16.65 ± 4.96 | 40 ± 2.34 | 0 |

These data indicate that the addition of 1 g of transgenic tuber containing approximately 2.5 μg of LT-B-SEKDEL per oral dose of NDV increased the immune response against NDV. Thus, LT-B-SEDEL expressed in potato tubers has potential value as an oral adjuvant for edible vaccines in birds.

B. Immune Response against LT-B

We measured the serum antibody response against LT-B in the experiment described in Table 8, in order to show the value of the transgenic LTK110-4 tubers as a potential vaccine against *E. coli*-related diarrheal disease. These data are presented in Table 9 as absorbance values for the ELISA of serum samples diluted 1:100.

TABLE 9

Serum Anti-LT-B IgG Responses in Chickens
Gavaged with LTK110-4 Potato Tubers

| | A450 of assay, 14 day Individual Sera | | | | | Gnp Mean |
|---|---|---|---|---|---|---|
| Group 1 | | | | | | |
| 4 g control tuber + $10^9$ virus | 0.063 | 0.015 | 0.019 | 0.015 | 0.024 | 0.028 |
| Group 2 | | | | | | |
| 1 g LTK110-4 tuber + $10^9$ virus | 0.006 | 0.037 | 0.259 | 0.446 | 0.304 | 0.210 |
| Group 3 | | | | | | |
| 4 g LTK110-4 tuber + No virus | 0.193 | 0.542 | 0.385 | 0.503 | 0.500 | 0.425 |

These data show that as little as 1 g of transgenic LTK110 potato tubers, containing approximately 2.5 μg of LT-B-SEKDEL per oral dose, stimulated a significant anti-LT-B 1 gG response in the sera of 3 of 5 birds in Group 2. Further, the presence of the NDV in oral doses in Group 2 did not interfere with the response against the LT-B-SEKDEL. In Group 3, an increased dose of 4 g of transgenic LTK110 potato tubers, containing approximately 10 μg of LT-B-SEKDEL per oral dose, caused a response in all 5 birds, and increased the average intensity of the response. Thus, LT-B-SEDEL expressed in potato tubers has potential value as an oral edible vaccine against *E. coli*-related diarrheal disease in birds.

EXAMPLE 30
Enabling Quality of Plant Expression Vector Modifications

This example describes data which show that modifications of commercially available plant expression vectors can enhance expression of foreign genes.

The initial plasmid vector that we constructed for LT-B expression in plants yielded little or no measureable LT-B protein in stably transformed tobacco plants. This construct (pLTB120) utilized the genetic regulatory elements present in the commercially available plant expression vector pBI121 (Clonetech, Palo Alto, Calif.; Jefferson et al., 1987, EMBO J. 6:3901–3907), including the cauliflower mosaic virus 35S promoter and the nopaline synthase (NOS) polyadenylation signal from *Agrobacterium tumefaciens*. Our subsequent vectors, described in Examples 1–5, utilized modifications of the 5' and 3' regulatory regions.

Following is a description of the construction of pLTB120. We digested pJC217 of Example 1 with EcoRI and HindIII to give a 580 bp fragment which was ligated with pbluescript KS (Stratagene) to give pLTB10. The EcoRI site in pLTB10 was removed by digestion with EcoRI and mung bean nuclease, then the plasmid was religated to give pLTB11. The LT-B coding region was obtained on a 410 bp fragment from pLTB11 by digestion with BamHI and DraI, and ligated with pBI221 (Clonetech, Palo Alto, Calif.) that had been digested with SacI, blunted with mung bean nuclease, and digested with BamHI. The resulting plasmid, pLTB220, has the LT-B coding sequence substituted for the GUS coding sequence in pBI221. The LT-B expression cassette in pLTB220 was removed by digestion with HindIII and EcoRI, and ligated with pBI101 (Clonetech, Palo Alto, Calif.) digested likewise, to give pLTB120. Thus, pLTB120 is a T-DNA vector containing the left and right borders required for Agrobacterium-mediated integration into plant nuclear DNA, the 35S promoter, and the NOS terminator regulating expression of the LT-B coding sequence (FIG. 11).

We transformed tobacco plants with pLT120 as described in Example 6, and analyzed total leaf RNA by Northern blotting as described in Example 17. On the same gel we analyzed RNA from tobacco cells transformed with pLTB112 of Example 21, and pLT100 and pLT101 of Example 3. These samples represent mRNA containing the LT-B coding sequence fused to the NOS 3'-untranslated region and polyadenylation signal (pLTB120), or the soybean vspB 3' untranslated region and polyadenylation signal (pLTB112, pLT100, pLT101). The radiogram shown in FIG. 17 indicates that the pLTB120 cassette yields 2 different species of mRNA, as shown by 2 distinct bands that hybridize with the LT-B probe. However, LT-B mRNA's derived from the expression cassettes in pLTB112, pLT100 and pLT101 all show only a single band, indicating a single species of mRNA. This band is larger than the larger pLTB120 band due to the presence of the TEV 5'-untranslated region.

The occurrence of 2 mRNA species in the pLTB120 transformant is likely due to polyadenylation of the nascent transcripts at alternative sites. The native coding sequence of LT-B contains a canonical polyadenylation signal, "AAUAAA", near its 3' end which, when fused to the NOS 3' region in pLTB120, allows recognition and 3'-end processing to yield an mRNA species that is shorter than that generated by processing due to the "AAUAAA" signal in the NOS 3' region. By visual inspection of the radiogram, it appears that the 2 alternative sites are utilized with approximately equal frequency in the tobacco cells. A truncated mRNA may be non-functional and lead to lower expression of LT-B protein. Conversely, when the LT-B coding sequence is fused to the soybean vspb 3' region, only a single, full-length mRNA species results, perhaps by virtue of a longer 3'-untranslated sequence separating the cryptic polyadenylation signal in the LT-B coding sequence from that in the vspB 3' region.

Figure 17:
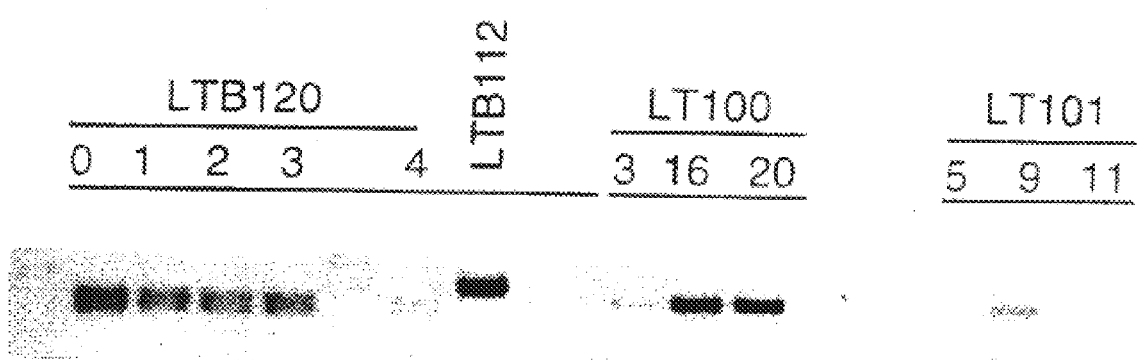
FIG. 17 depicts LT-B encoding mRNA in tobacco leaves (LTB120 and LTB112) and microtubers (LT100 and LT101).

As shown in FIG. 17, tobacco leaf (LTB120 and LTB112) or microtuber (LT100 and LT101) total RNA samples were prepared, and 3 μg (LTB120) or 6 μg (LTB112, LT100, LT101) of each sample was denatured with formaldehyde and electrophoresed in a 1.7% agarose gel. The gel was blotted to a nylon membrane and hybridized with probe specific for the LT-B coding sequence. After washing the membrane was exposed to X-ray film, and the developed radiogram scanned with a flat-bed scanner. The numbers indicate individual transformed plants.

EXAMPLE 31

This example illustrates the enhancement of expression of LT-B in plant cells using the synthetic gene with modified nucleotide sequence of Example 20.

Potato plants of strain "$FL_{1607}$" were transformed by Agrobacterium-mediated T-DNA transfer using pTH110 of Example 20, by the method of Example 14. Transformants were regenerated on selective medium containing kanamycin, and leaves of regenerating shoots were excised and extracted for LT-B ELISA.

Fifteen independent pTH110 transformants were analyzed along with control plants: 1) untransformed potato plant, 2) a potato plant transformed with pLTB110 of Example 1 and expressing LT-B at a high level compared with other pLTB110 transformants, and 3) a potato plant transformed with pLTK110 of Example 1 and expressing LT-B-SEKDEL at a high level compared with other pLTK110 transformants. The best estimate of the level of enhancement of LT-B expression in pTH110 transformants is obtained by comparison of the pTH110 transformants with the pLTB110 transformant, because the amino acid sequence of these LT-B genes is identical, whereas the pLTK110 cassette has a carboxy-terminal extension of 6 amino acids (SEKDEL) which allows microsomal retention and enhanced accumulation of antigen.

Leaves of diameter 4 mm were excised from the top of the plants and frozen in liquid nitrogen. The tissue was homogenized in 250 microliters of ice cold extraction buffer (25 mM sodium phosphate (pH 6.6), 100 mM NaCl, 10 mM EDTA, 25 mM sodium ascorbate, 10 microgram/ml leupeptin and 0.1% Tween-20). The samples were centrifuged at 14,000 rpm in a micro-centrifuge at 4° C. for 2 minutes. The supernatant was removed and diluted 1:100 with 1% dry milk in PBST (10 mM sodium phosphate buffer (pH 7.2), 105 mM NaCl and 0.05% Tween 20), and LT-B determined by the ELISA protocol of Example 7, modified as follows. After incubation of the plates with the primary antibody (goat anti-LT-B) and washing, the plates were treated with rabbit anti-goat 1 gG conjugated to horseradish peroxidase (HRP), diluted 1:3000 in 1% dry milk/PBST for 2 hours at 37° C. After washing, the plates were developed with slow TMB substrate for HRP (Pierce, Rockford, Ill.) for 30 minutes at room temperature.

The total protein of the leaf extracts was quantified using BIORAD protein assay kit and BSA as standard. The values were averaged and tabulated as ELISA equivalent LT-B in nanogram per microgram of total soluble protein. The results are shown in Table 10. These data indicate that the 6 pTH110 transformants expressing LT-B at the highest levels showed LT-B accumulation at 3 to 14 times higher than the pLTB110-2 transformant, and up to 5 times higher than the pLTK110-4 transformant. This result clearly shows the value of using a modified nucleotide sequence of the coding region of the LT-B gene.

TABLE 10

LT-B Levels in Leaves of Potato Plants Transformed with Synthetic or Native LT-B Gene Expression Plasmids

| Transformant | Gene | T-B ng/ug total soluble protein |
|---|---|---|
| TH110-2 | Synthetic | 0.99 |
| TH110-3 | " | 0.88 |
| TH110-4 | " | 0.44 |
| TH110-7 | " | 0.61 |
| TH110-9 | " | 0.19 |
| H110-12 | " | 0.46 |
| LTB110-2 | Native LT-B | 0.07 |
| LTK110-4 | Native LT-B + SEKDEL | 0.19 |
| Untransformed | None | 0.00 |

While in accordance with the patent statutes, the best mode and preferred embodiments of the invention have been described, it is to be understood that the invention is not limited thereto, but rather is to be measured by the scope and spirit of appended claims.

We claim:

1. A transgenic plant material comprising:
    a DNA sequence encoding a first immunogenic agent selected from the group consisting of a DNA sequence encoding an *E. coli* enterotoxin (LT) antigen and a DNA sequence encoding a cholera toxin (CT) antigen, wherein the DNA sequence is operably linked to nucleotide sequences coding for an endoplasmic reticulum (R) signal sequence and an ER retention sequence which causes the intracellular retention of the antigen.

2. The material of claim 1, wherein the antigen oligomer to form a LT holotoxin or a CT holotoxin.

3. The material of claim 1 wherein said transgenic plant material is capable of inducing a humoral and secretory immune response in animals directed against said immunogenic agent when animals are administered the transgenic plant material by oral ingestion.

4. The material of claim 1, further comprising a DNA sequence encoding a second immunogenic agent.

5. The material of claim 4, wherein the second immunogenic agent comprises a viral antigen.

6. The material of claim 5, wherein the enterotoxin antigen or the cholera toxin antigen elicits an adjuvant effect upon the viral antigen.

7. The material of claim 1 wherein the first immunogenic agent is encoded by the synthetic LT-B gene sequence presented in SEQ ID NO. 20.

8. A method for inducing an antibody response in animals via oral administration with transgenic plants expressing immunogens comprising the steps of:

orally administering to an animal a transgenic plant material comprising a DNA sequence encoding a first immunogenic agent selected from the group consisting of a DNA sequence encoding an *E. coli* enterotoxin (LT) antigen and a DNA sequence encoding a cholera toxin (CT) antigen, wherein the DNA sequence is operably linked to nucleotide sequences coding for an endoplasmic reticulum (ER) signal sequence and an ER retention sequence which causes the intracellular retention of the antigen.

9. The method of claim 8, wherein the immunogenic agent is encoded by the synthetic LT-B gene sequence presented in SEQ ID NO. 20.

10. The method of claim 8, wherein the antigen oligomer to form a LT holotoxin or a CT holotoxin.

11. The method of claim 8, further comprising a DNA sequence encoding a second immunogenic agent.

12. The method of claim 11, herein the second immunogenic agent comprises a viral antigen.

13. The method of claim 12, wherein the enterotoxin antigen or the cholera toxin antigen elicits an adjuvant effect upon the viral antigen.

14. A method for immunizing animals via oral administration with transgenic plants expressing immunogens comprising the steps of:

administering to an animal a transgenic plant material comprising at least one immunogenic agent selected from the group consisting of an *E. coli* enterotoxin (LT) antigen modified to contain an ER retention sequence, and a cholera toxin (CT) antigen modified to contain an ER retention sequence.

15. The method of claim 14, farther comprising a DNA sequence encoding a second immunogenic agent, wherein the second immunogenic agent comprises a viral antigen.

* * * * *

UNITED STATES PATENT AND TRADEMARK OFFICE
CERTIFICATE OF CORRECTION

PATENT NO. : 6,395,964 B1
DATED : May 28, 2002
INVENTOR(S) : Charles J. Arntzen et al.

It is certified that error appears in the above-identified patent and that said Letters Patent is hereby corrected as shown below:

Column 1,
Line 10, delete "A".

Column 3,
Line 50, delete "4".

Column 4,
Line 21, delete "rification" and insert -- purification --

Column 6,
Line 41, delete "protoplagtg" and insert -- protoplasts --
Line 52, delete "protoplact" and insert -- protoplast --

Column 7,
Line 18, delete "as".

Column 8,
Line 28, delete "trdnsgenic" and insert -- transgenic --

Column 9,
Lines 42-43, delete "trantgetic" and insert -- transgenic --

Column 10,
Line 1, insert -- . -- after "tion", and capitalize "colonization" to start a new sentence.
Line 46, insert -- s -- after sequence.

Column 13,
Line 5, delete "CT-D" and insert -- CT-B --
Line 55, delete "m" and insert -- may --

Column 14,
Line 4, delete "p".

Column 15,
Line 26, delete "ug" and insert -- µg --

UNITED STATES PATENT AND TRADEMARK OFFICE
CERTIFICATE OF CORRECTION

PATENT NO. : 6,395,964 B1
DATED : May 28, 2002
INVENTOR(S) : Charles J. Arntzen et al.

It is certified that error appears in the above-identified patent and that said Letters Patent is hereby corrected as shown below:

<u>Column 16,</u>
Line 2, delete "andoplasmic" and insert -- endoplasmic --
Line 25, insert a space between "transgenic" and "plants".
Line 30, delete "LT-D" and insert -- LT-B --
Line 41, delete "GIU" and insert -- Glu --
Line 55, delete "CT-D" and insert -- CT-B --

<u>Column 17,</u>
Line 40, delete "t" at the end of "entertoxin" and insert -- a comma --

<u>Column 18,</u>
Line 12, delete "antigenc" and insert -- antigens --

<u>Column 19,</u>
Line 25, delete "CT-D" and insert -- CT-B --
Line 46, delete "CaNV" and insert -- CaMV --

<u>Column 20,</u>
Line 65, delete "TT-B SEXDEL" and insert -- LT-B SEKDEL --

<u>Column 21,</u>
Line 13, delete "pg" and insert -- µg --

<u>Column 23,</u>
Line 1, delete "Ba-mHI" and insert -- BamHI --
Line 9, "CCATGG" of the sequence ID No. 8 should be underlined.
Line 17, delete "BaMHI" and insert -- BamHI --
Line 20, delete "pRZL4. pRZL4" and insert -- pRTL4. pRTL4 --
Line 52, delete "selpction" and insert -- selection --
Line 59, delete "DATP" and insert -- dATP --

<u>Column 24,</u>
Line 3, delete "pLTK110" and insert -- pLTB110 --
Line 17, "CCATGG" of the sequence ID No. 10 should be underlined.
Line 32, delete "vspb" and insert -- vspB --

UNITED STATES PATENT AND TRADEMARK OFFICE
CERTIFICATE OF CORRECTION

PATENT NO.    : 6,395,964 B1
DATED         : May 28, 2002
INVENTOR(S)   : Charles J. Arntzen et al.

It is certified that error appears in the above-identified patent and that said Letters Patent is hereby corrected as shown below:

Column 25,
Line 8, delete "namHI" and insert -- BamHI --
Line 22, delete "pxg" and insert -- pKS --
Line 28, delete "NeoI" and insert -- NcoI --
Line 34, delete "nopdline" and insert -- nopaline --
Line 44, delete "5S" and insert -- 5' --
Line 46, delete "polyadanylation" and insert -- polyadenylation --

Column 26,
Line 12, delete "$_3$'" and insert -- 3' --. There is no subscript.
Line 56, delete "LT-n-polypepcider" and insert -- LT-B polypeptide --

Column 27,
Line 1, delete "Ba-mHI" and insert -- BamHI --
Line 2, delete "DATP" and insert -- dATP --
Line 7, delete "Sacd" and insert -- SacI --
Line 50, delete "SaIII" and insert -- SalI --

Column 28,
Line 38, delete "glect" and insert -- select --
Line 58, delete "of f" and insert -- off --

Column 29,
Line 14, delete "LT-D" and insert -- LT-B --
Line 33, delete "procipitation" and insert -- precipitation --
Lines 44 and 45, delete "MM" and insert -- mM --
Line 50, delete "gal." and insert -- gel --
Line 51, delete "Dio-Rac pre-stainea" and insert -- Bio-Rad pre-stained --
Line 64, delete "MM" and insert -- mM --

Column 30,
Line 25, delete "15,00xg" and insert -- 15,000xg --
Line 38, delete "pg" and insert -- μg --
Line 44, delete "Retamine." and insert -- Ketamine. --
Line 48, ddelete "MM" and insert -- mM --

UNITED STATES PATENT AND TRADEMARK OFFICE
CERTIFICATE OF CORRECTION

PATENT NO.      : 6,395,964 B1
DATED           : May 28, 2002
INVENTOR(S)     : Charles J. Arntzen et al.

It is certified that error appears in the above-identified patent and that said Letters Patent is hereby corrected as shown below:

Column 33,
Line 5, delete "5 ml/L" and insert -- 5 mg/L --
Line 43, delete "an" and insert -- as --

Column 34,
Line 11, delete "CHC13" and insert -- $CHCl_3$ --

Column 35,
Line 26, delete the space between "f" and "ed".

Column 38,
Table 3, on line 11 of typed symbols, "A TTT A" should be underlined, i.e., -- <u>A TTT A</u> --

Column 40,
Line 51, "CCATGG" of seq. ID No. 22 should be underlined, i.e., -- <u>CCATGG</u> --
Line 54, delete "Cla1" and insert -- ClaI --

Column 41,
Lines 8 and 11, delete "paSIG-GUS," and insert -- pαSIG-GUS --
Line 35, delete "cide" and insert -- side --

Column 43,
Line 64, "The serum samples from" is not part of item 13 and should start a new paragraph.

Column 45,
Line 17, delete "grala" and insert -- gram --

Column 46,
Line 23, delete "Necastle" and insert -- Newcastle --
Line 35, delete "Immunga Ragnn" and insert -- Immunse Response --
Line 42, delete "log10" and insert -- $log_{10}$ --

UNITED STATES PATENT AND TRADEMARK OFFICE
CERTIFICATE OF CORRECTION

PATENT NO.    : 6,395,964 B1
DATED         : May 28, 2002
INVENTOR(S)   : Charles J. Arntzen et al.

It is certified that error appears in the above-identified patent and that said Letters Patent is hereby corrected as shown below:

<u>Column 47,</u>
Line 10, insert -- Group 1 -- above "Individual Sera" and change "Gnp" above "Mean" to -- Group --
Line 56, delete "pbluescript" and insert -- pBluescript --

<u>Column 48,</u>
Line 7, delete "pLT120" and insert -- pLTB120 --
Line 38, delete "vspb" and insert -- vspB --
Line 58, delete "FL$_{1607}$" and insert -- Fl1607 --

<u>Column 50,</u>
Table 10, delete "H110-12" and insert -- TH110-12 -- under "Transformant"

<u>Column 59,</u>
Line 23, delete "(R)" and insert -- (ER) --
Line 25, delete "oligomer" and insert -- oligomerizes --

<u>Column 60,</u>
Line 22, insert -- first -- before "immunogenic"
Line 24, delete "oligomer" and insert -- oligomerizes --
Line 29, delete "herein" and insert -- wherein --

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,395,964 B1
DATED : May 28, 2002
INVENTOR(S) : Charles J. Arntzen et al.

It is certified that error appears in the above-identified patent and that said Letters Patent is hereby corrected as shown below:

<u>Title page,</u>
Item [75], Inventors, delete "Haq A. Tariq" and insert -- Tariq A. Haq --

Signed and Sealed this

Twenty-sixth Day of August, 2003

JAMES E. ROGAN
*Director of the United States Patent and Trademark Office*

SEQUENCE LISTING

```
(1) GENERAL INFORMATION:

(iii) NUMBER OF SEQUENCES: 23

(2) INFORMATION FOR SEQ ID NO:1:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:1:

Lys Asp Glu Leu
1

(2) INFORMATION FOR SEQ ID NO:2:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:2:

His Asp Glu Leu
1
```

(2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:3:

```
Ser Glu Lys Asp Glu Leu
1               5
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:4:

```
Ser Glu His Asp Glu Leu
1               5
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

```
CTCTGAGAAA GATGAGCTAT GA                                              22
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

```
CTAGTCATAG CTCATCTTTC TCAGAG                                          26
```

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:7:

```
AGTATGGAAA ACTCTGAGAA AGATGAGCTA TGACTAGT                             38
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:8:

GGGGCCATGG TTAAAGTAAA ATGTTATGTT TTA                                      33

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

AGACTGGGGA GCTCCGTATG                                                     20

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:10:

GGGGCCATGG TTAAAAATAT AACTTTCATT TTT                                      33

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

ATCTGGGGGT CTAGAGTC                                                       18

(2) INFORMATION FOR SEQ ID NO:12:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (xi) SEQUENCE DESCRIPTION: SEQ ID NO:12:

TCGAGGCCAT GGTGAAGGTG AAGTGCTATG TGCTCTTCAC TGCTCTCCTC AGCTCTCTTT          60

GTGCTTATGG                                                                70

(2) INFORMATION FOR SEQ ID NO:13:

(i) SEQUENCE CHARACTERISTICS:
        (A) LENGTH: 70 base pairs
        (B) TYPE: nucleic acid
        (C) STRANDEDNESS: double
        (D) TOPOLOGY: linear (xi) SEQUENCE DESCRIPTION: SEQ ID NO:13:

TGCTTATGGA GCTCCACAAT CCATCACTGA GCTTTGCTCT GAGTACAGGA ACACTCAGAT          60

CTACACCATC                                                                70

(2) INFORMATION FOR SEQ ID NO:14:

(i) SEQUENCE CHARACTERISTICS:
        (A) LENGTH: 72 base pairs
        (B) TYPE: nucleic acid
        (C) STRANDEDNESS: double (D) TOPOLOGY: linear (xi) SEQUENCE DESCRIPTION: SEQ ID NO:14:

TACACCATCA ATGACAAGAT CCTCTCTTAC ACTGAGAGCA TGGCTGGCAA GAGGGAGATG    60

GTGATCATCA CC    72

(2) INFORMATION FOR SEQ ID NO:15:

(i) SEQUENCE CHARACTERISTICS:
        (A) LENGTH: 68 base pairs
        (B) TYPE: nucleic acid
        (C) STRANDEDNESS: double
        (D) TOPOLOGY: linear (xi) SEQUENCE DESCRIPTION: SEQ ID NO:15:

ATCATCACCT TCAAGTCAGG AGCCACTTTC CAGGTGGAGG TTCCAGGCTC ACAACACATC    60

GATCTGCA    68

(2) INFORMATION FOR SEQ ID NO:16:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (xi) SEQUENCE DESCRIPTION: SEQ ID NO:16:

TCGAGATCGA TTCCCAGAAG AAGGCCATTG AGAGGATGAA GGACACCTTG AGGATCACCT    60

ACCTC    65

(2) INFORMATION FOR SEQ ID NO:17:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (xi) SEQUENCE DESCRIPTION: SEQ ID NO:17:

CCTACCTCAC TGAGACCAAG ATTGACAAGC TCTGTGTGTG GAACAACAAG ACTCCAAACT    60

CCATT    65

(2) INFORMATION FOR SEQ ID NO:18:

(i) SEQUENCE CHARACTERISTICS:
        (A) LENGTH: 52 base pairs
        (B) TYPE: nucleic acid
        (C) STRANDEDNESS: double
        (D) TOPOLOGY: linear (xi) SEQUENCE DESCRIPTION: SEQ ID NO:18:

AACTCCATTG CTGCCATCAG CATGGAGAAC TAAGTCTTCG GTACCTATCT AG    52

(2) INFORMATION FOR SEQ ID NO:19:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (xi) SEQUENCE DESCRIPTION: SEQ ID NO:19:

GCTCCCCAGT CTATTACAGA ACTATGTTCG GAATATCGCA ACACACAAAT ATATACGATA    60

```
AATGACAAGA TACTATCATA TACGGAATCG ATGGCAGGCA AAAGAGAAAT GGTTATCATT      120

ACATTTAAGA GCGGCGCAAC ATTTCAGGTC GAAGTCCCGG GCAGTCAACA TATAGACTCC      180

CAAAAAAAAG CCATTGAAAG GATGAAGGAC ACATTAAGAA TCACATATCT GACCGAGACC      240

AAAATTGATA ATTATGTGT ATGGAATAAT AAAACCCCCA ATTCAATTGC GGCAATCAGT       300

ATGGAAAACT GA                                                         312
```

(2) INFORMATION FOR SEQ ID NO:20:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (xi) SEQUENCE DESCRIPTION: SEQ ID NO:20:

```
GCTCCACAAT CCATCACTGA GCTTTGCTCT GAGTACAGGA ACACTCAGAT CTACACCATC       60

AATGACAAGA TCCTCTCTTA CACTGAGAGC ATGGCTGGCA AGAGGGAGAT GGTGATCATC      120

ACCTTCAAGT CAGGAGCCAC TTTCCAGGTG GAGGTTCCAG GCTCACAACA CATCGATTCC      180

CAGAAGAAGG CCATTGAGAG GATGAAGGAC ACCTTGAGGA TCACCTACCT CACTGAGACC      240

AAGATTGACA AGCTCTGTGT GTGGAACAAC AAGACTCCAA ACTCCATTGC TGCCATCAGC      300

ATGGAGAACT AA                                                         312
```

(2) INFORMATION FOR SEQ ID NO:21:

(i) SEQUENCE CHARACTERISTICS:
        (A) LENGTH: 103 amino acids
        (B) TYPE: amino acid
        (D) TOPOLOGY: linear (xi) SEQUENCE DESCRIPTION: SEQ ID NO:21:

```
Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100
```

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:22:

```
GGGGCCATGG CTCCCCAGTC TATT                                             24
```

(2) INFORMATION FOR SEQ ID NO:23:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:23:

TGCCATCGAT TCCGTATA                                                    18